(12) United States Patent
Brown et al.

(10) Patent No.: US 7,557,219 B2
(45) Date of Patent: Jul. 7, 2009

(54) METHODS FOR MAKING 4-TETRAZOLYL-4-PHENYLPIPERIDINE COMPOUNDS

(75) Inventors: Kevin Brown, Philadelphia, PA (US); Timothy J. Doyle, Morristown, NJ (US); John W. F. Whitehead, Newtown, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 11/495,221

(22) Filed: Jul. 28, 2006

(65) Prior Publication Data
US 2007/0072909 A1 Mar. 29, 2007

Related U.S. Application Data

(63) Continuation-in-part of application No. PCT/US2005/003170, filed on Jan. 31, 2005.
(60) Provisional application No. 60/552,982, filed on Mar. 11, 2004, provisional application No. 60/540,839, filed on Jan. 30, 2004.

(51) Int. Cl.
C07D 257/04 (2006.01)
A61K 31/445 (2006.01)
(52) U.S. Cl. ...................................... 548/250; 514/326
(58) Field of Classification Search ................. 548/250; 514/326
See application file for complete search history.

(56) References Cited

U.S. PATENT DOCUMENTS

| 5,412,102 A * | 5/1995 | Clark et al. .................. 548/253 |
| 5,502,191 A * | 3/1996 | Galante ....................... 544/284 |
| 5,606,037 A | 2/1997 | Attardo et al. |
| 5,736,523 A | 4/1998 | Attardo et al. |
| 5,849,737 A | 12/1998 | Chaplan et al. |
| 5,849,761 A | 12/1998 | Yaksh |
| 5,994,372 A | 11/1999 | Yaksh |
| 6,166,039 A | 12/2000 | Yaksh |
| 6,166,085 A | 12/2000 | Chaplan et al. |
| 6,221,888 B1 | 4/2001 | Durette et al. |
| 6,358,945 B1 | 3/2002 | Breitfelder et al. |
| 6,362,203 B1 | 3/2002 | Mogi et al. |
| 6,423,519 B1 | 7/2002 | Bergnes et al. |
| 6,486,142 B2 | 11/2002 | Leblanc et al. |
| 6,544,981 B2 | 4/2003 | Stein et al. |
| 6,573,282 B1 | 6/2003 | Yaksh et al. |
| 6,576,650 B1 | 6/2003 | Yaksh |
| 6,586,430 B1 | 7/2003 | Armour et al. |
| 6,608,052 B2 | 8/2003 | Breitfelder et al. |
| 6,703,525 B2 | 3/2004 | Kapadia et al. |
| 6,790,854 B2 | 9/2004 | Tsushima et al. |
| 7,005,436 B2 | 2/2006 | Lloyd et al. |

FOREIGN PATENT DOCUMENTS

| CA | 949560 | 6/1974 |
| EP | 1097924 | 5/2001 |
| EP | 1219294 | 7/2002 |
| EP | 1277737 | 1/2003 |
| EP | 1325912 | 7/2003 |
| WO | WO 97/24325 | 7/1997 |
| WO | WO 99/45011 | 9/1999 |
| WO | WO 00/39125 | 7/2000 |
| WO | WO 01/39775 | 6/2001 |
| WO | WO 03/088908 A2 | 10/2003 |
| WO | WO 2004/046132 | 6/2004 |
| WO | WO 2004/046132 A1 * | 6/2004 |

OTHER PUBLICATIONS

Demo et al. Organic Letters, 2002 4(15) 2525.*
Bold, et al., "New Aza-Dipeptide Analogues as Potent and Orally Absorbed HIV-1 Protease Inhibitors: Candidates for Clinical Development," J. Med. Chem., 41:3387-3401 (1998).
Fisher, et al., "5-Aroyltetrazoles," publication?, 24:1650-1654 (1959).
Giardina, et al., "A Reliable and Efficient Synthesis of SR 142801," Biorganic & Medicinal chemistry Letters, vol. 6, No. 19, pp. 2307-2310 (1996).

(Continued)

Primary Examiner—D. Margaret Seaman
Assistant Examiner—Nizal S Chandrakumar
(74) Attorney, Agent, or Firm—Dechert LLP

(57) ABSTRACT

Methods, composition, and intermediates are disclosed that are useful for making 4-Tetrazolyl-4-phenylpiperidine Compounds according to Formula I,

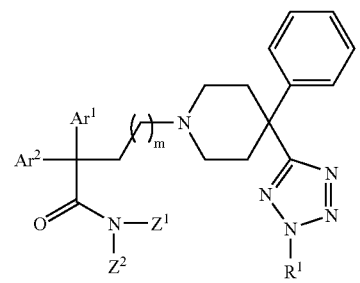

Formula (I)

where $Ar^1$ is $—C_3-C_8$ cycloalkyl, phenyl, naphthyl, anthryl, phenanthryl or -(5-7-membered) heteroaryl, each being unsubstituted or substituted with one or more $R^2$ groups; $Ar^2$ is phenyl, naphthyl, anthryl, phenanthryl or -(5-7-membered) heteroaryl, each being unsubstituted or substituted with one or more $R^2$ groups; $Z^1$ and $Z^2$ are each independently a $—(C_1-C_4$ alkyl) group; $R^1$ is $—(CH_2)_nC(O)N(R^3)(R^4)$ where $R^3$ and $R^4$ are each independently H or $—(C_1-C_4$ alkyl); $R^2$ is halogen, $—C_1-C_3$ alkyl, $—O—(C_1-C_3$ alkyl), $—NH(C_1-C_3$ alkyl) or $—N(C_1-C_3$ alkyl)$_2$; n is an integer ranging from 1 to 4; m is an integer ranging from 0 to 4; and, in certain embodiments, the phenyl moiety attached to the 4-position of the piperidine ring of a compound according to Formula I can be optionally substituted with one or more $R^2$ groups.

18 Claims, No Drawings

OTHER PUBLICATIONS

Harrison, et al., "Conversation of carboxamides and oximes to nitriles or imidoyl chlorides using a polymer-supported phosphine and carbon tetrachloride," Synthesis, pp. 41-43 (1997).

Jaiswal, et al., "Anticonvulsant Property of Substituted 5-Aryltetrazol-2-ylacetylcarbamides," J. Heterocyclic Chem., 20:615-617 (1983).

Jenkins, et al., "Substituent variation in azabicyclic triazole- and tetrazole-based muscarinic receptor ligands," J. Med. Chem., 35:2392-2406 (1992).

Koguro, et al., "Novel synthesis of 5-Substituted Tetrazoles from Nitriles," Synthesis, pp. 910-914 (1998.

Kwartler, et al., "The Preparation of Substituted 4-Aminomethylpiperidines and their Straight Chain Analogs," publication?, 69:2582-2586 (1947).

Perrine, "Quinuclidines.I.4-Phenylquinuclidines as Potential Analgesics," publication, 22:1484-1489 (1957).

Sato, et al., "New µ-opioid receptor agonists with phenoxyacetic acid moiety," Chem. Pharm. Bull. 50:292-297 (2002).

Satzinger, "5-Substituierte Und 1.5-Kondensierte Tetrazole," publication, pp. 159-173 (1960).

Schaefer, et al., ,,Synthese, physikalisch-chemische Eigenschaften und orientierende pharmakologische Untersuchungen von Budipin und verwandten 4,4-Diphenylpiperidinen, Arzpeim-Forsch., Drug. Res. 34(1), Nr. 3, pp. 233-240 (1984).

Stokbroekx, et al., ,,Synthetic Antidiarrheal Agents. 2,2-Diphenyl-4-(4'aryl-4'-hydroxypiperidino)butyramides, Journal of Medicinal Chemistry, vol. 16, No. 7, pp. 782-786 (1973).

* cited by examiner

METHODS FOR MAKING 4-TETRAZOLYL-4-PHENYLPIPERIDINE COMPOUNDS

This application is a continuation-in-part of PCT/US2005/003170 filed Jan. 31, 2005, which claims the benefit of U.S. Ser. No. 60/540,839 filed Jan. 30, 2004 and U.S. application Ser. No. 60/552,982 filed Mar. 11, 2004, each of which is incorporated by reference herein in its entirety.

1. FIELD OF THE INVENTION

The present invention relates to compositions, intermediates, and methods for making 4-Tetrazolyl-4-phenylpiperidine Compounds.

2. BACKGROUND OF THE INVENTION

Pain is the most common symptom for which patients seek medical advice and treatment. Pain can be acute or chronic. While acute pain is usually self-limited, chronic pain can persist for three months or longer and lead to significant changes in a patient's personality, life style, functional ability or overall quality of life (K. M. Foley, *Pain*, in *Cecil Textbook of Medicine* 100-107, J. C. Bennett and F. Plum eds., 20th ed. 1996).

Traditionally, pain has been managed by administering a non-opioid analgesic, such as acetylsalicylic acid, choline magnesium trisalicylate, acetaminophen, ibuprofen, fenoprofen, diflusinal and naproxen, or by administering an opioid analgesic, such as morphine, hydromorphone, methadone, levorphanol, fentanyl, oxycodone and oxymorphone. Id.

4-Tetrazolyl-4-phenylpiperidine Compounds, including but not limited to those according to Formula I, are useful for preventing or treating pain or diarrhea in an animal,

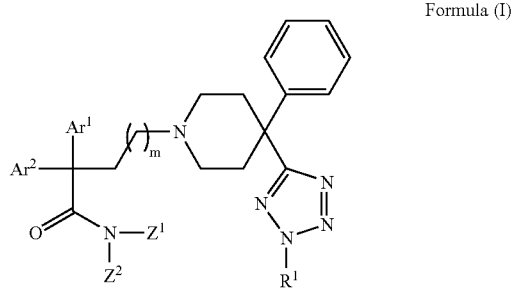

Formula (I)

where $Ar^1$ is —$C_3$-$C_8$ cycloalkyl, phenyl, naphthyl, anthryl, phenanthryl or -(5-7-membered) heteroaryl, each being unsubstituted or substituted with one or more $R^2$ groups; $Ar^2$ is phenyl, naphthyl, anthryl, phenanthryl or -(5-7-membered) heteroaryl, each being unsubstituted or substituted with one or more $R^2$ groups; $Z^1$ and $Z^2$ are each independently a —($C_1$-$C_4$ alkyl) group; $R^1$ is —$(CH_2)_n$C(O)N($R^3$)($R^4$) where $R^3$ and $R^4$ are each independently H or —($C_1$-$C_4$ alkyl); $R^2$ is halogen, —$C_1$-$C_3$ alkyl, —O—($C_1$-$C_3$ alkyl), —NH($C_1$-$C_3$ alkyl) or —N($C_1$-$C_3$ alkyl)$_2$; n is an integer ranging from 1 to 4; and m is an integer ranging from 0 to 4. In certain embodiments, the phenyl moiety attached to the 4-position of the piperidine ring of a compound according Formula I is optionally substituted with one or more $R^2$ groups, where $R^2$ is as defined above.

Compound (7), an illustrative 4-Tetrazolyl-4-phenylpiperidine Compound useful for preventing and treating pain and diarrhea in an animal, has the following structure:

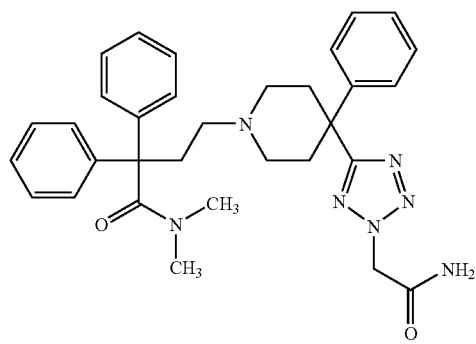

Compound (7)

(4-[4-(2-carbamoylmethyl-2H-tetrazol-5-yl)-4-phenyl-piperidin-1-yl]-N,N-dimethyl-2-2-diphenyl-butyramide)

Illustrative 4-Tetrazolyl-4-phenylpiperidine Compounds, methods for their synthesis, and methods for preventing and treating pain or diarrhea in an animal comprising administering to an animal in need of such treatment or prevention an effective amount of a 4-Tetrazolyl-4-phenylpiperidine Compound, are disclosed in co-owned U.S. application Ser. No. 10/714,066, filed Nov. 13, 2003, and published as US 2004/0152689 A1 on Aug. 5, 2004, which is hereby incorporated by reference in its entirety.

In addition, methods for making other 4-phenylpiperidine compounds have been described. For example, U.S. Pat. No. 6,573,282 B1 to Yaksh et al. describes the synthesis of loperamide (4-(p-chlorophenyl)-4-hydroxy-N,N-dimethyl-α,α-diphenyl-1-piperidinebutyramide hydrochloride). More specifically, the '282 patent describes the synthesis of dimethyl-(tetrahydro-3,3-diphenyl-2-furylidene)ammonium bromide and its condensation with p-chlorophenyl-4-piperidinol to provide 4-(p-chlorophenyl)-4-hydroxy-N,N-dimethyl-α, α-diphenyl-1-piperidinebutyramide. However, the '282 patent does not describe the synthesis of any compounds comprising a tetrazole moiety.

A number of approaches have been disclosed concerning the formation of tetrazole groups from nitrile substituents. For example, Berstein et al. *J. Synth. Org. Chem.* (1987) 12: 1133-34 describes formation of certain tetrazole derivatives by reacting the corresponding nitrile compound with sodium azide in N-methyl pyrrolidone in the presence of triethylammonium chloride at a temperature of 150° C.

Demko et al. (2001) *J. Org. Chem.* 66: 7945-7850 reports conversion of a nitrile substituent to a tetrazole by reacting the nitrile-containing molecule with sodium azide in the presence of zinc bromide. The reactions described by Demko are carried out in an aqueous solution.

Bold et al. (1998) *J. Med. Chem.* 41: 3387-3401 describes conversion of a nitrile to the corresponding tetrazole by reacting the nitrile-containing molecule with sodium azide in the presence of lithium chloride, using methoxyethanol as the solvent, under reflux conditions.

Moltzen et al. (1994) *J. Med. Chem.* 37: 4085-4099 describes conversion of the nitrile moiety of a heterocyclic alkenyl compound to the corresponding nitrile by reaction with sodium azide in the presence of aluminum trichloride in THF under reflux conditions.

Despite the procedures described in the cited references, there exists a need for improved methods for making tetrazolyl-containing compounds, and, even more particularly, for improved methods for making 4-Tetrazolyl-4-phenylpiperidine Compounds, e.g. those according to Formula I, which include but are not limited to Compound (7).

Citation of any reference in Section 2 of this application is not an admission that the reference is prior art to the application.

3. SUMMARY OF THE INVENTION

In one embodiment, the invention relates to a compound of formula (2),

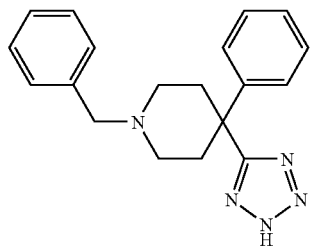

(2)

which is useful for synthesizing compounds according to Formula I, such as, but not limited to, Compound (7).

In another embodiment, the invention relates to a compound of formula (4)

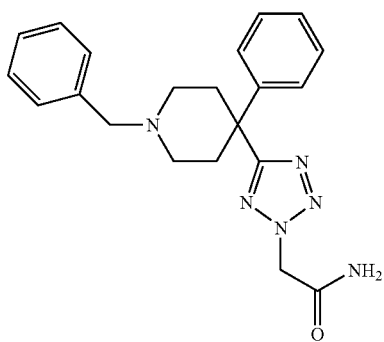

(4)

which is useful for synthesizing compounds according to Formula I such as, but not limited to, Compound (7).

In a further embodiment, the present invention is directed toward a compound of formula (9)

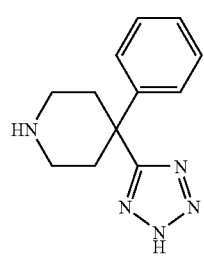

(9)

which is useful for synthesizing compounds according to Formula I such as, but not limited to, Compound (7).

In still another embodiment, the present invention is directed toward a compound of formula (5)

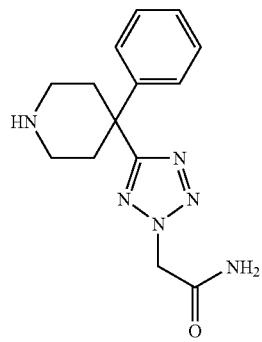

(5)

which is useful for synthesizing compounds according to Formula I such as, but not limited to, Compound (7).

In another embodiment, the present invention also relates to a composition comprising sodium azide; a zinc salt; a solvent comprising a polar aprotic solvent, and a compound of formula (2)

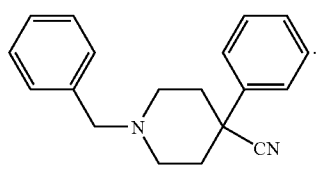

(2)

In one embodiment, the solvent comprises a mixture of N-methyl pyrrolidone and water.

In another embodiment, the present invention is directed toward a composition, which is useful for the synthesis of compounds according to Formula I (including e.g Compound (7)) comprising a polar aprotic solvent; a non-nucleophilic base; a compound according to formula (2)

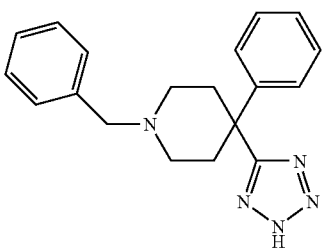

(2)

and an alkylating agent having a structure according to Formula II

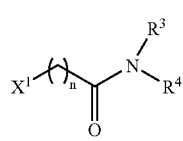

(II)

in which n is an integer from 1 to 4; $R^3$ and $R^4$ are each independently H or —($C_1$-$C_4$ alkyl); $X^1$ is —Br, —Cl, or —I.

In a further embodiment, the present invention relates to a composition, which is useful for the synthesis of compounds according to Formula I (including e.g. Compound (7)) comprising a compound of formula (5)

(5)

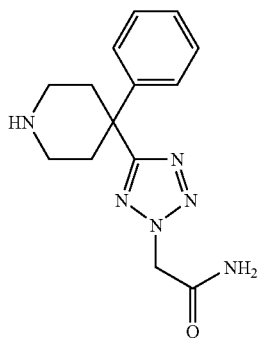

and a compound of formula (6)

(6)

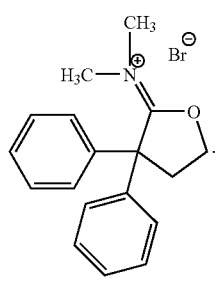

In another embodiment, the present invention is directed toward a composition, which is useful for synthesizing compounds according to Formula I (including e.g. Compound (7)), comprising sodium azide; a zinc salt; and a compound of formula (8)

(8)

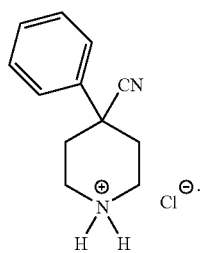

In a further embodiment, the present invention is directed toward a composition, which is useful for synthesizing compounds according to Formula I (including e.g. Compound (7)), comprising a compound of formula (9)

(9)

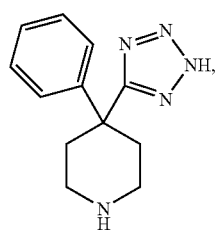

a compound of formula (6)

(6)

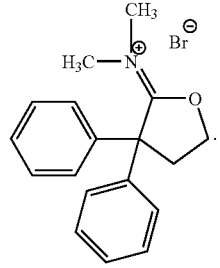

and a non-nucleophilic base.

In a further embodiment, the present invention is directed toward the use of a compound of formula (14)

(14)

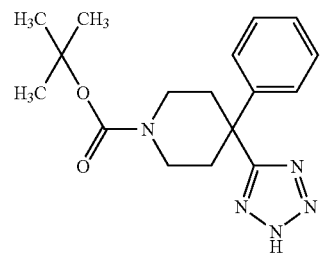

for synthesizing compounds according to Formula I such as, but not limited to, Compound (7).

In another embodiment, the present invention is directed toward a compound of formula (15)

(15)

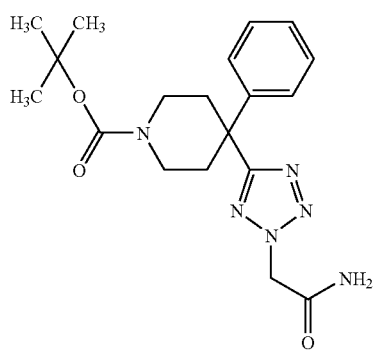

or a salt thereof, which is useful for synthesizing compounds according to Formula I such as, but not limited to, Compound (7).

In a further embodiment, the present invention is directed toward the use of a compound of formula (13)

(13)

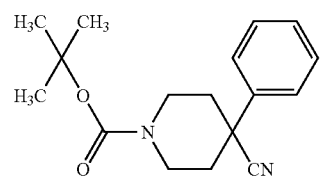

for synthesizing compounds according to Formula I such as, but not limited to, Compound (7).

In another embodiment, the present invention is directed toward the use of a compound of formula (18)

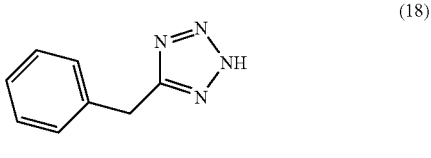
(18)

or a salt thereof, for synthesizing compounds according to Formula I such as, but not limited to, Compound (7).

In another embodiment, the present invention is directed toward a compound of formula (20)

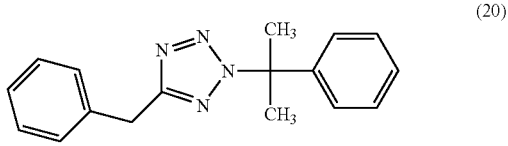
(20)

or a salt thereof, which is useful for synthesizing compounds according to Formula I such as, but not limited to, Compound (7).

In another embodiment, the present invention is directed toward a compound of formula (22)

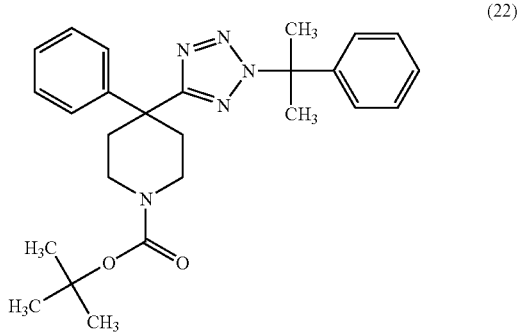
(22)

or a salt thereof, which is useful for synthesizing compounds according to Formula I such as, but not limited to, Compound (7).

In another embodiment, the present invention is directed toward a compound of formula (24)

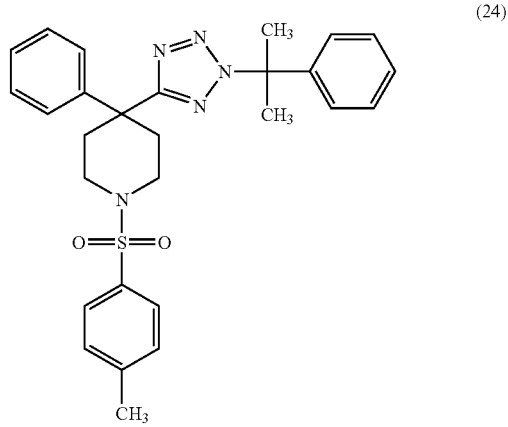
(24)

or a salt thereof, which is useful for synthesizing compounds according to Formula I such as, but not limited to, Compound (7).

In another embodiment, the present invention is directed toward a compound of formula (25)

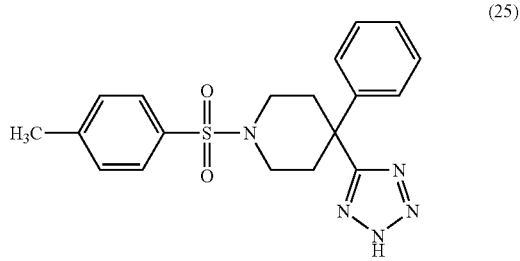
(25)

or a salt thereof, which is useful for synthesizing compounds according to Formula I such as, but not limited to, Compound (7).

In another embodiment, the present invention is directed toward a compound of formula (26)

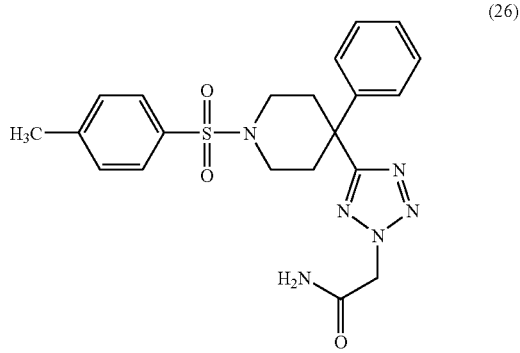
(26)

or a salt thereof, which is useful for synthesizing compounds according to Formula I such as, but not limited to, Compound (7).

In a still further embodiment, the present invention relates to a method for making a compound of formula (2)

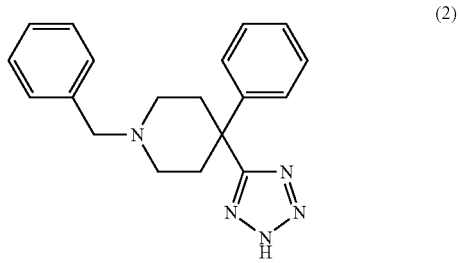
(2)

which comprises allowing a compound of formula (1)

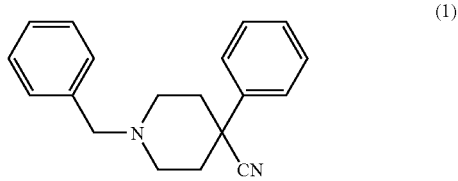
(1)

to react with sodium azide in the presence of a zinc salt in a solvent comprising a polar aprotic solvent to provide the compound of formula (2).

In another embodiment, the invention is directed toward a method for making a compound of formula (4)

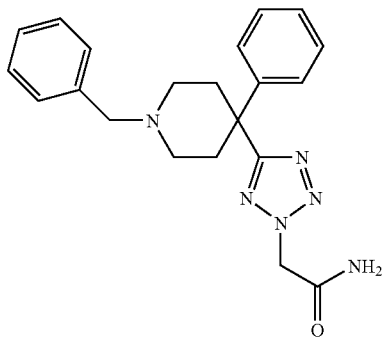
(4)

comprising allowing a compound of formula (2)

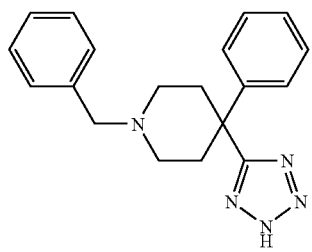
(2)

to react with a compound of Formula IX

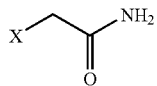
Formula IX where X is a halogen, such as, but not limited to, Br and Cl, to provide the compound of formula (4).

In still another embodiment, the invention is directed toward a method for making Compound (7)

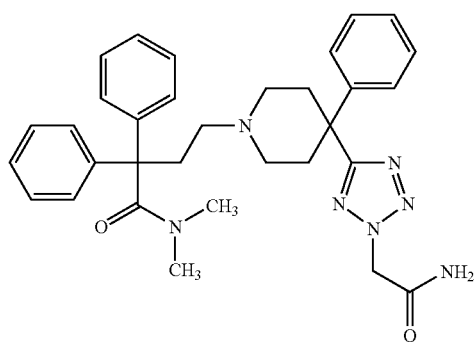
(7)

comprising allowing a compound of formula (5)

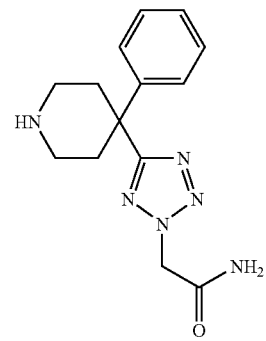
(5)

to react with a compound of formula (6)

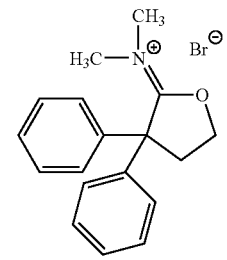
(6)

in the presence of a nucleophilic or a non-nucleophilic base in a solvent comprising a polar aprotic solvent.

In another embodiment, the present invention is directed toward a method for making Compound (7)

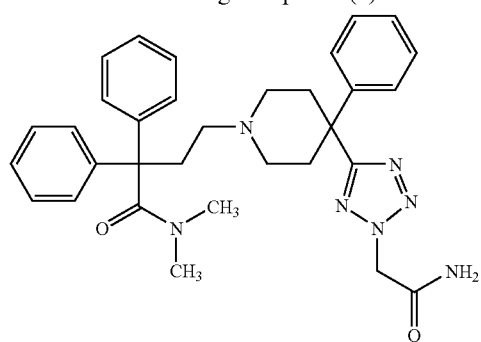

comprising:
(a) debenyzlating a compound of formula (4)

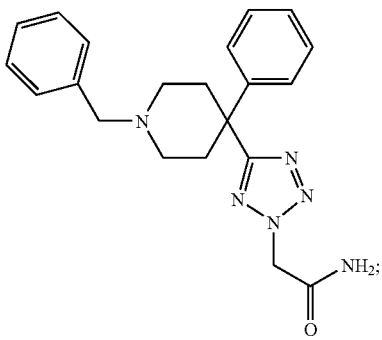
(4)

in the presence of hydrogen gas and a precious-metal catalyst to provide a compound of formula (5)

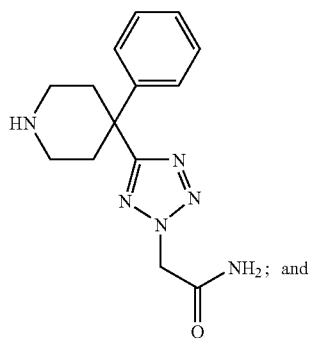
(5)

(b) allowing the compound of formula (5) to react with a compound of formula (6)

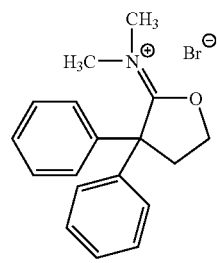
(6)

in the presence of a nucleophilic or a non-nucleophilic base, whereby Compound (7)

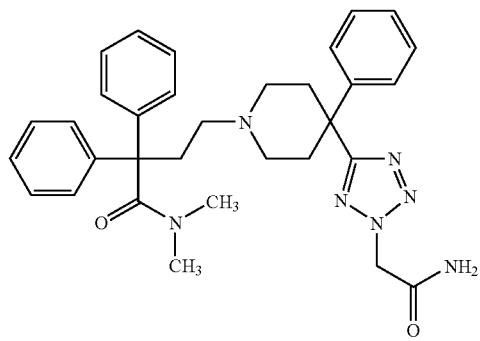
(7)

is formed.

In another embodiment, the present invention is directed toward a method for making Compound (7)

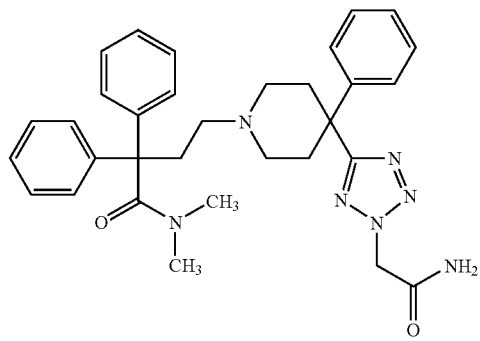
(7)

comprising allowing a compound of formula (2)

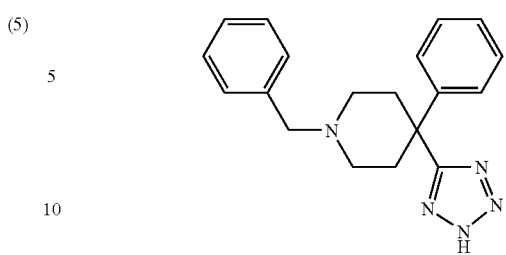
(2)

to react with a compound of Formula IX

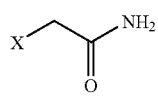
Formula IX where X is a halogen, such as, but not limited to, Br and Cl, in a solvent comprising a polar aprotic solvent in the presence of a non-nucleophilic base, to provide a compound of formula (4)

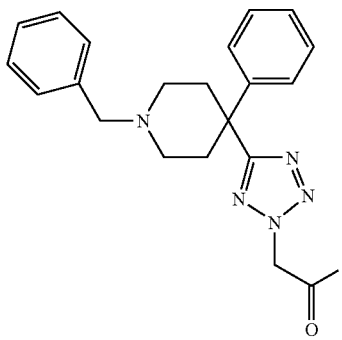
(4)

debenyzlating the compound of formula (4) in the presence of hydrogen gas and a precious-metal catalyst to provide a compound of formula (5)

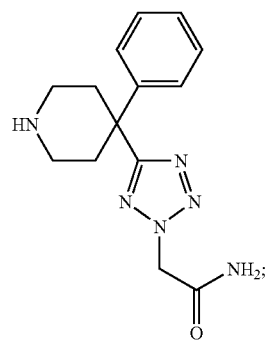
(5)

and then converting the compound of formula (5) to Compound (7).

In yet another embodiment, the present invention is directed toward a method for making Compound (7)

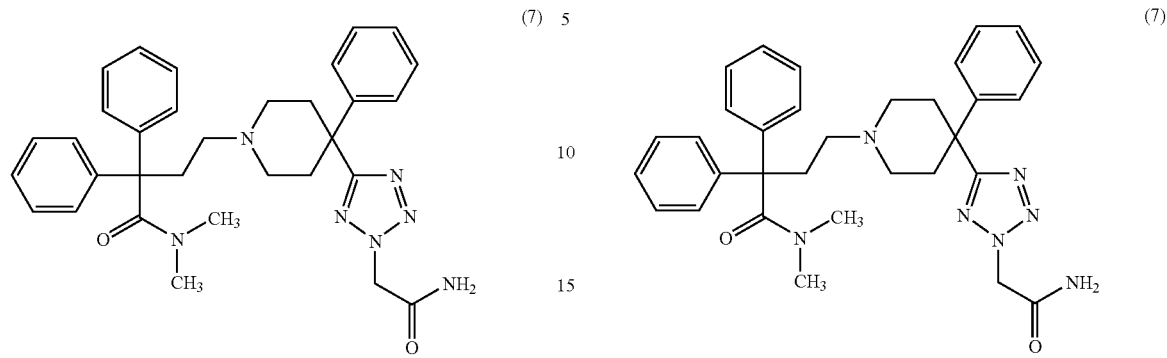
(7)

which comprises allowing a compound of formula (2)

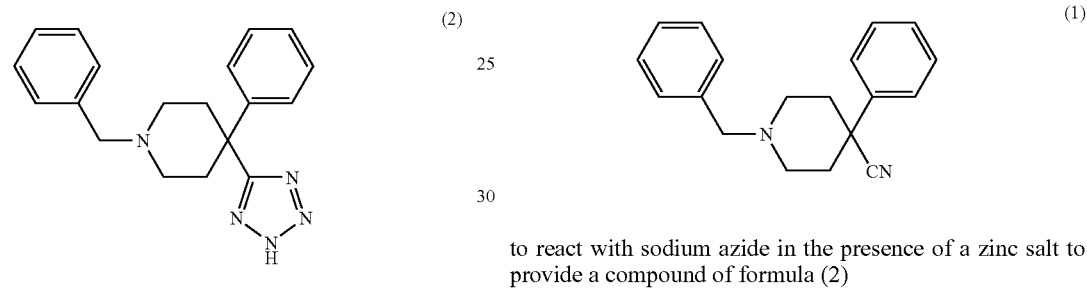
(2)

to react with a compound of Formula IX

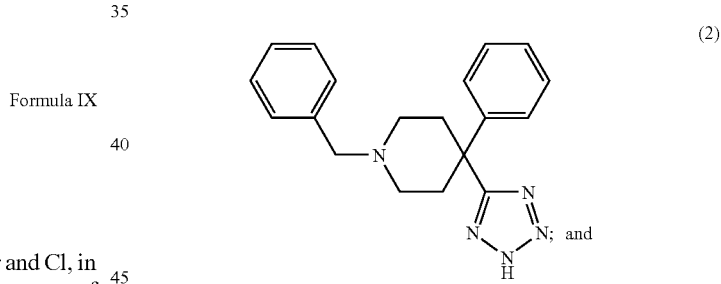
Formula IX where X is a halogen, such as, but not limited to, Br and Cl, in a solvent comprising a polar aprotic solvent in the presence of a non-nucleophilic base, to provide a compound of formula (4)

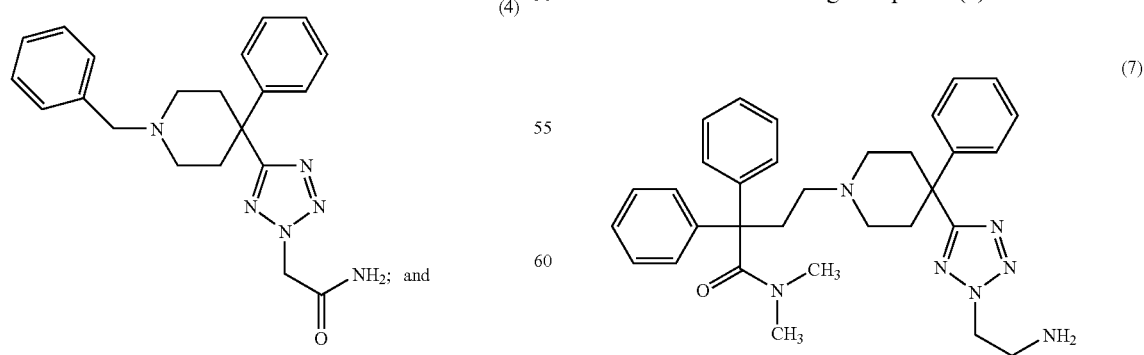
(4)

and then converting the compound of formula (4) to Compound (7)

The present invention is also directed, in another embodiment, to a method for making Compound (7)

(7)

comprising (a) allowing a compound of formula (1)

(1)

to react with sodium azide in the presence of a zinc salt to provide a compound of formula (2)

(2)

(b) converting the compound of formula (2) to Compound (7).

In another embodiment, the present invention is directed toward a method for making Compound (7)

(7)

comprising (a) allowing a compound of formula (1)

(1)

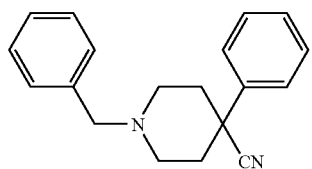

to react with sodium azide in the presence of a zinc salt to provide a compound of formula (2)

(2)

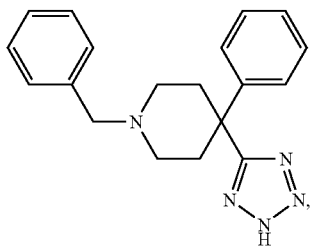

which is then alkylated with a compound of Formula IX

Formula IX

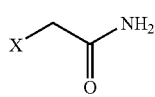

where X is a halogen, such as, but not limited to, Br and Cl, in the presence of a non-nucleophilic base to provide a compound of formula (4)

(4)

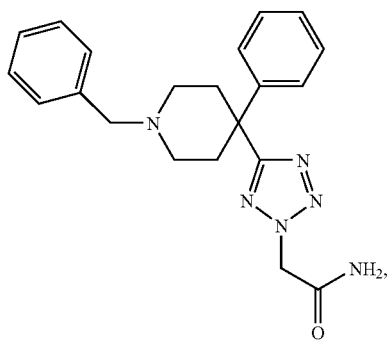

which is then debenzylated in the presence of hydrogen gas and a precious-metal catalyst to provide a compound of formula (5)

(5)

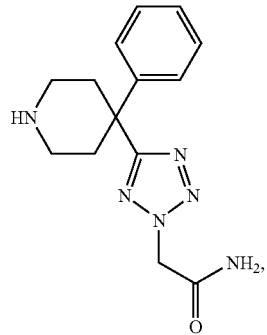

which is allowed to react with a compound of formula (6)

(6)

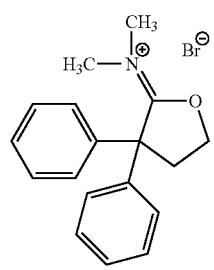

in the presence of a nucleophilic or a non-nucleophilic base, to provide Compound (7)

(7)

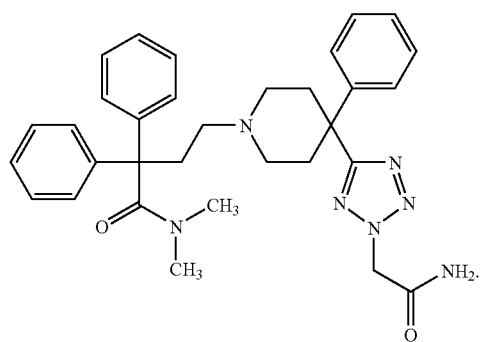

In another embodiment, the present invention is directed toward a method for making Compound (7)

(7)

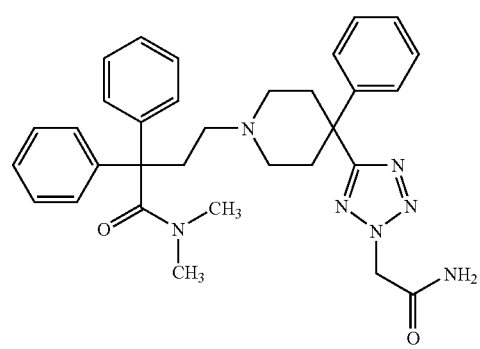

comprising (a) allowing a compound of formula (8)

(8)

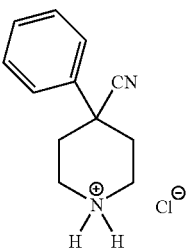

to react with sodium azide in the presence of a zinc salt such as but not limited to Zn(Br)₂ in a solvent comprising a polar aprotic solvent to provide a compound of formula (9)

(9)

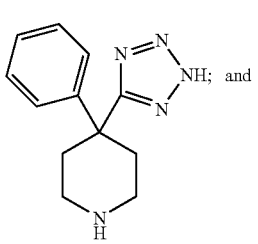

NH; and (b) converting the compound of formula (9) to Compound (7).

In certain embodiments, the polar aprotic solvent is selected from the group consisting of dioxane, N-methyl-pyrrolidone, dimethyl formamide, dimethyl acetamide, acetonitrile, dimethyl sulfoxide, and combinations thereof. In other embodiments, the solvent comprises a mixture the suitable polar aprotic solvent and water. In such embodiments the ratio of water to polar aprotic solvent can be within the range of from about 10:1 to about 1:1 (water:polar aprotic solvent). In certain embodiments, the polar aprotic solvent is dioxane. In another specific embodiment, the polar aprotic solvent is acetonitrile.

In another embodiment, the present invention is directed toward a method for making Compound (7)

(7)

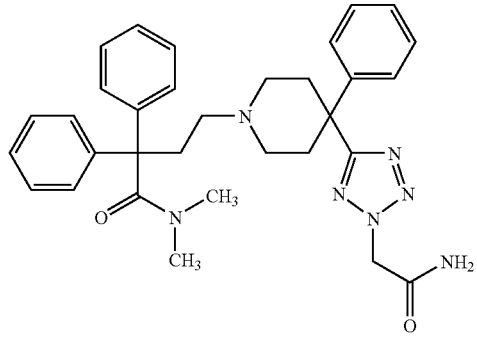

comprising (a) allowing a compound of formula (9)

(9)

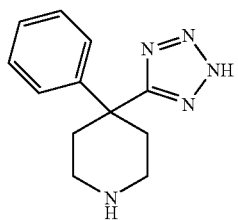

to react with a compound of formula (6)

(6)

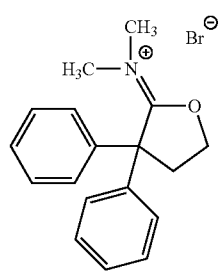

in a solvent comprising a polar aprotic solvent in the presence of a non-nucleophilic base, to provide a compound of formula (10)

(10)

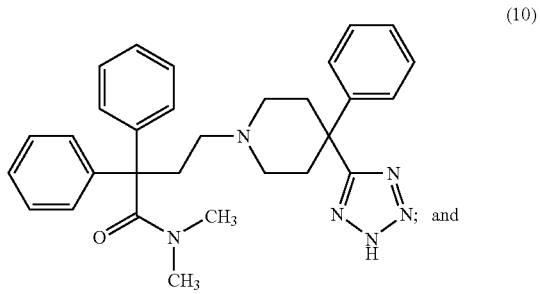

; and (b) converting the compound of formula (10) to Compound (7).

In another embodiment, the present invention is directed toward a method for making Compound (7)

(7)

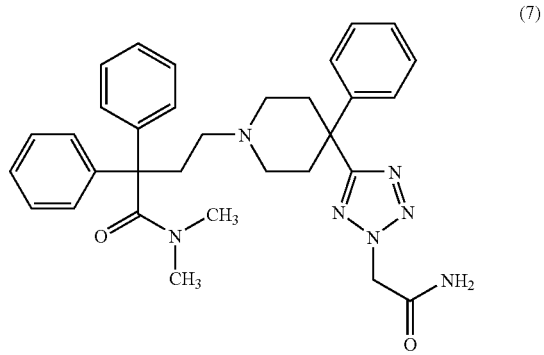

comprising (a) allowing a compound of formula (8)

(8)

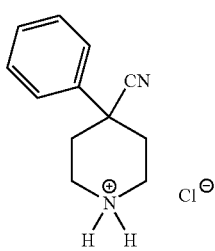

to react with sodium azide in the presence of a zinc salt in a solvent comprising a polar aprotic solvent to provide a compound of formula (9)

(9)

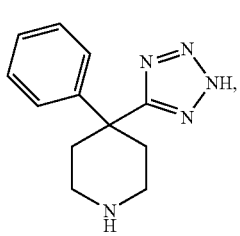

(b) reacting the compound of formula (9) with a compound of formula (6)

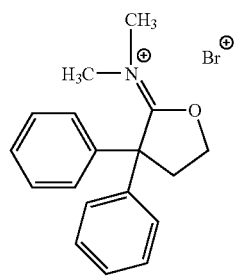

in the presence of a non-nucleophilic base to provide a compound of formula (10)

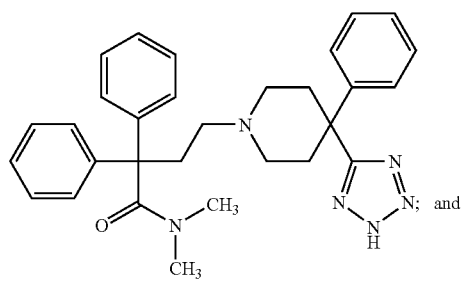

(c) alkylating the compound of formula (10) with a compound of Formula IX

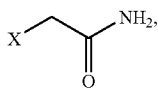

where X is a halogen, such as, but not limited to, Br and Cl, to provide Compound (7)

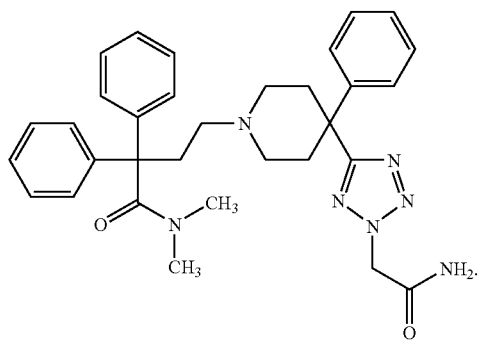

In certain embodiments, the polar aprotic solvent is selected from the group consisting of dioxane, N-methylpyrrolidone, dimethyl formamide, dimethyl acetamide, dimethyl sulfoxide, acetonitrile, and combinations thereof. In other embodiments, the solvent comprises a mixture the suitable polar aprotic solvent and water. In such embodiments the ratio of water to polar aprotic solvent can be within the range of from about 10:1 to about 1:1 (water:polar aprotic solvent).

In certain embodiments, the polar aprotic solvent is dioxane. In other embodiments, the polar aprotic solvent can be acetonitrile.

In a further embodiment, the present invention is directed toward a method for making Compound (7)

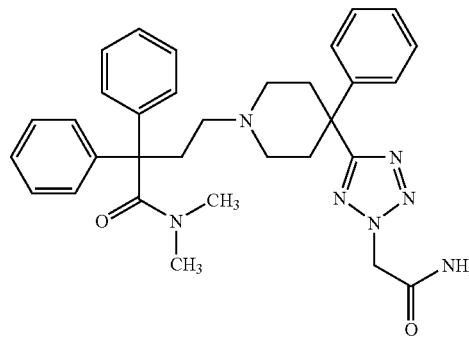

comprising: (a) allowing a compound of formula (2)

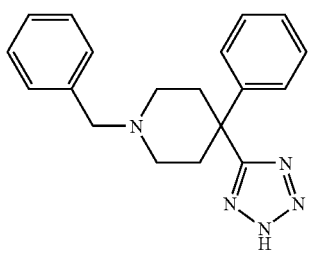

to react with a compound of Formula IX

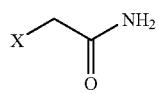

where X is a halogen, such as, but not limited to, Br and Cl, in the presence of a non-nucleophilic base to provide a compound of formula (4)

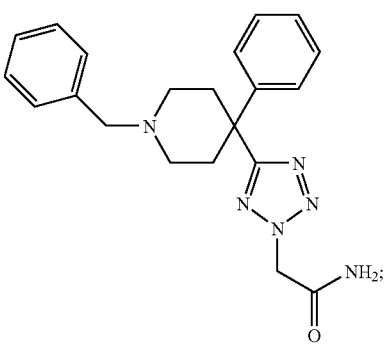

(b) debenzylating the compound of formula (4) in the presence of hydrogen gas and a precious-metal catalyst to provide a compound of formula (5)

(5)

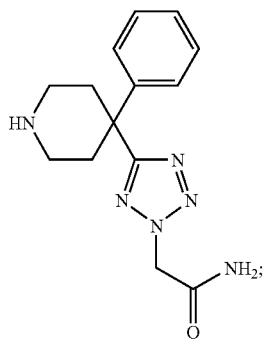

and (c) allowing the compound of formula (5) to react with a compound of formula (6)

(6)

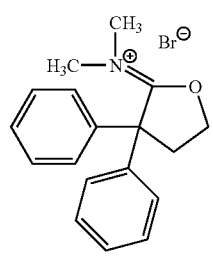

in the presence of a non-nucleophilic base or a nucleophilic base, whereby Compound (7)

(7)

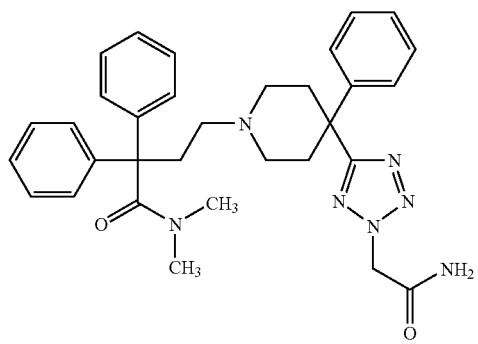

is formed.

In a still further embodiment, the present invention is directed toward a method for making Compound (7)

(7)

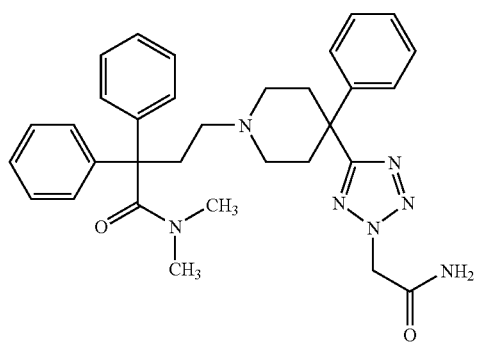

comprising (a) allowing a compound of formula (10)

(10)

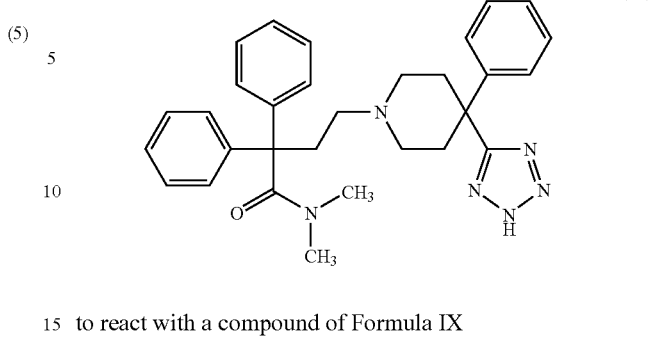

to react with a compound of Formula IX

Formula IX

where X is a halogen, such as, but not limited to, Br and Cl, whereby Compound (7)

(7)

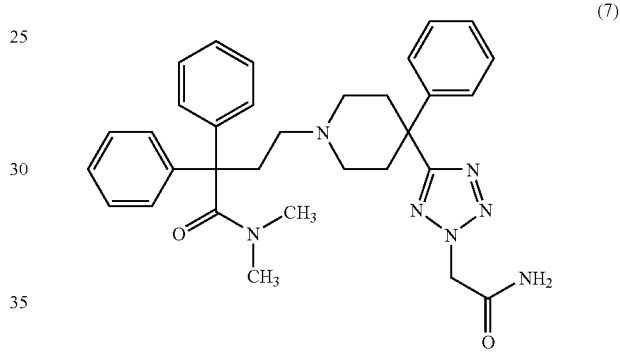

is formed.

In another embodiment, the present invention is directed toward a method for making Compound (7)

(7)

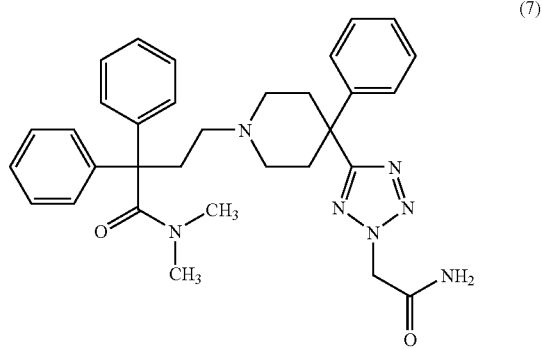

comprising: (a) allowing a compound of formula (9)

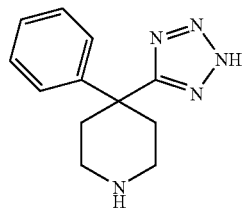

to react with a compound of formula (6)

(6)
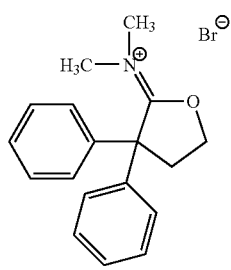

in the presence of a non-nucleophilic base to provide a compound of formula (10)

(10)
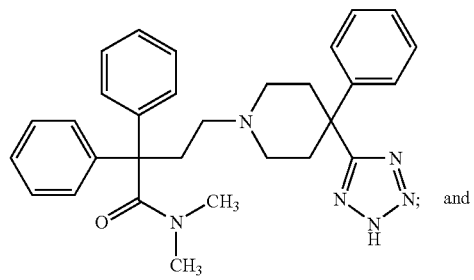
and (b) allowing the compound of formula (10) to react with a compound of Formula IX Formula IX
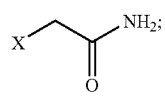

where X is a halogen, such as, but not limited to, Br and Cl, whereby Compound (7) is formed.

In a further embodiment, the present invention is directed toward a method for making a compound of formula (5)

(5)
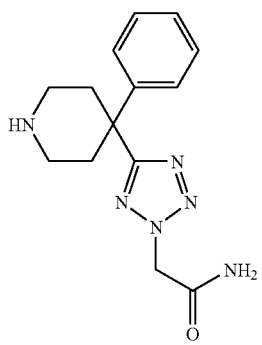

comprising: (a) allowing a compound of formula (2)

(2)
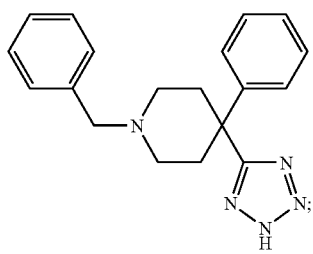

to react with a compound of Formula IX

Formula IX
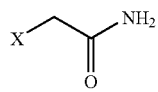

where X is a halogen, such as, but not limited to, Br and Cl, in the presence of a non-nucleophilic base to provide a compound of formula (4)

(4)
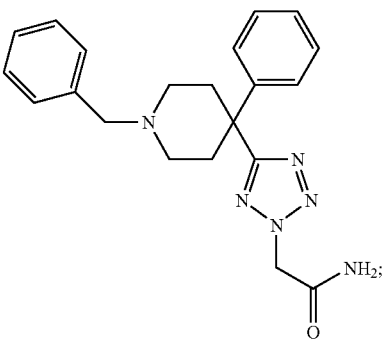

and then debenzylating the compound of formula (4) in the presence of hydrogen gas and a precious-metal catalyst to provide the compound of formula (5).

In a still further embodiment, the present invention is directed toward a method for making a compound according to formula (5)

(5)
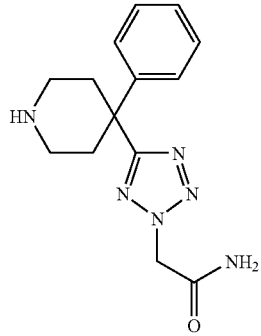

comprising allowing a compound of formula (1)

(1)
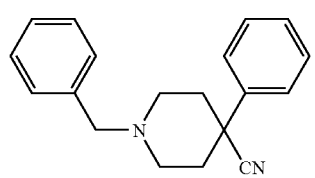

to react with sodium azide in the presence of a zinc salt to provide a compound of formula (2)

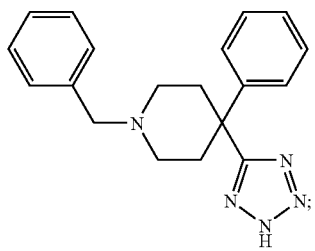
(2)

allowing the compound of formula (2) to react with a compound of Formula IX

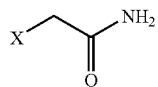
Formula IX where X is a halogen, such as, but not limited to, Br and Cl, in the presence of a non-nucleophilic base to provide a compound of formula (4)

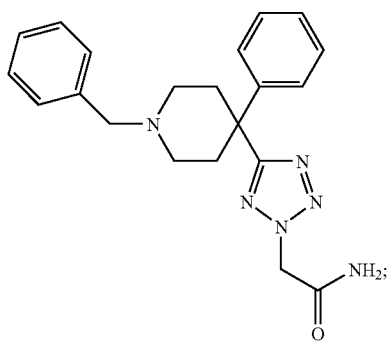
(4)

and then debenzylating the compound of formula (4) in the presence of hydrogen gas and a precious-metal catalyst to provide the compound of formula (5).

In another embodiment, the present invention is directed toward a method for making a compound according to formula (9)

(9)

comprising debenzylating a compound of formula (2)

(2)

in the presence of hydrogen gas and a precious-metal catalyst to provide the compound of formula (9).

In a further embodiment, the present invention is directed toward a method for making a compound according to formula (9)

(9)

comprising allowing a compound of formula (1)

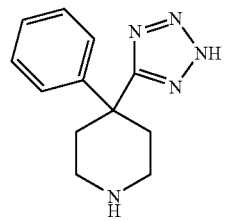
(1)

to react with sodium azide in the presence of a zinc salt in a solvent comprising a polar aprotic solvent, to provide a compound of formula (2)

(2)

and debenzylating the compound of formula (2) in the presence of hydrogen gas and a precious-metal catalyst to provide the compound of formula (9).

In a still further embodiment, the present invention is directed toward a method for making a compound according to formula (9)

(9)

comprising allowing a compound of formula (8)

(8)

to react with sodium azide and a zinc salt in a solvent comprising a polar aprotic solvent, thereby providing the compound of formula (9). In one aspect of this embodiment, the solvent comprises a mixture of dioxane and water.

In a further embodiment, the present invention is directed toward a method for making a compound of formula (4)

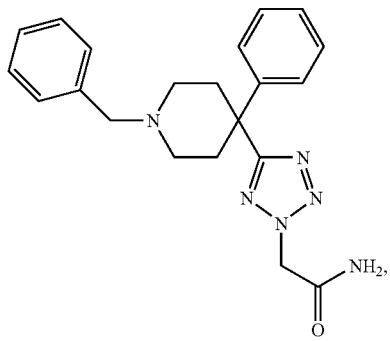

(4)

comprising allowing a compound of formula (1)

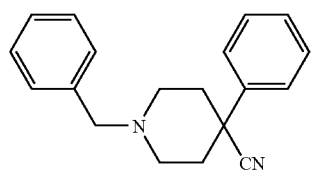

(1)

to react with sodium azide in the presence of a zinc salt, to provide a compound of formula (2)

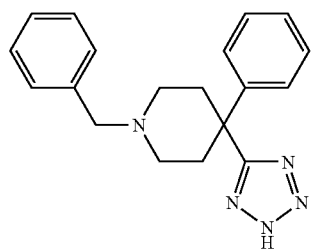

(2)

and allowing the compound of formula (2) to react with a compound of Formula IX,

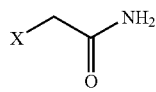

Formula IX wherein X is selected from the group consisting of Br, Cl, or I, in the presence of a non-nucleophilic base in a solvent comprising a polar aprotic solvent, to produce compound (4).

In a further embodiment, the present invention is directed toward a method for making a compound of formula (5)

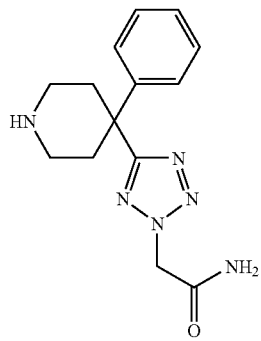

(5)

comprising debenzylating a compound of formula (4)

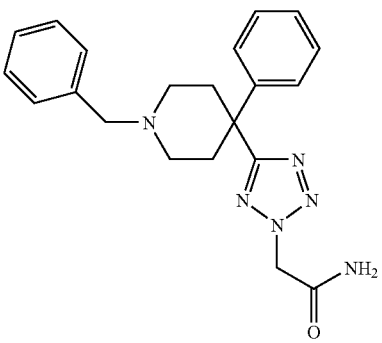

(4)

in the presence of hydrogen gas and a precious-metal catalyst to provide the compound of formula (5).

In another embodiment, the present invention is directed toward a compound of formula (20)

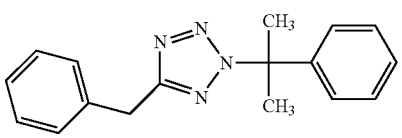

(20)

or a salt thereof, which is useful for synthesizing compounds according to Formula I such as, but not limited to Compound (7).

In a further embodiment, the present invention is directed toward a compound of formula (25)

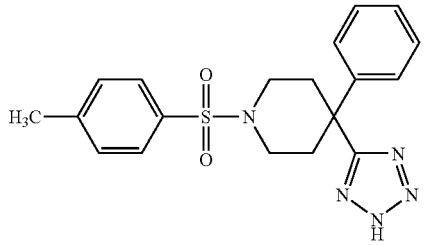

(25)

or a salt thereof, which is useful for synthesizing compounds according to Formula I such as, but not limited to Compound (7).

In another embodiment, the present invention is directed toward a compound of Formula XII

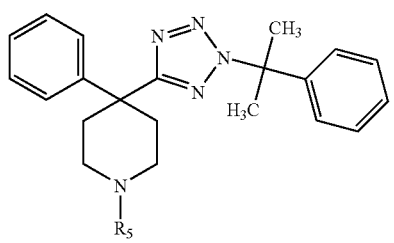

XII or a salt thereof, wherein $R^5$ is selected from the group consisting of

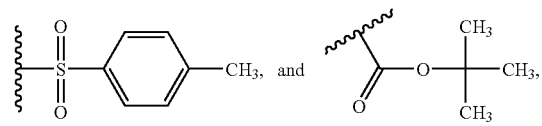

which is useful for synthesizing compounds according to Formula I such as, but not limited to Compound (7).

In a still further embodiment, the present invention is directed toward a compound of Formula XIV

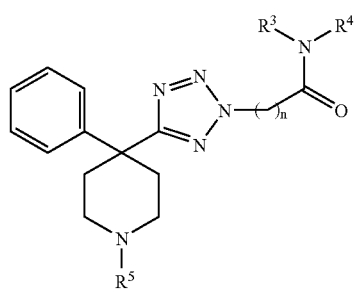

XIV or a salt thereof, wherein n is an integer ranging from 1 to 4, $R^3$ and $R^4$ are each independently hydrogen or —($C_1$-$C_4$ alkyl), and $R^5$ is selected from the group consisting of

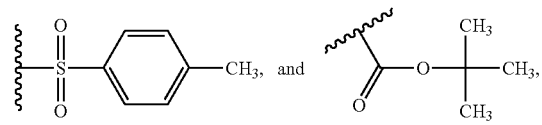

which is useful for synthesizing compounds according to Formula I such as, but not limited to Compound (7). In a specific aspect of this embodiment, the compound of Formula XIV is one in which n is 1, $R^3$ and $R^4$ are both hydrogen, and $R^5$ is

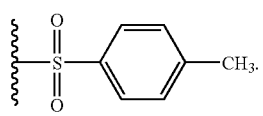

In another specific aspect of this embodiment, the compound of Formula XIV is one in which n is 1, $R^3$ and $R^4$ are both hydrogen, and $R^5$ is

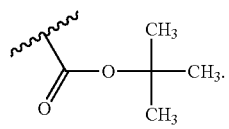

In a further embodiment, the present invention is directed toward a method for making a compound of formula (15)

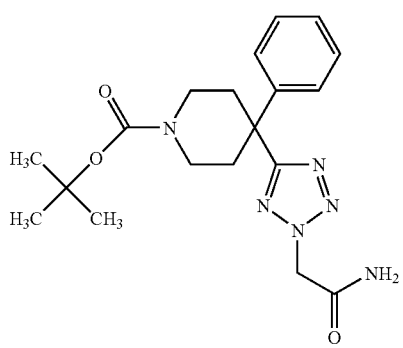

(15)

comprising allowing a compound of formula (14),

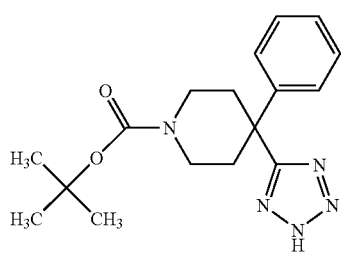

(14)

to react with a compound of Formula IX

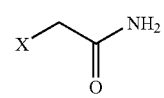

IX wherein X is selected from the group consisting of Br, Cl, or I, in the presence of a non-nucleophilic base to produce compound (15).

In another embodiment, the present invention is directed toward a method for making a compound of formula (15), comprising allowing compound (20)

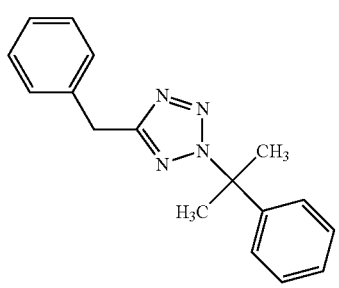

(20)

to react with compound (21)

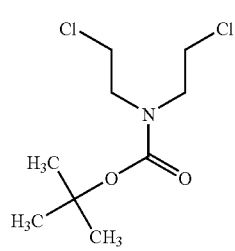

(21)

to produce a compound of formula (22),

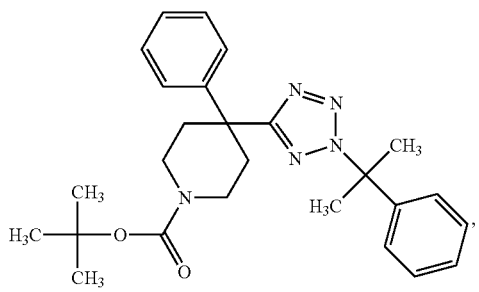
(22)

deprotecting compound (22) in ethanol, in the presence of potassium formate and Pd/C, to provide a compound of formula (14)

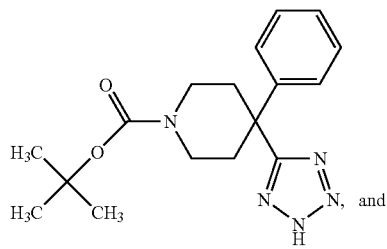
(14)

allowing the compound of formula (14), to react with a compound of Formula IX

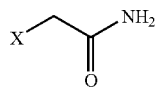
IX wherein X is selected from the group consisting of Br, Cl, or I, in the presence of a non-nucleophilic base to produce compound (15).

The present invention is also directed, in another embodiment, toward a method for making a compound of formula (15), comprising allowing a compound of formula (8),

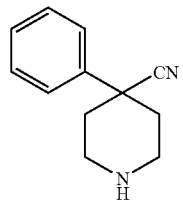
(8)

to react with sodium azide in the presence of a zinc salt to produce a compound of formula (9),

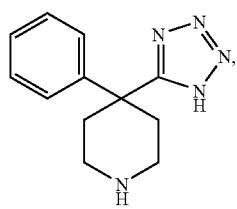
(9)

allowing the compound of formula (9) to react with a compound of formula (12),

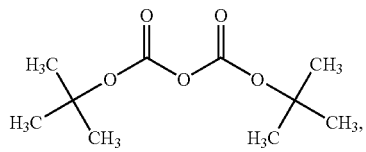
(12)

to produce a compound of formula (14),

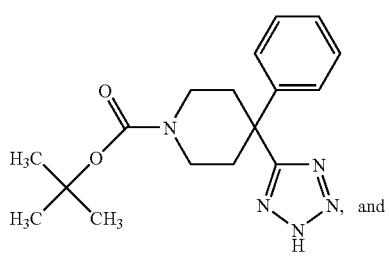
(14)

allowing the compound of formula (14) to react with a compound of Formula IX

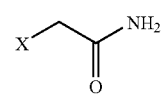
IX wherein X is selected from the group consisting of Br, Cl, or I, in the presence of a non-nucleophilic base to produce compound (15).

In another embodiment, the present invention is directed toward a method for making a compound of formula (26)

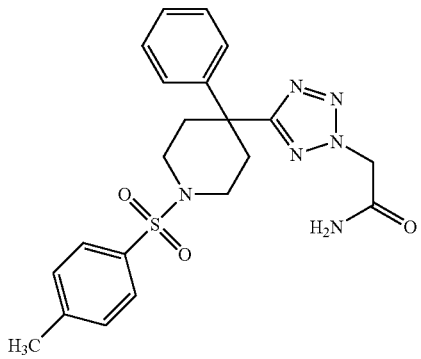
(26)

comprising allowing a compound of formula (25),

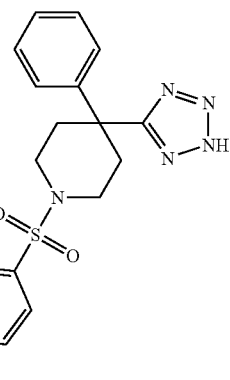
(25)

to react with a compound of Formula IX

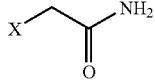

wherein X is selected from the group consisting of Br, Cl, or I, in the presence of a non-nucleophilic base to produce compound (26).

In a further embodiment, the present invention is directed toward a method for making a compound of formula (26)

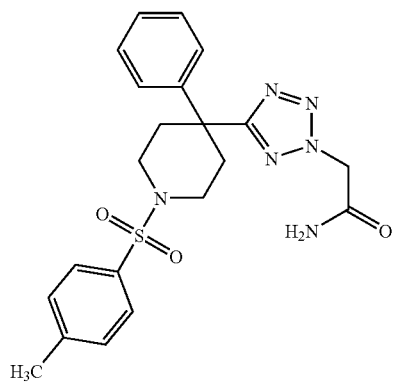

comprising allowing a compound of formula (20)

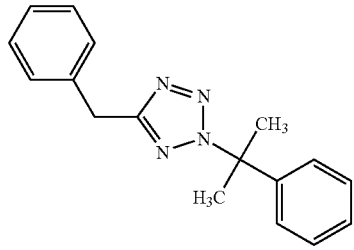

to react with a compound of formula (23)

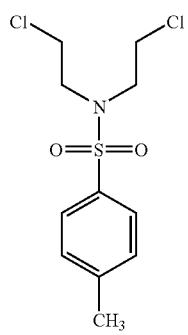

to produce a compound of formula (24),

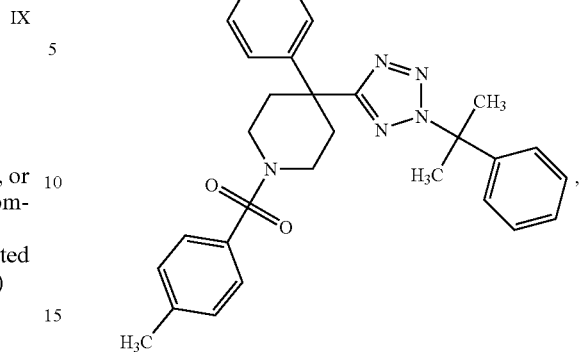

deprotecting compound (24) in ethanol, in the presence of potassium formate and Pd/C, to provide a compound of formula (25)

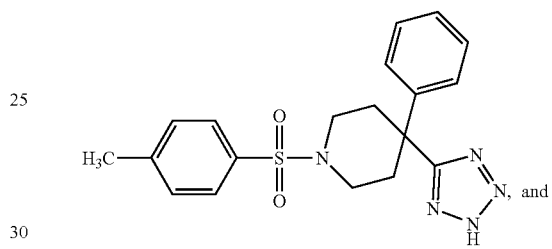

allowing the compound of formula (25) to react with a compound of Formula IX

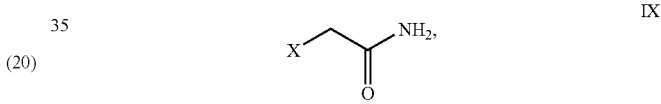

wherein X is selected from the group consisting of Br, Cl, or I, in the presence of a non-nucleophilic base to produce compound (26).

In a still further embodiment, the present invention is directed toward a method for making a compound of formula (20), comprising allowing a compound of formula (18),

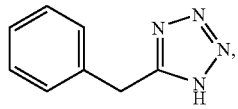

to react with a compound of formula (19),

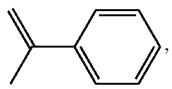

to produce the compound of formula (20).

In yet another embodiment, the present invention is directed toward a method for making a compound of formula (20), comprising allowing a compound of formula (17),

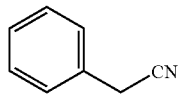

to react with sodium azide in the presence of a zinc salt to provide a compound of formula (18),

(18)
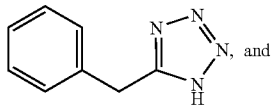

allowing the compound of formula (18) to react with a compound of formula (19),

(19)
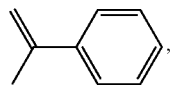

to produce the compound of formula (20).

In another embodiment, the present invention is directed toward a method for making a compound of formula (25),

(25)
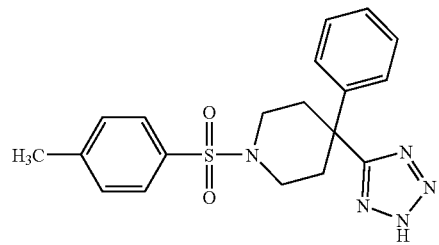

comprising allowing a compound of formula (20),

(20)
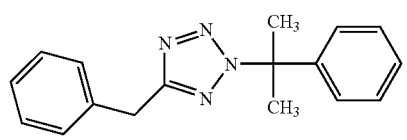

to react with a compound of formula (23),

(23)
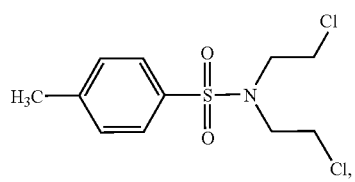

to produce a compound of formula (24),

(24)
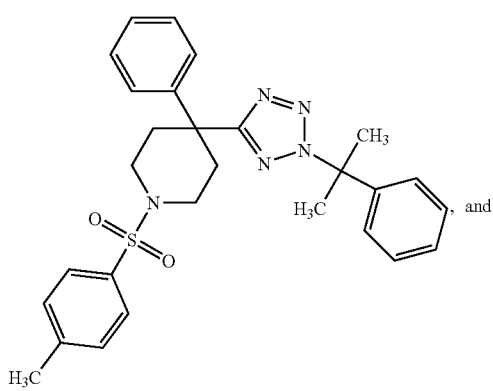

deprotecting the compound of formula (24) in ethanol, in the presence of potassium formate and Pd/C, to produce the compound of formula (25).

In a still further embodiment, the present invention is directed toward a method for making compound (7)

(7)
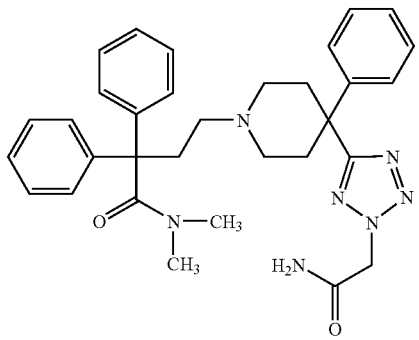

comprising deprotecting a compound of formula (15)

(15)
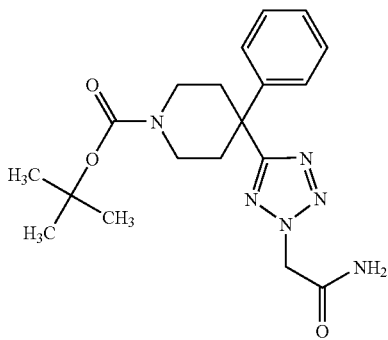

to produce a compound of formula (5), (5)
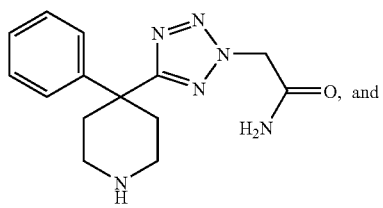

converting the compound of formula (5) to Compound (7).

In another embodiment, the present invention is directed toward a method for making compound (7)

(7)
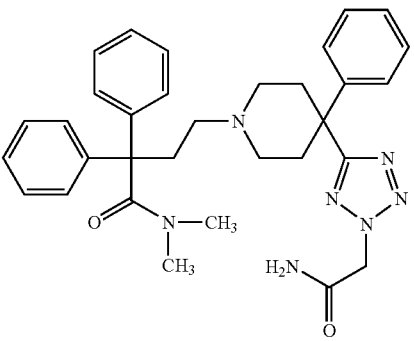

comprising deprotecting a compound of formula (26)

(26)
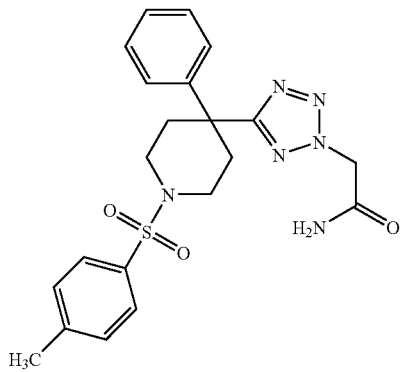

to produce a compound of formula (5), (5)
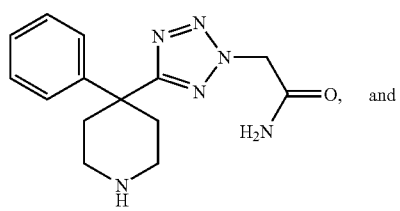

converting the compound of formula (5) to Compound (7).

In yet another embodiment, the present invention is directed toward a method for making compound (7)

(7)
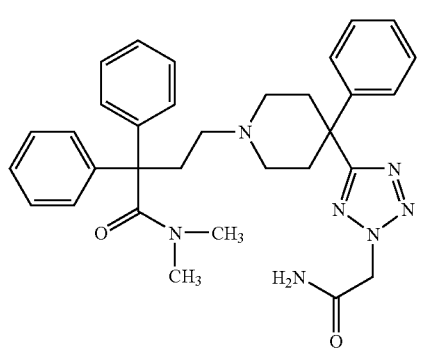

comprising allowing a compound of formula (14)

(14)
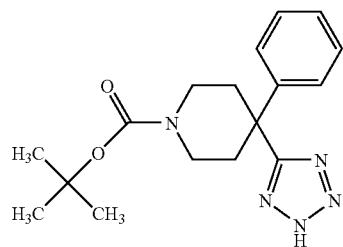

to react with a compound of Formula IX

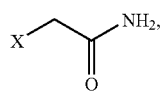
IX wherein X is selected from the group consisting of Br, Cl, or I, in the presence of a non-nucleophilic base to produce compound (15),

(15)
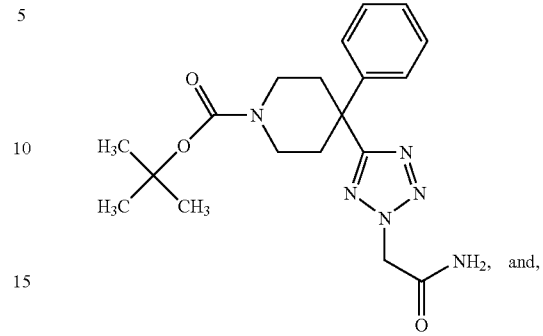

converting the compound of formula (15) to Compound (7).

In a still further embodiment, the present invention is directed toward a method for making compound (7)

(7)
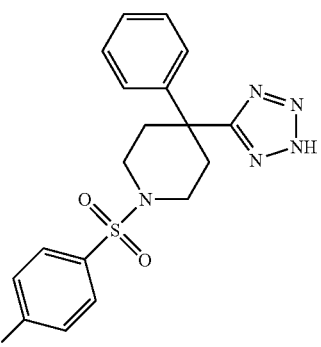

comprising allowing a compound of formula (25)

(25)

to react with a compound of Formula IX

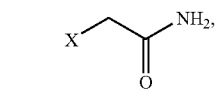
IX wherein X is selected from the group consisting of Br, Cl, or I, in the presence of a non-nucleophilic base to produce compound (26),

(26)
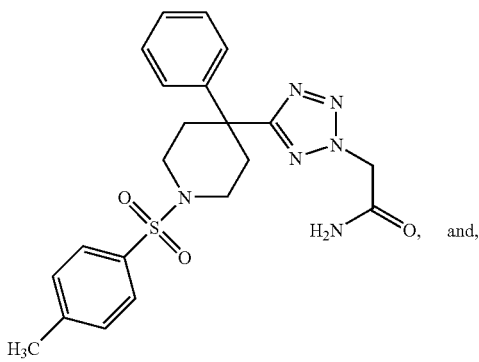

and, converting the compound of formula (26) to Compound (7).

In another embodiment, the present invention is directed toward a method for making compound (7)

(7)
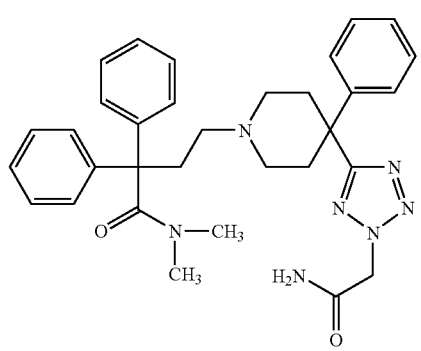

comprising deprotecting a compound of formula (22)

(22)
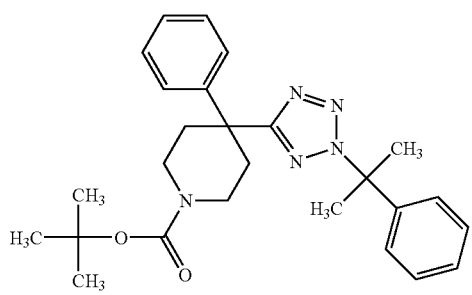

to produce a compound of formula (14), (14),
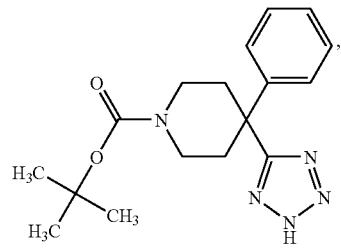

allowing the compound of formula (14) to react with a compound of Formula IX

IX
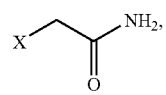

wherein X is selected from the group consisting of Br, Cl, or I, in the presence of a non-nucleophilic base to produce compound (15),

(15)
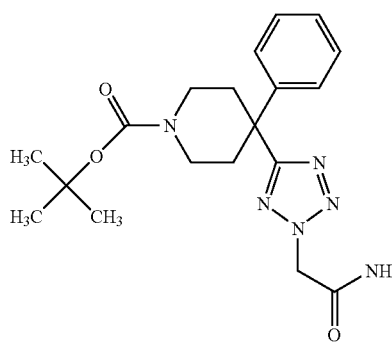

and converting the compound of formula (15) to Compound (7).

In a further embodiment, the present invention is directed toward a method for making compound (7)

(7)
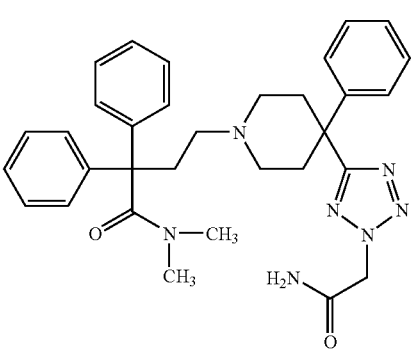

comprising deprotecting a compound of formula (24)

(24)
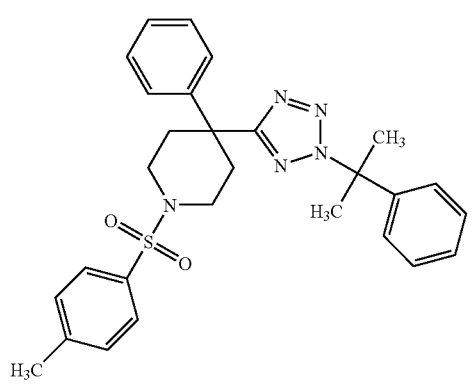

to produce a compound of formula (25),

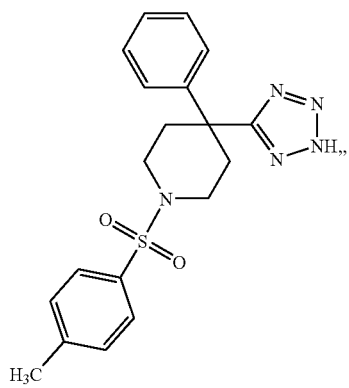
(25)

allowing the compound of formula (25) to react with a compound of Formula IX

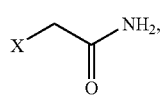
IX wherein X is selected from the group consisting of Br, Cl, or I, in the presence of a non-nucleophilic base to produce compound (26),

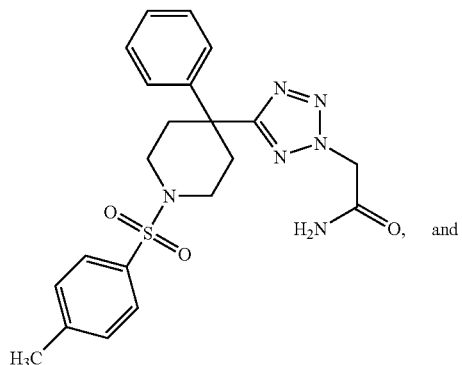
(26)

converting the compound of formula (26) to Compound (7).

In a still further embodiment, the present invention is directed toward a method for making compound (7)

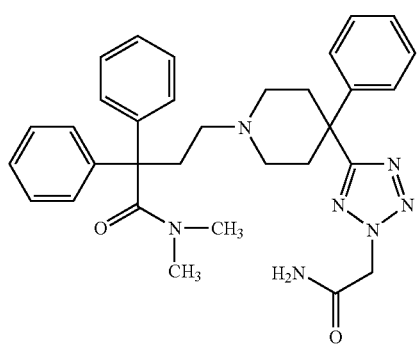

comprising allowing a compound of formula (20)

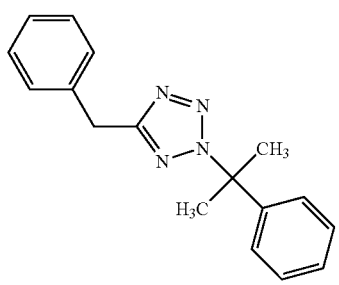
(20)

to react with a compound of formula (21)

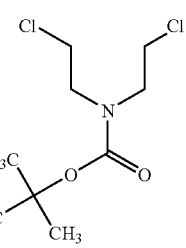
(21)

to produce a compound of formula (22),

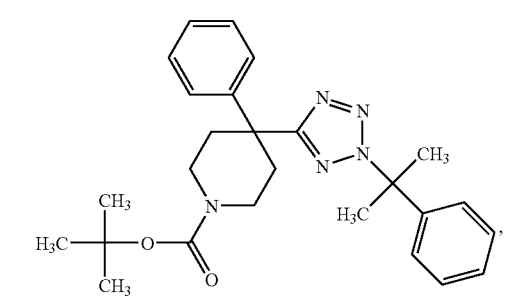
(22)

deprotecting the compound of formula (22) in ethanol, in the presence of potassium formate and Pd/C, to provide a compound of formula (14)

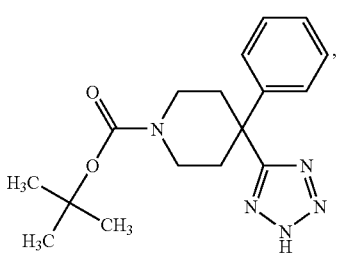
(14)

allowing the compound of formula (14), to react with a compound of Formula IX

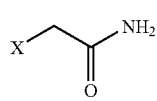
IX wherein X is selected from the group consisting of Br, Cl, or I, in the presence of a non-nucleophilic base to produce a compound of formula (15)

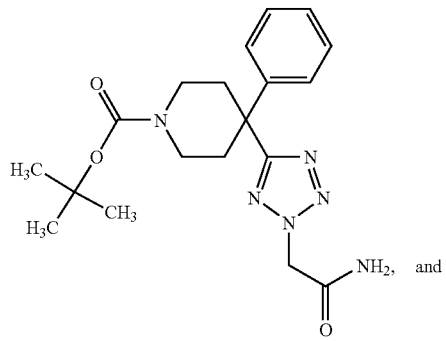

(15)

converting the compound of formula (15) to Compound (7).

In a still further embodiment, the present invention is directed toward a method for making compound (7)

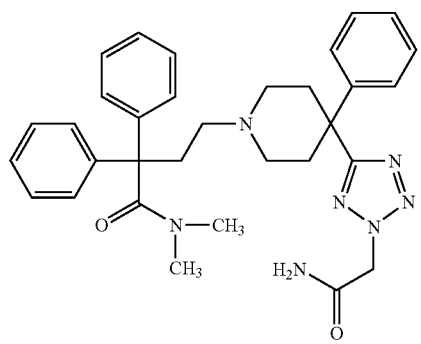

comprising allowing a compound of formula (20)

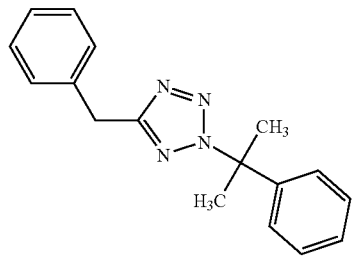

(20)

to react with a compound of formula (23)

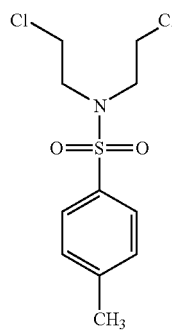

(23)

to produce a compound of formula (24),

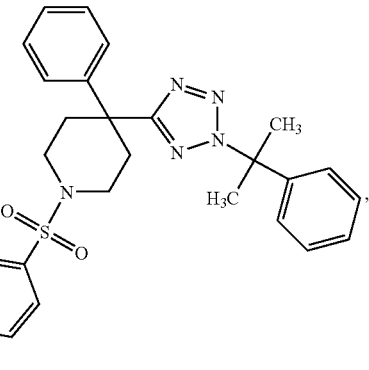

(24)

deprotecting compound (24) in ethanol, in the presence of potassium formate and Pd/C, to provide a compound of formula (25)

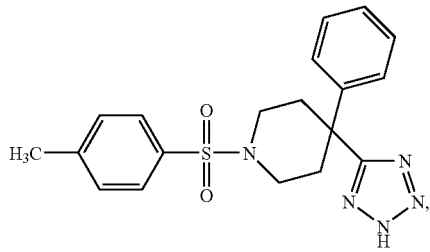

(25)

allowing the compound of formula (25) to react with a compound of Formula IX

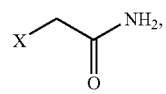

IX wherein X is selected from the group consisting of Br, Cl, or I, in the presence of a non-nucleophilic base to produce a compound of formula (26)

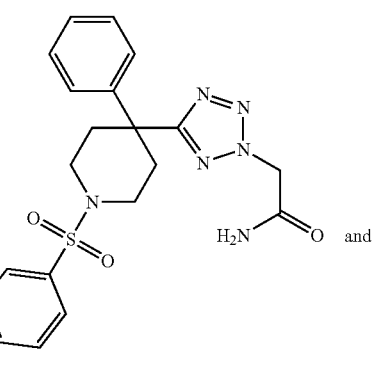

(26)

and converting the compound of formula (26) to Compound (7).

In another embodiment, the present invention is directed toward a method for making compound (7)

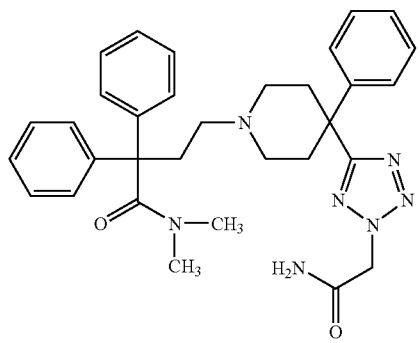

comprising allowing a compound of formula (9)

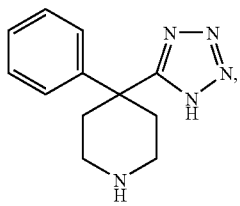

(9)

to react with a compound of formula (12),

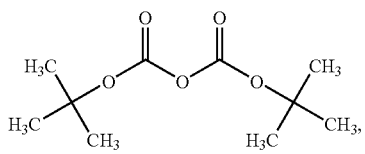

(12)

to produce a compound of formula (14),

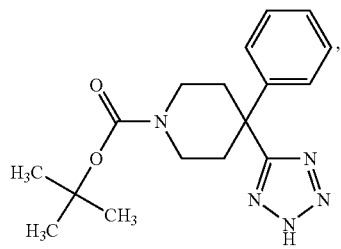

(14)

allowing the compound of formula (14), to react with a compound of Formula IX

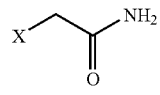

IX wherein X is selected from the group consisting of Br, Cl, or I, in the presence of a non-nucleophilic base to produce a compound of formula (15)

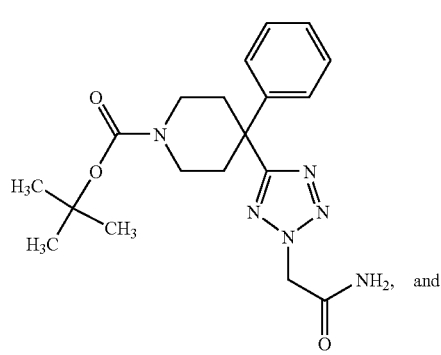

(15)

converting the compound of formula (15) to Compound (7).

In further embodiment, the present invention is directed toward a method for making compound (7)

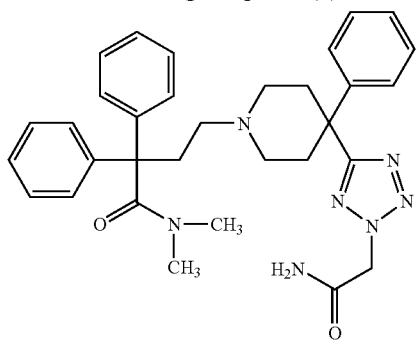

comprising allowing a compound of formula (9)

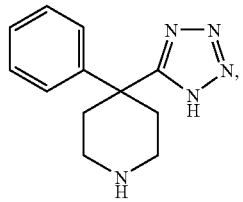

(9)

to react with a compound of formula (28),

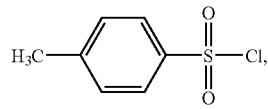

(28)

to produce a compound of formula (25),

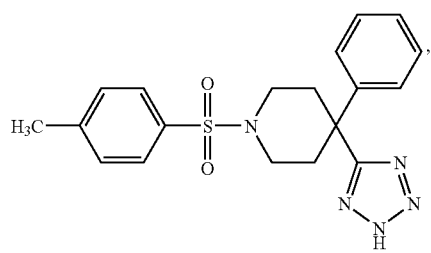

(25)

allowing the compound of formula (25), to react with a compound of Formula IX

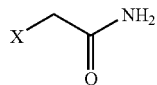
(IX)

wherein X is selected from the group consisting of Br, Cl, or I, in the presence of a non-nucleophilic base to produce a compound of formula (26)

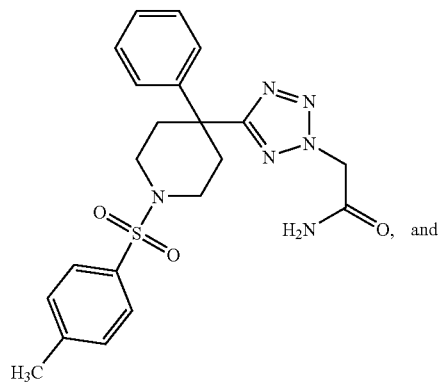
(26)

converting the compound of formula (26) to Compound (7).

In another embodiment, the present invention is directed toward a compound of formula (35)

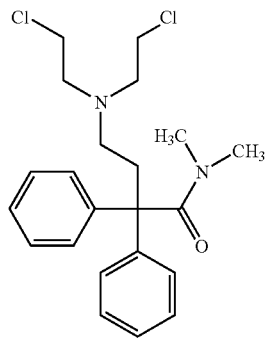
(35)

or a salt thereof, which is useful for synthesizing compounds according to Formula I such as, but not limited to, Compound (7).

In another embodiment, the present invention is directed toward a compound of formula (36)

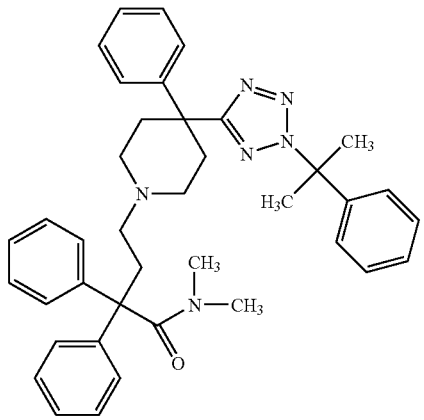
(36)

or a salt thereof, which is useful for synthesizing compounds according to Formula I such as, but not limited to, Compound (7).

In another embodiment, the present invention is directed toward a method for the synthesis of compound (7)

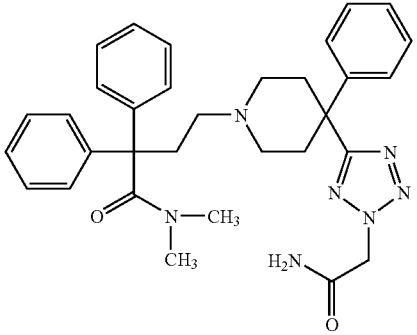

comprising allowing a compound of formula (20)

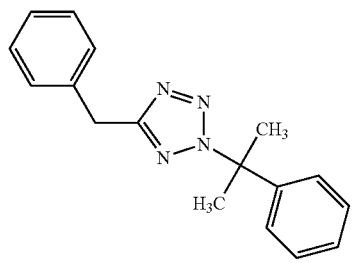
(20)

to react with a compound of formula (35)

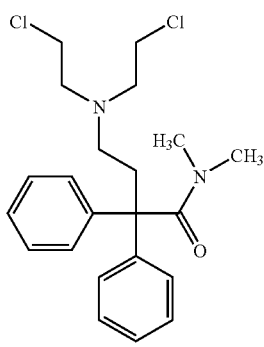
(35)

to produce a compound of formula (36),

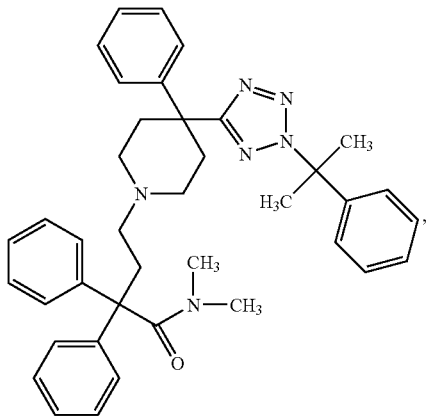
(36)

deprotecting the compound of formula (36) in ethanol, in the presence of potassium formate and Pd/C, to provide a compound of formula (10),

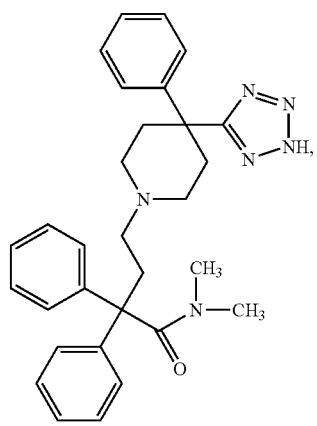

(10)

and converting the compound of formula (10) to Compound (7).

The present invention can be understood more fully by reference to the following detailed description and illustrative examples, which exemplify non-limiting embodiments of the invention.

4. DETAILED DESCRIPTION OF PREFERRED EMBODIMENTS OF THE INVENTION

4.1. Definitions

As used herein, the generic term "4-Tetrazolyl-4-phenylpiperidine Compound," refers to a compound that has the structure of Formula I:

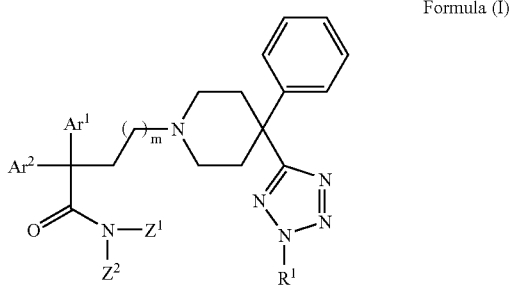

Formula (I)

wherein $Ar^1$ is —$C_3$-$C_8$ cycloalkyl, phenyl, naphthyl, anthryl, phenanthryl or -(5-7-membered) heteroaryl, each being unsubstituted or substituted with one or more $R^2$ groups;

$Ar^2$ is phenyl, naphthyl, anthryl, phenanthryl or -(5-7-membered) heteroaryl, each being unsubstituted or substituted with one or more $R^2$ groups;

$Z^1$ and $Z^2$ are each independently a —($C_1$-$C_4$ alkyl) group;

$R^1$ is —$(CH_2)_n$—$C(O)N(R^3)(R^4)$;

$R^3$ and $R^4$ are each independently H or —($C_1$-$C_4$ alkyl);

$R^2$ is halogen, —$C_1$-$C_3$ alkyl, —O—($C_1$-$C_3$ alkyl), —NH($C_1$-$C_3$ alkyl) or —N($C_1$-$C_3$ alkyl)$_2$;

n is an integer ranging from 1 to 4; and m is an integer ranging from 0 to 4.

In certain embodiments, the phenyl moiety attached to the 4-position of the piperidine ring of a compound according Formula I can be optionally substituted with one or more $R^2$ groups, where $R^2$ is as defined above.

The term "halide" refers to fluoride, chloride, bromide or iodide.

The term "-halo" means —F, —Cl, —Br or —I.

The term "—($C_1$-$C_3$)alkyl" means a saturated straight-chain or branched hydrocarbon having from 1 to 3 carbon atoms. Representative saturated straight chain ($C_1$-$C_3$)alkyls are -methyl, -ethyl, and -n-propyl, while a saturated branched chain —($C_1$-$C_3$)alkyl is -isopropyl.

The term "—($C_1$-$C_4$)alkyl" means a saturated straight-chain or branched hydrocarbon having from 1 to 4 carbon atoms. Representative saturated straight chain ($C_1$-$C_4$)alkyls are -methyl, -ethyl, -n-propyl, and -n-butyl. Representative saturated branched —($C_1$-$C_4$)alkyls are -isopropyl, -sec-butyl, -isobutyl, and -tert butyl.

Reference herein to a compound of a specified formula is also intended to encompass the salt form of that compound. A "salt" of a compound disclosed herein refers to a salt formed from an acid and the basic nitrogen group of either a 4-Tetrazolyl-4-phenylpiperidine Compound or an intermediate useful in the synthesis thereof. Illustrative salts include, but are not limited, to sulfamate, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "salt" also refers to a salt of a 4-Tetrazolyl-4-phenylpiperidine Compound or an intermediate useful for the synthesis thereof, having an acidic functional group, such as a carboxylic acid functional group, and an inorganic or organic base. Illustrative bases include, but are not limited to, hydroxides of alkali metals such as sodium, potassium and lithium; hydroxides of alkaline earth metal such as calcium and magnesium; hydroxides of other metals, such as aluminum and zinc; ammonia; and organic amines, such as unsubstituted or hydroxy substituted mono-, di-, or trialkylamines; dicyclohexylamine; tributylamine; pyridine; N-methyl-N-ethylamine; diethylamine; triethylamine; mono-, bis- or tris-(2-hydroxy-lower alkyl amines), such as mono- bis- or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

4.2. Methods for Making 4-Tetrazolyl-4-phenylpineridine Compounds

4.2.1. Synthesis of Compound (2)

(1-benzyl-4-phenyl-4-(2H-tetrazol-5-yl)-piperidine)

In one embodiment, the present invention relates to methods for making Compound (2) (1-benzyl-4-phenyl-4-(2H-tetrazol-5-yl)-piperidine, comprising allowing Compound (1) (1-benzyl-4-cyano-4-phenylpiperidine) (which is commercially available) to react with sodium azide in the presence of a zinc salt, such as but not limited to a zinc halide (e.g. $ZnBr_2$, $ZnCl_2$, and $ZnI_2$) or another suitable zinc salt such as $Zn(ClO_4)_2$ or $Zn(CF_3SO_3)_2$, as depicted in Scheme 1 below:

Scheme 1

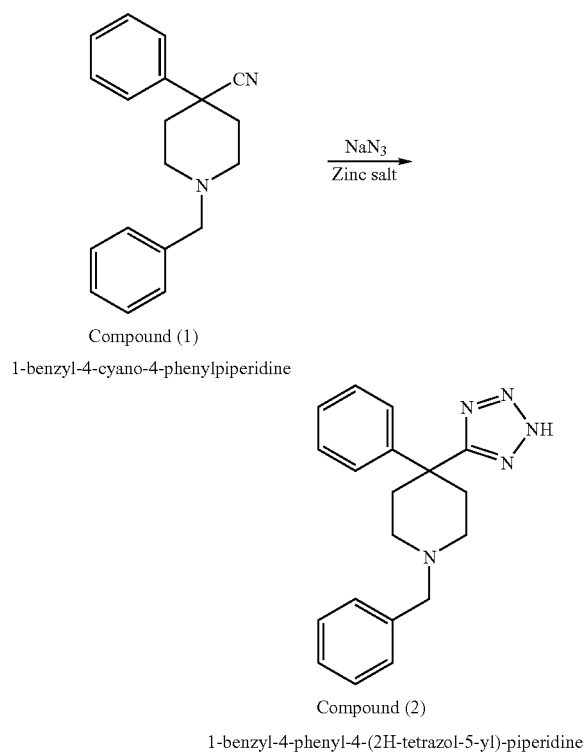

Compound (1)
1-benzyl-4-cyano-4-phenylpiperidine

Compound (2)
1-benzyl-4-phenyl-4-(2H-tetrazol-5-yl)-piperidine

In certain optional embodiments, the phenyl moiety, which is attached to the 4-position of the piperidine ring of Compound (1), is substituted with one or more $R^2$ groups, where $R^2$ is as defined above.

The reaction of Scheme 1 is preferably carried out in a solvent comprising a polar aprotic solvent. Examples of suitable polar aprotic solvents that can be used in the reaction of Scheme 1 include, but are not limited to N-methyl-pyrrolidone, dimethyl formamide, dimethyl acetamide, acetonitrile, and dimethyl sulfoxide. In certain embodiments, the solvent is N-methyl-pyrrolidone or dimethyl acetamide. In a specific embodiment, the solvent is N-methyl-pyrrolidone. In another specific embodiment, the polar aprotic solvent is acetonitrile.

In certain embodiments, the solvent used in the reaction of Scheme 1 is a mixture of a suitable polar aprotic solvent and water. In such embodiments, the ratio of polar aprotic solvent to water can be within the range of from about 50:1 to about 2:1 (v/v) (polar aprotic solvent:water); within the range of from about 20:1 to about 4:1 (polar aprotic solvent:water); or within the range of from about 15:1 to about 10:1 (polar aprotic solvent:water). In a specific embodiment, the solvent mixture is N-methyl-pyrrolidone:water.

In certain embodiments, the reaction of Scheme 1 is carried out with an initial amount of zinc salt within the range of from about 1 to about 5 equivalents, or within the range of from about 2 to about 4 equivalents, on a molar basis, relative to Compound (1). In still other embodiments, the reaction of Scheme 1 is carried out with about 3 equivalents, on a molar basis, of zinc salt, relative to Compound (1). The zinc salt may be selected from the group consisting of zinc(halides)$_2$ including $ZnBr_2$, $ZnCl_2$, and $ZnI_2$, as well as any other suitable zinc salt such as e.g. $Zn(ClO_4)_2$ or $Zn(CF_3SO_3)_2$. In a specific embodiment, the zinc halide is $ZnBr_2$. Zinc salts are commercially available from, e.g., Aldrich Chemical Co., Milwaukee, Wis.

In certain embodiments, the reaction of Scheme 1 is carried out with an initial amount of sodium azide within the range of from about 1 to about 5 equivalents, or within the range of from about 2 to about 4 equivalents, on a molar basis, relative to Compound (1). In a specific embodiment, the reaction of Scheme 1 is carried out with about 4 equivalents, on a molar basis, of sodium azide, relative to Compound (1).

In certain embodiments, Compound (1) is provided as a salt, e.g. the hydrochloride salt, which can be converted to the free amine, using procedures known in the art, prior to reaction with sodium azide. For example, the hydrochloride salt of Compound (1) is dissolved in a suitable organic solvent such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g. over anhydrous sodium sulfate, and then evaporated to provide Compound (1) as the free amine.

The reaction of Scheme 1 can be carried out at reduced pressure, atmospheric pressure or elevated pressure, i.e. greater than atmospheric pressure. In one embodiment, the reaction is carried out at atmospheric pressure. In certain embodiments, the reaction of Scheme 1 is carried out in an inert atmosphere. In one non-limiting aspect of this embodiment, the reaction of Scheme 1 is carried out under a nitrogen atmosphere. In another non-limiting aspect of this embodiment, the reaction of Scheme 1 is carried out under an argon atmosphere.

The reaction of Scheme 1 is carried out, in certain embodiments, at a temperature within the range of from about 100° C. to about 200° C.; at a temperature within the range of from about 120° C. to about 150° C.; or at a temperature within the range of from about 130° C. to about 140° C.

Progress of the reaction of Scheme 1 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1H$ and $^{13}C$ NMR. The reaction according to Scheme 1 is carried out, in one embodiment, until a starting material is consumed or, in another embodiment, until the ratio of product, Compound (2) to starting material, Compound (1) remains essentially constant.

In certain embodiments, the reaction of Scheme 1 is carried out using a solution of Compound (1) in which the initial concentration of Compound (1) is in the range of from about 0.05 M to about 1.0 M, or is in the range of from about 0.1 M to about 0.5 M. In a specific embodiment, the initial concentration of Compound (1) in the reaction of Scheme 1 is about 0.25 M.

Compound (2) formed in the reaction of Scheme 1 may be isolated and/or purified using methods, reagents and equipment known in the art, including, but not limited to those disclosed in Section 5.1, below.

4.2.2. Synthesis of Compounds of Formula III

In another embodiment, the present invention relates to methods for making compounds according to Formula III (e.g compound (4)), comprising allowing Compound (2) (1-benzyl-4-phenyl-4-(2H-tetrazol-5-yl)-piperidine) to react with an alkylating agent according to Formula II in the presence of a non-nucleophilic base, as depicted in Scheme 2 below:

Scheme 2

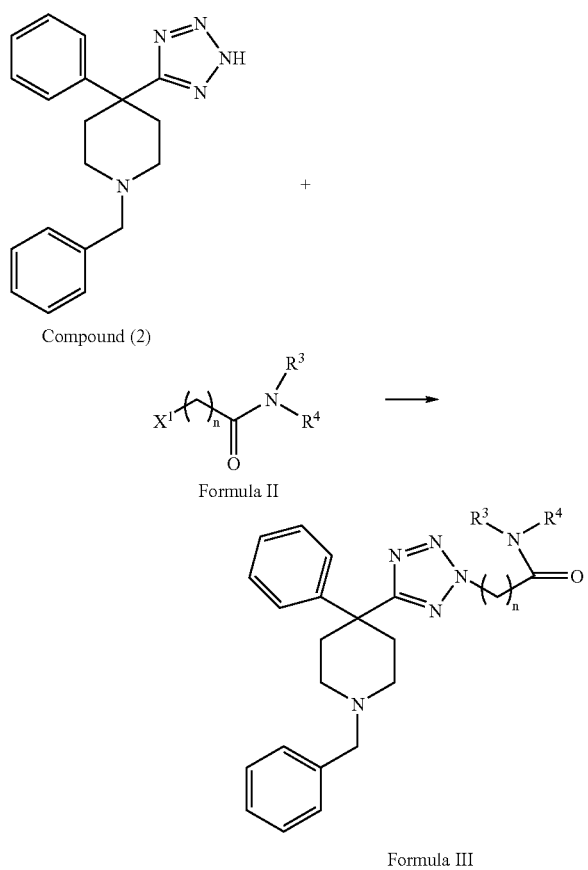

Compound (2)

Formula II

Formula III where n is an integer in the range of 1 to 4, $R^3$ and $R^4$ are each independently H or —($C_1$-$C_4$ alkyl), and $X^1$ is —Br, —Cl, or —I. In certain embodiments, the phenyl moiety attached to the 4-position of the piperidine ring of Compound (2), and, therefore, of a compound according to Formula III formed therefrom, is, optionally, substituted with one or more $R^2$ groups, where $R^2$ is as defined above.

The reaction of Scheme 2 is preferably carried out in a solvent comprising a polar aprotic solvent. Examples of suitable polar aprotic solvents that can be used in the reaction of Scheme 2 include, but are not limited to, N-methyl pyrrolidone, dimethyl formamide, dimethyl acetamide, acetonitrile and dimethyl sulfoxide. In certain embodiments, the solvent is dimethyl formamide or dimethyl acetamide. In a specific embodiment, the solvent is dimethyl formamide. In another specific embodiment, the polar aprotic solvent is acetonitrile.

In certain embodiments, Compound (2) is present in the reaction of Scheme 2 at an initial concentration within the range of from about 0.1 M to about 0.8 M, or at an initial concentration within the range of from about 0.2 M to about 0.6 M. In a specific embodiment, Compound (2) is present in the reaction of Scheme 2 at an initial concentration of about 0.4 M.

The reaction of Scheme 2 can be carried out in the presence of any suitable base such as, but not limited to, triethylamine, diisopropylethylamine, sodium carbonate, potassium carbonate, cesium carbonate, sodium hydroxide, potassium hydroxide, lithium hydroxide, or 2,3,4,6,7,8,9,10-octahydropyrimido[1,2-α]azepine (DBU). In certain embodiments, the non-nucleophilic base is triethylamine, sodium carbonate, or potassium carbonate. In certain embodiments, the non-nucleophilic base is present in the reaction of Scheme 2 at a level within the range of from about 0.5 equivalent to about 3.0 equivalents, within the range of from about 0.75 equivalent to about 2.0 equivalents, or within the range of from about 1.0 equivalent to about 1.5 equivalents, on a molar basis relative to the initial concentration of Compound (2). In certain embodiments, the reaction may further comprise a catalytic amount of 4-dimethylaminopyridine ("4-DMAP") in order to accelerate the rate of the reaction. In a specific embodiment, the non-nucleophilic base is potassium carbonate. In a specific embodiment, the reaction of Scheme 2 is carried out with about 1 equivalent, on a molar basis, of the non-nucleophilic base, relative to the initial concentration of Compound (2).

In certain embodiments, the reaction of Scheme 2 is carried out with an alkylating agent present at a level within the range of from about 0.80 equivalent to about 1.5 equivalents, within the range of from about 0.85 equivalents to about 1.2 equivalents, or within the range of from about 0.95 equivalent to about 1.1 equivalents, on a molar basis, relative to the initial amount of Compound (2) present in the reaction according to Scheme 2. In a specific embodiment, the reaction of Scheme 2 is carried out with about 1 equivalent, on a molar basis, of alkylating agent, relative to the initial amount of Compound (2) present in the reaction according to Scheme 2. Any appropriate alkylating agent, including those according to Formula II, can be used in the reaction of Scheme 2, which will provide the desired product according to Formula III. In certain embodiments the alkylating agent according to Formula II is a haloalkylamide such as, but not limited to bromoacetamide, chloroacetamide, or iodoacetamide. In another, non-limiting, embodiment, the alkylating agent is acrylamide. In certain embodiments, the alkylating agent according to Formula II is bromoacetamide or chloroacetamide. In a specific embodiment, the alkylating agent according to Formula II is bromoacetamide (compound (3)), while in another specific embodiment the alkylating agent according to Formula II is chloroacetamide (compound (11)).

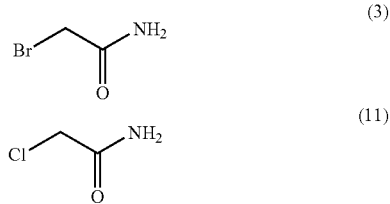

In certain embodiments alkylation is carried out in the presence of a catalytic amount of iodide. The iodide used in this aspect of the reaction of Scheme 2 can be added in the form of a metal salt ($MI_p$), where M is a Group I or Group II metal. p=1 where M is a Group I metal. p=2, where M is a Group II metal. In certain embodiments, iodide is provided as the LiI, NaI, KI, CsI, $CaI_2$, $MgI_2$, or $SrI_2$ salt. In certain embodiments, iodide salts useful in the reaction of Scheme 2 include potassium iodide, sodium iodide, lithium iodide, and cesium iodide, as well as tetralkyl-ammonium iodides. In certain embodiments, the iodide salt is NaI or KI. When used, the iodide salt is present in the reaction of Scheme 2 at an initial level within the range of from about 0.01 equivalent to about 2.0 equivalents, within the range of from about 0.05 equivalent to about 1.0 equivalents, within the range of from about 0.1 equivalent to about 0.6 equivalent, or within the range of from about 0.1 equivalent to about 0.25 equivalent, on a molar basis, relative to the initial amount of Compound (2).

The reaction of Scheme 2 is carried out, in various embodiments, at a temperature within the range of from about 25° C. to about 100° C.; at a temperature within the range of from about 30° C. to about 80° C.; or at a temperature within the range of from about 40° C. to about 60° C.

The reaction of Scheme 2 is carried out for a time sufficient to convert Compound (2) to a compound of Formula III. The reaction according to Scheme 2 is carried out, in one embodiment, until a starting material (e.g. Compound (2)) is consumed or, in another embodiment, until the ratio of product (a compound according to Formula III), to starting material (Compound (2)) remains essentially constant. Typically, a time sufficient for the reaction of Scheme 2 is within the range of from about 4 hours to about 48 hours, from about 8 hours to about 36 hours, or from about 12 hours to about 24 hours. In a specific embodiment, the reaction according to Scheme 2 is carried out for about 16 hours.

The reaction of Scheme 2 can be carried out at reduced pressure, atmospheric pressure or elevated pressure, i.e. greater than atmospheric pressure. In one embodiment, the reaction is carried out at atmospheric pressure. In certain embodiments, the reaction of Scheme 2 is carried out in an inert atmosphere. In one non-limiting aspect of this embodiment, the reaction of Scheme 2 is carried out under a nitrogen atmosphere. In another non-limiting aspect of this embodiment, the reaction of Scheme 2 is carried out under an argon atmosphere.

Progress of the reaction of Scheme 2 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), nuclear magnetic resonance spectroscopy ("NMR"), such as $^1$H and $^{13}$C NMR.

Compounds of Formula III synthesized according to Scheme 2 may be isolated and/or purified using methods, reagents, and equipment well known in the art such as, but not limited to, those disclosed below in Section 5.2.

4.2.3. Synthesis of Compounds of Formula IV

In another embodiment, the present invention relates to methods for making compounds according to Formula IV (e.g. compound (5)), comprising the step of N-debenzylation of a compound according to Formula III, as depicted in Scheme 3 below:

Scheme 3

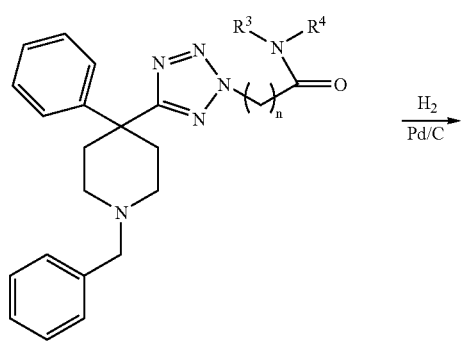

Formula III

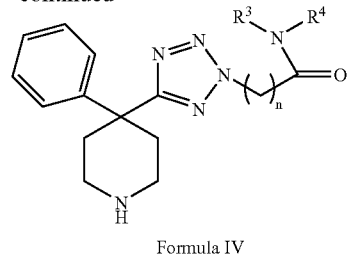

Formula IV where n is an integer in the range of 1 to 4, and $R^3$ and $R^4$ are each independently H or —($C_1$-$C_4$ alkyl). In certain embodiments, the phenyl moiety, which is attached to the 4-position of the piperidine ring of a compound according to Formula III, and, therefore, of a compound according Formula IV formed therefrom, is substituted with one or more $R^2$ groups, where $R^2$ is as defined above.

The reaction of Scheme 3 is preferably carried out in a solvent comprising a polar protic solvent. Examples of suitable polar protic solvents that can be used in the reaction of Scheme 3 include, but are not limited to lower chain alcohols such as methanol, ethanol, isopropanol, n-propanol, butanol, and ethylene glycol. In certain embodiments, the solvent is methanol or ethanol. In a specific embodiment, the polar protic solvent is ethanol.

In the reaction of Scheme 3, the compound of Formula III is present at an initial concentration within the range of from about 0.025 M to about 0.8 M, within the range of from about 0.05 M to about 0.4 M, or within the range of from about 0.1 M to about 0.2 M.

The reaction of Scheme 3 is also carried out, in certain embodiments, in the presence of a suitable acid catalyst such as, but not limited to, methane sulfonic acid, toluene sulfonic acid, hydrochloric acid, sulfuric acid, phosphoric acid, acetic acid, or camphor sulfonic acid. In certain embodiments, the acid catalyst is hydrochloric acid or acetic acid. In a specific embodiment, the acid catalyst is acetic acid.

In certain embodiments, the acid catalyst used in the reaction of Scheme 3 is present at an initial level within the range of from about 0.01 equivalent to about 0.5 equivalent, or within the range of from about 0.05 equivalent to about 0.25 equivalent, on a molar basis, relative to the initial concentration of the compound of Formula III. In a specific embodiment, the acid catalyst used in the reaction of Scheme 3 is present at an initial level of about 0.1 equivalent, on a molar basis, relative to the initial concentration of the compound of Formula III.

The N-debenzylation reaction of Scheme 3 can be carried out in the presence of hydrogen gas and a precious-metal, i.e. a platinum-group metal, catalyst. Suitable precious-metal catalysts are well known in the art and include, but are not limited to those comprising iridium, osmium, palladium, platinum, rhodium, or ruthenium. Such catalysts generally comprise the precious metal distributed on a suitable support such as, but not limited to, activated carbon. In certain embodiments, the catalyst comprises palladium, platinum, rhodium, or ruthenium. In other embodiments, the catalyst comprises palladium or platinum. In a specific embodiment the catalyst comprises powdered palladium distributed on an activated carbon support.

In certain embodiments, a compound according to Formula III is dissolved in the polar protic solvent under an inert atmosphere, such as but not limited to an argon atmosphere. In another aspect of this embodiment, the vessel containing the reaction mixture, which comprises a solution of a compound according to Formula III, acid catalyst, and precious-metal catalyst, is purged with hydrogen. The reaction according to Scheme 3 is then allowed to run in the presence of hydrogen gas, at a pressure within the range of from about atmospheric pressure (about 14.7 psi (lbs./in$^2$)) to about 500 psi, at a pressure within the range of from about atmospheric pressure (about 14.7 psi) to about 100 psi, or at a pressure within the range of from about atmospheric pressure (about 14.7 psi) to about 25 psi.

In certain embodiments, the reaction according to Scheme 3 is run at a temperature within the range of from about 5° C. to about 100° C.; at a temperature within the range of from about 15° C. to about 50° C.; or at a temperature within the range of from about 20° C. to about 30° C.

The reaction of Scheme 3 is carried out for a time sufficient to convert a compound of Formula III to a compound of Formula IV. The reaction according to Scheme 3 is carried out, in one embodiment, until the starting material (a compound of Formula III) is consumed or, in another embodiment, until the ratio of product (a compound of Formula IV) to starting material (a compound of Formula III) remains essentially constant. Typically, a time sufficient for the reaction of Scheme 3 is within the range of from about 4 hours to about 48 hours, within the range of from about 8 hours to about 36 hours, or within the range of from about 12 hours to about 24 hours. In a specific embodiment, the reaction of Scheme 3 is carried out for about 16 hours.

Progress of the reaction of Scheme 3 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR.

Compounds of Formula IV synthesized according to Scheme 3 may be isolated and/or purified using methods, reagents, and equipment known in the art such as, but not limited to, those disclosed below in Section 5.3, below.

4.2.4. Methods for Making Compounds According to Formula VII

Scheme 4 depicts methods for making a compound according to Formula VII (e.g. compound (6)). In certain embodiments, bromoacids according to Formula V are converted to bromoacid chlorides of Formula VI using thionylchloride (J. S. Pizey, *Synthetic Reactions* 2: 65 (1974)). Bromoacid chlorides of Formula VI are reacted with NH(Z$^1$)(Z$^2$) (where Z$^1$ and Z$^2$ are each independently a —(C$_1$-C$_4$ alkyl) group) optionally in the presence of a base such as Na$_2$CO$_3$, to provide reactive intermediates according to Formula VII, as depicted in Scheme 4, below:

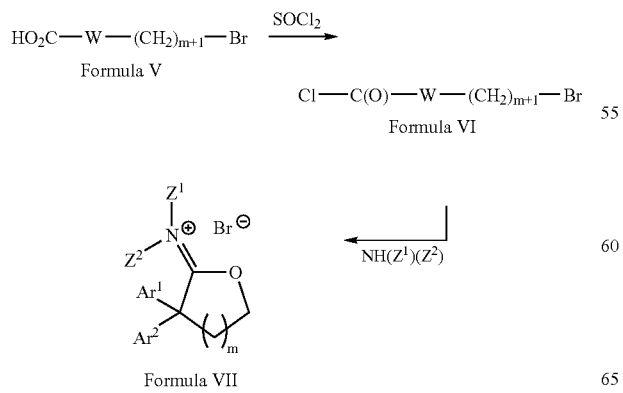

where W is —C(Ar$^1$)(Ar$^2$), where Ar$^1$ is —C$_3$-C$_8$ cycloalkyl, phenyl, naphthyl, anthryl, phenanthryl or -(5-7-membered) heteroaryl, each being unsubstituted or substituted with one or more R$^2$ groups; Ar$^2$ is phenyl, naphthyl, anthryl, phenanthryl or -(5-7-membered) heteroaryl, each being unsubstituted or substituted with one or more R$^2$ groups; R$^2$ is halogen, —C$_1$-C$_3$ alkyl, —O—(C$_1$-C$_3$ alkyl), —NH(C$_1$-C$_3$ alkyl) or —N(C$_1$-C$_3$ alkyl)$_2$; m is an integer from 0 to 4; and Z$^1$ and Z$^2$ are each independently —(C$_1$-C$_4$ alkyl).

4.2.5. Methods for Making Compounds According to Formula I

In another embodiment, the present invention relates to methods for making compounds according to Formula I, such as, but not limited to, Compound (7), comprising allowing a compound according to Formula IV (e.g compound (5)) to react with a compound according to Formula VII (e.g. compound (6)) in the presence of a suitable nucleophilic or a non-nucleophilic base, as depicted in Scheme 5 below:

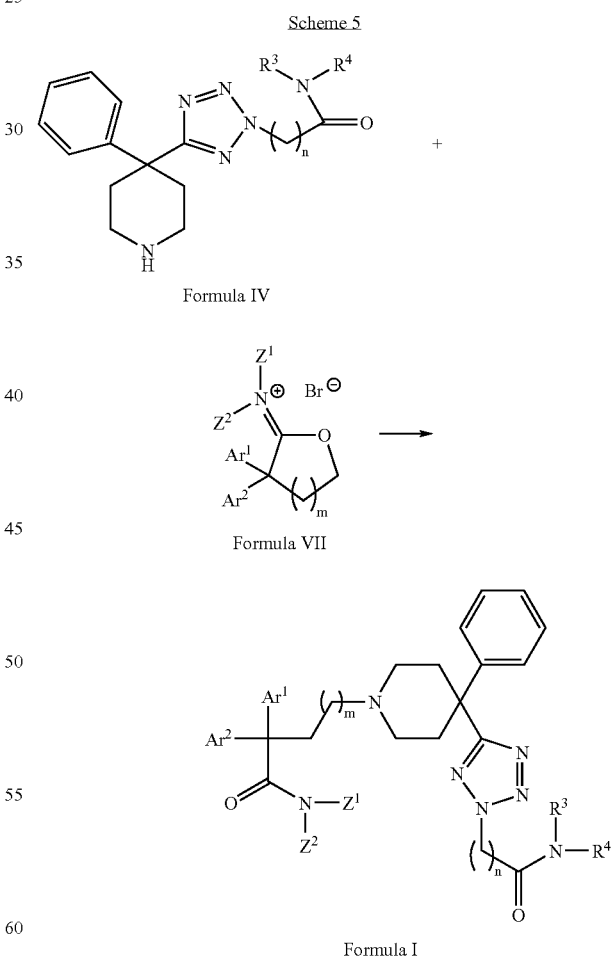

Ar$^1$ is —C$_3$-C$_8$ cycloalkyl, phenyl, naphthyl, anthryl, phenanthryl or -(5-7-membered) heteroaryl, each being unsubstituted or substituted with one or more $R^2$ groups; $Ar^2$ is phenyl, naphthyl, anthryl, phenanthryl or -(5-7-membered) heteroaryl, each being unsubstituted or substituted with one or more $R^2$ groups; $Z^1$ and $Z^2$ are each independently a —($C_1$-$C_4$ alkyl) group; $R^2$ is halogen, —$C_1$-$C_3$ alkyl, —O—($C_1$-$C_3$ alkyl), —NH($C_1$-$C_3$ alkyl) or —N($C_1$-$C_3$ alkyl)$_2$; $R^3$ and $R^4$ are each independently H or —($C_1$-$C_4$ alkyl); n is an integer ranging from 1 to 4; and m is an integer ranging from 0 to 4. In certain embodiments, the phenyl moiety, which is attached to the 4-position of the piperidine ring of the compound according to Formula IV or of a compound according to Formula I formed therefrom, is substituted with one or more $R^2$ groups, where $R^2$ is as defined above.

The reaction of Scheme 5 is preferably carried out in a solvent comprising a polar aprotic solvent. Examples of suitable polar aprotic solvents that can be used in the reaction of Scheme 5 include, but are not limited to, N-methylpyrrolidone, dimethyl formamide, dimethyl acetamide, acetonitrile, and dimethyl sulfoxide. In certain embodiments the polar aprotic solvent is dimethyl formamide or dimethyl acetamide. In a specific embodiment, the polar aprotic solvent is dimethyl formamide. In another specific embodiment, the polar aprotic solvent is acetonitrile.

In the reaction of Scheme 5, the compound of Formula IV is present at an initial concentration within the range of from about 0.05 M to about 1.0 M, within the range of from about 0.1 M to about 0.5 M, or within the range of from about 0.2 M to about 0.3 M.

The reaction of Scheme 5 is also carried out, in certain embodiments, in the presence of a suitable nucleophilic or a non-nucleophilic base, such as but not limited to, triethylamine, diisopropylethylamine, sodium carbonate, potassium carbonate, cesium carbonate, or 2,3,4,6,7,8,9,10-octahydropyrimido[1,2-α]azepine (DBU). In certain embodiments, the reaction may further comprise a catalytic amount of 4-DMAP in order to accelerate the rate of the reaction. In certain embodiments the non-nucleophilic base is, triethylamine, sodium carbonate, or potassium carbonate. In a specific embodiment, the non-nucleophilic base is sodium carbonate.

In certain embodiments, the non-nucleophilic base used in the reaction of Scheme 5 is present at an initial level within the range of from about 1 equivalent to about 4 equivalents, or within the range of from about 1.5 equivalents to about 3 equivalents, or within the range of from about 2 equivalents to about 2.5 equivalents on a molar basis, relative to the initial concentration of the compound of Formula IV.

In certain embodiments, the compound according to Formula VII used in the reaction of Scheme 5 is present at an initial level within the range of from about 0.6 equivalent to about 3 equivalents, or within the range of from about 0.8 equivalents to about 2 equivalents, or within the range of from about 1 equivalent to about 1.5 equivalents, on a molar basis, relative to the initial concentration of the compound of Formula IV. In a specific embodiment, the compound according to Formula VII used in the reaction of Scheme 5 is present at an initial level of about 1 equivalent, on a molar basis, relative to the initial concentration of the compound of Formula IV.

The reaction of Scheme 5 can be carried out at reduced pressure, atmospheric pressure or elevated pressure, i.e. greater than atmospheric pressure. In one embodiment, the reaction is carried out at atmospheric pressure. The reaction of Scheme 5 can be carried out in an inert atmosphere. In a specific, non-limiting embodiment, the reaction of Scheme 5 is carried out in a nitrogen atmosphere. In another specific, non-limiting embodiment, the reaction of Scheme 5 is carried out in an argon atmosphere.

In certain embodiments, the reaction according to Scheme 5 is run at a temperature within the range of from about 25° C. to about 175° C; at a temperature within the range of from about 50° C. to about 150° C.; or at a temperature within the range of from about 75° C. to about 125° C. In a specific embodiment, the reaction according to Scheme 5 is run at a temperature of about 100° C.

The reaction of Scheme 5 is carried out for a time sufficient to convert a compound according to Formula IV to a compound of Formula I. The reaction according to Scheme 5 is carried out, in one embodiment, until the starting material (i.e. a compound according to Formula IV) is consumed or, in another embodiment, until the ratio of product (a compound according to Formula I) to starting material (i.e. a compound according to Formula IV) remains essentially constant. Typically, a time sufficient for the reaction of Scheme 5 is within the range of from about 8 hours to about 48 hours, from about 12 hours to about 36 hours, or from about 16 hours to about 24 hours.

Progress of the reaction of Scheme 5 is monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR.

Compounds of Formula I synthesized according to Scheme 5 may be isolated and/or purified using methods, reagents, and equipment known in the art such as, but not limited to, those disclosed below in Section 5.5, below.

4.2.6. Method for Making Compound (7) According to Schemes 1-5

The methods and reagents of Schemes 1-5 above, therefore, are combined to provide a method for the synthesis of compounds according to Formula I. For example, as depicted in Scheme 6, Compound (7), which is a compound according to Formula I, is synthesized according to the methods, and under the conditions disclosed, in Sections 4.2.1 to 4.2.5, above.

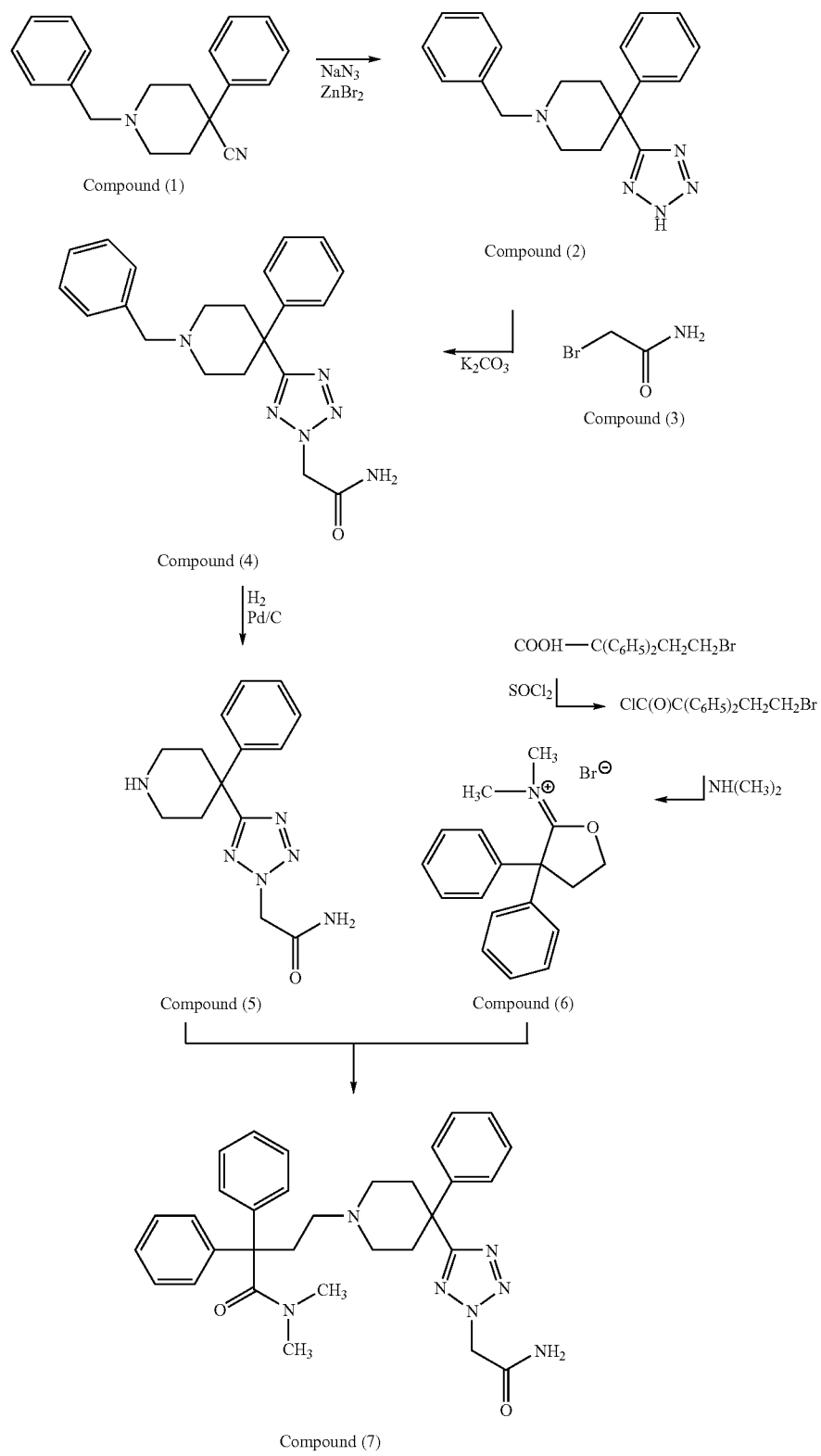

4.2.7. Method for Making Compound (9)

In another embodiment, the present invention relates to methods for making Compound (9) (4-phenyl-4-(2H-tetrazol-5-yl)-piperidine) comprising allowing Compound (8) (4-cyano-4-phenyl-piperidinium chloride) to react with sodium azide in the presence of an appropriate zinc salt as depicted in Scheme 7 below:

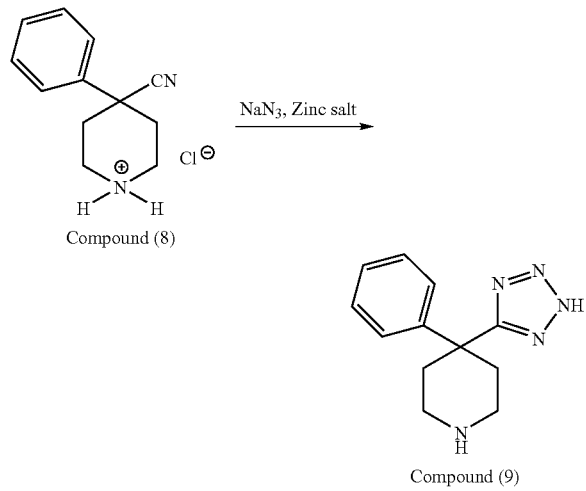

In certain embodiments, the phenyl moiety, which is attached to the 4-position of the piperidine ring of Compound (8) (which is commercially available), and of those additional compounds formed therefrom, is substituted with one or more $R^2$ groups, where $R^2$ is as defined above.

The reaction of Scheme 7 is carried out in a solvent comprising a polar aprotic solvent. Examples of suitable polar aprotic solvents that can be used in the reaction of Scheme 7 include, but are not limited to dioxane, N-methyl-pyrrolidone, dimethyl formamide, dimethyl acetamide, acetonitrile, or dimethyl sulfoxide.

In certain embodiments, the solvent comprises a mixture of water and a suitable polar aprotic solvent. In such embodiments the ratio of water to polar aprotic solvent can be within the range of from about 10:1 to about 1:1 (water:polar aprotic solvent); within the range of from about 5:1 to about 1:1 (water:polar aprotic solvent); or within the range of from about 2:1 to 1:1 (water:polar aprotic solvent). In certain embodiments, the polar aprotic solvent is dioxane. In a specific embodiment, the solvent is a 64:36 water:dioxane mixture.

In certain embodiments, the zinc salt used in the reaction of Scheme 7 is present at an initial level within the range of from about 1 to about 5 equivalents, or the range of from about 2 to about 4 equivalents on a molar basis, relative to Compound (8). In other embodiments, the reaction of Scheme 7 is carried out with about 3 equivalents, on a molar basis, of zinc salt, relative to Compound (8). In other embodiments, the reaction of Scheme 7 is carried out with about 2 equivalents of zinc salt, on a molar basis, relative to Compound (8). In a specific embodiment, the reaction of Scheme 7 is carried out with about 1 equivalent, on a molar basis, of zinc salt, relative to Compound (8). The zinc salt is any appropriate zinc salt, but may be selected from the group consisting of zinc(halides)$_2$ including $ZnBr_2$, $ZnCl_2$, and $ZnI_2$, as well as other suitable zinc salts such as $Zn(ClO_4)_2$ and $Zn(CF_3SO_3)_2$. In certain embodiments, the zinc salt is a zinc halide selected from the group consisting of $ZnBr_2$, $ZnCl_2$, and $ZnI_2$. In a specific embodiment, the zinc salt is $ZnBr_2$.

In certain embodiments, sodium azide used in reaction of Scheme 7 is present at an initial level of within the range of from about 1 to about 5 equivalents, to within the range of from about 2 to about 4 equivalents, on a molar basis, relative to Compound (8). In a specific embodiment, the reaction of Scheme 7 is carried out with about 2 equivalents of sodium azide, on a molar basis, relative to Compound (8).

The reaction of Scheme 7 is carried out at reduced pressure, atmospheric pressure or elevated pressure, i.e. greater than atmospheric pressure. In one embodiment, the reaction is carried out at atmospheric pressure. The reaction of Scheme 7 can be carried out in an inert atmosphere. In a specific, non-limiting embodiment, the reaction of Scheme 7 is carried out in a nitrogen atmosphere. In another specific, non-limiting embodiment, the reaction of Scheme 7 is carried out in an argon atmosphere.

The reaction of Scheme 7 is carried out, in certain embodiments, at a temperature within the range of from about 70° C. to about 120° C.; at a temperature within the range of from about 80° C. to about 110° C.; or at a temperature within the range of from about 90° C. to about 100° C.

Progress of the reaction of Scheme 7 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1H$ and $^{13}C$ NMR. The reaction according to Scheme 7 is carried out, in one embodiment, until a starting material, Compound (8), is consumed or, in another embodiment, until the ratio of product, Compound (9), to starting material, Compound (8), remains essentially constant.

In certain embodiments, the reaction of Scheme 7 is carried out using a solution of Compound (8) in which the initial concentration of Compound (8) is within the range of from about 0.01 M to about 3.0 M, is within the range of from about 0.025M to about 2.0 M, is within the range of from about 0.05 M to about 1.0 M, or is within the range of from about 0.1M to about 0.5 M, or within the range of from about 0.2 M to about 0.4 M. In a specific embodiment, the reaction of Scheme 7 is carried out using a solution of Compound (8) in which the initial concentration of Compound (8) is about 0.4 M.

Compound (9) formed in the reaction of Scheme 7 may be isolated and/or purified using methods, reagents and equipment known in the art. In certain embodiments, Compound (9) formed in the reaction of Scheme 7 is isolated by filtration, crystallization, chromatography, or extraction. In a specific embodiment, Compound (9) formed in the reaction of Scheme 7 is isolated by filtration.

4.2.8. Methods for Making Compounds According to Formula VIII

In another embodiment, the present invention relates to methods for making compounds according to Formula VIII (e.g. compound (10)), that comprise allowing Compound (9) (4-phenyl-4-(2H-tetrazol-5-yl)-piperidine) to react with a compound of Formula VII (e.g compound (6)), as depicted in Scheme 8, below

Scheme 8

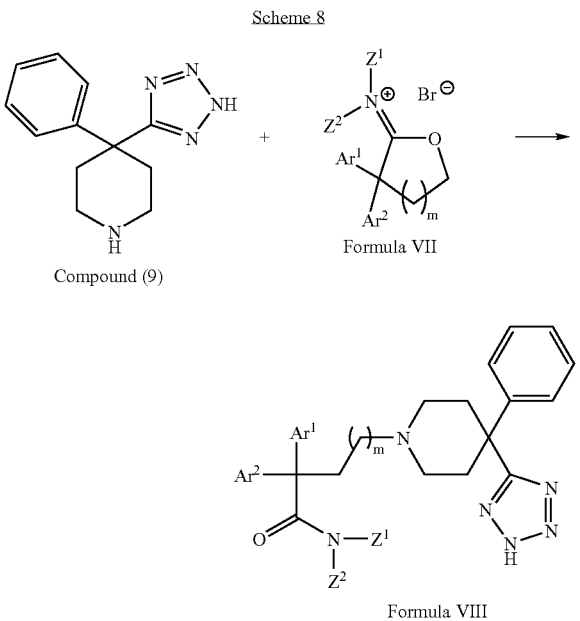

Compound (9) + Formula VII → Formula VIII where $Ar^1$ is —$C_3$-$C_8$ cycloalkyl, phenyl, naphthyl, anthryl, phenanthryl or -(5-7-membered) heteroaryl, each being unsubstituted or substituted with one or more $R^2$ groups; $Ar^2$ is phenyl, naphthyl, anthryl, phenanthryl or -(5-7-membered) heteroaryl, each being unsubstituted or substituted with one or more $R^2$ groups; $Z^1$ and $Z^2$ are each independently a —($C_1$-$C_4$ alkyl) group; $R^2$ is halogen, —$C_1$-$C_3$ alkyl, —O—($C_1$-$C_3$ alkyl), —NH($C_1$-$C_3$ alkyl) or —N($C_1$-$C_3$ alkyl)$_2$; and m is an integer ranging from 0 to 4. In certain embodiments, the phenyl moiety, which is attached to the 4-position of the piperidine ring of Compound (9), and, therefore, of a compound according Formula VIII formed therefrom, is substituted with one or more $R^2$ groups, where $R^2$ is as defined above.

The reaction of Scheme 8 is preferably carried out in a solvent comprising a polar aprotic solvent. Examples of suitable polar aprotic solvents that can be used in the reaction of Scheme 8 include, but are not limited to, N-methylpyrrolidone, dimethyl formamide, dimethyl acetamide, acetonitrile, and dimethyl sulfoxide. In certain embodiments the polar aprotic solvent is dimethyl formamide or dimethyl sulfoxide. In a specific embodiment, the polar aprotic solvent is dimethyl sulfoxide. In another specific embodiment, the polar aprotic solvent is acetonitrile.

In the reaction of Scheme 8, Compound (9) is present at an initial concentration within the range of from about 0.01 M to about 3.0 M, within the range of from about 0.02 M to about 2.0 M, within the range of from about 0.05 M to about 1.0 M, within the range of from about 0.1 M to about 0.8 M, or within the range of from about 0.2 M to about 0.4 M.

The reaction of Scheme 8 is also carried out, in certain embodiments, in the presence of a suitable non-nucleophilic base, such as but not limited to, 2,3,4,6,7,8,9,10-octahydro-pyrimido[1,2-α]azepine (DBU), triethylamine, diisopropylethylamine, sodium carbonate, potassium carbonate, cesium carbonate. In certain embodiments the non-nucleophilic base is DBU. In certain embodiments, the reaction may further comprise a catalytic amount of 4-DMAP in order to accelerate the rate of the reaction.

In certain embodiments, the non-nucleophilic base used in the reaction of Scheme 8 is present at an initial level within the range of from about 1 equivalent to about 10 equivalents, or within the range of from about 2 equivalents to about 8 equivalents, or within the range of from about 3 equivalents to about 5 equivalents on a molar basis, relative to the initial concentration of Compound (9).

In certain embodiments, the compound according to Formula VII used in the reaction of Scheme 8 is present at an initial level within the range of from about 0.6 equivalent to about 3 equivalents, or within the range of from about 0.8 equivalents to about 2 equivalents, or within the range of from about 1 equivalent to about 1.5 equivalents on a molar basis, relative to the initial concentration of the Compound (9).

The reaction of Scheme 8 is carried out at reduced pressure, atmospheric pressure or elevated pressure, i.e. greater than atmospheric pressure. In one embodiment, the reaction is carried out at atmospheric pressure. The reaction of Scheme 8 can be carried out in an inert atmosphere. In a specific, non-limiting embodiment, the reaction of Scheme 8 is carried out in a nitrogen atmosphere. In another specific, non-limiting embodiment, the reaction of Scheme 8 is carried out in an argon atmosphere.

In certain embodiments, the reaction according to Scheme 8 is run at a temperature within the range of from about 5° C. to about 50° C.; at a temperature within the range of from about 10° C. to about 40° C.; or at a temperature within the range of from about 15° C. to about 30° C.; or at a temperature within the range of from about 20° C. to about 25° C.

The reaction of Scheme 8 is carried out for a time sufficient to convert Compound (9) to a compound of Formula VIII. The reaction according to Scheme 8 is carried out, in one embodiment, until the starting material (i.e. Compound (9)) is consumed or, in another embodiment, until the ratio of product (a compound according to Formula IX), to starting material (i.e. Compound (9)), remains essentially constant. Typically, a time sufficient for the reaction of Scheme 8 is within the range of from about 5 minutes to about 5 hours, from about 15 minutes to about 4 hours, or from about 0.5 hour to about 2 hours.

Progress of the reaction of Scheme 8 is monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR.

Compounds of Formula VIII synthesized according to Scheme 8 may be isolated and/or purified using methods, reagents, and equipment known in the art. In certain embodiments, Compounds of Formula VIII synthesized according to Scheme 8 are isolated and/or purified by crystallization, extraction, or chromatography.

4.2.9. Methods for Making Compounds According to Formula I

In another embodiment, the present invention relates to methods for making compounds according to Formula I, that comprise allowing a compound according to Formula VIII (e.g. compound (10)) to react with a compound according to Formula II (e.g. compound (3) or compound (11)), in the presence of a non-nucleophilic base, as depicted in Scheme 9, below

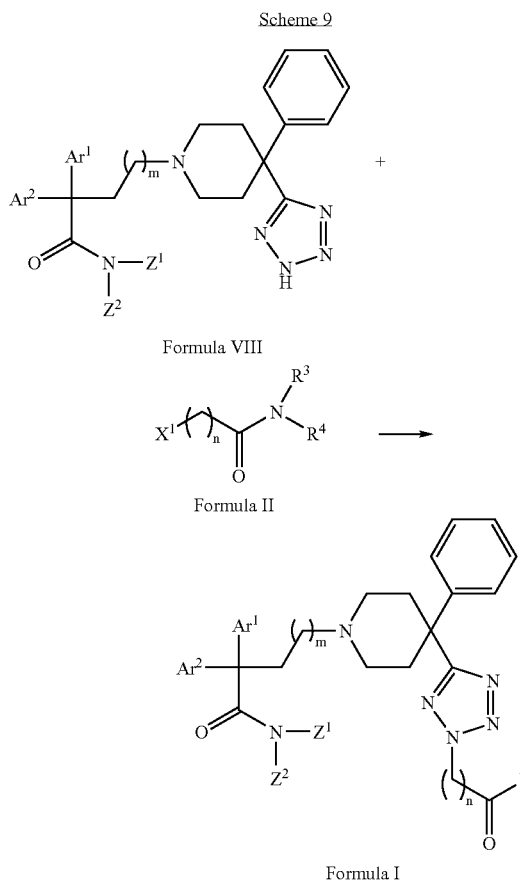

where $Ar^1$ is —$C_3$-$C_8$ cycloalkyl, phenyl, naphthyl, anthryl, phenanthryl or -(5-7-membered) heteroaryl, each being unsubstituted or substituted with one or more $R^2$ groups; $Ar^2$ is phenyl, naphthyl, anthryl, phenanthryl or -(5-7-membered) heteroaryl, each being unsubstituted or substituted with one or more $R^2$ groups; $X^1$ is —Br, —Cl, or —I; $Z^1$ and $Z^2$ are each independently a —($C_1$-$C_4$ alkyl) group; $R^3$ and $R^4$ are each independently H or —($C_1$-$C_4$ alkyl); $R^2$ is halogen, —$C_1$-$C_3$ alkyl, —O—($C_1$-$C_3$ alkyl), —NH($C_1$-$C_3$ alkyl) or —N($C_1$-$C_3$ alkyl)$_2$; n is an integer ranging from 1 to 4; and m is an integer ranging from 0 to 4. Moreover, in certain embodiments, the phenyl moiety, which is attached to the 4-position of the piperidine ring of compounds according to Formula VIII and Formula I, can be substituted with one or more $R^2$ groups, where $R^2$ is as defined above.

The reaction of Scheme 9 is carried out in a solvent comprising a polar aprotic solvent. Examples of suitable aprotic polar solvents that can be used in the reaction of Scheme 9 include, but are not limited to N-methyl pyrrolidone, dimethyl formamide, dimethyl acetamide, and acetonitrile dimethyl sulfoxide. In certain embodiments, the solvent is dimethyl formamide or dimethyl sulfoxide. In a specific embodiment, the solvent is dimethyl formamide. In another specific embodiment, the polar aprotic solvent is acetonitrile.

In certain embodiments, the compound according to Formula VIII is present in the reaction of Scheme 9 at an initial concentration within the range of from about 0.01 M to about 3.0 M, within the range of from about 0.015 M to about 2.0 M, within the range of from about 0.2 M to about 1.0 M, within the range of from about 0.025 M to about 0.8 M, at an initial concentration within the range of from about 0.05 M to about 0.6 M, or at an initial concentration within the range of from about 0.1 M to about 0.2 M.

The reaction of Scheme 9 can be carried out in the presence of any suitable non-nucleophilic base such as, but not limited to, triethylamine, diisipropylethylamine, sodium carbonate, potassium carbonate, cesium carbonate, sodium hydroxide, potassium hydroxide, lithium hydroxide, or (2,3,4,6,7,8,9, 10-Octahydro-pyrimido[1,2-α]azepine) (DBU). In certain embodiments, the reaction may further comprise a catalytic amount of 4-DMAP in order to accelerate the rate of the reaction. In certain embodiments, the non-nucleophilic base is triethylamine, sodium carbonate, or potassium carbonate. In a specific embodiment, the non-nucleophilic base is potassium carbonate.

In certain embodiments, the non-nucleophilic base used in the reaction of Scheme 9 is present at an initial level within the range of from about 0.5 equivalent to about 5 equivalents, within the range of from about 1 equivalent to about 4 equivalents, or within the range of from about 2 equivalents to about 3 equivalents, on a molar basis, relative to the initial concentration of the compound according to Formula VIII.

In certain embodiments, the reaction of Scheme 9 is carried out with the alkylating reagent present at a level within the range of from about 0.80 equivalent to about 1.5 equivalents, within the range of from about 0.85 equivalents to about 1.2 equivalents, within the range of from about 0.95 equivalent to about 1.1 equivalents, on a molar basis, relative to the initial amount of the compound of Formula VIII present in the reaction according to Scheme 9. In a specific embodiment, the reaction of Scheme 9 is carried out with the alkylating reagent present at a level of about 1.0 equivalent, on a molar basis, relative to the initial amount of the compound of Formula VIII present in the reaction. Any appropriate alkylating agent that will provide the desired product according to Formula I, which will include, but not be limited to, those alkylating agents according to Formula II, can be used in the reaction of Scheme 9. In certain embodiments the alkylating agent according to Formula II is a haloalkylamide such as, but not limited to bromoacetamide, chloroacetamide, or iodoacetamide, or another suitable alkylating agent, such as but not limited to, acrylamide. In certain embodiments, the alkylating agent according to Formula II is bromoacetamide or chloroacetamide.

In a specific embodiment, the alkylating agent according to Formula II is chloroacetamide. In another specific embodiment, the alkylating agent according to Formula II can be chloroacetamide and the alkylation is carried out in the presence of a catalytic amount of iodide. The iodide used in this aspect of the reaction of Scheme 9 is added in the form of a metal salt ($MI_p$), where M is a Group I or Group III metal. Where M is a Group I metal, then p=1. Where M is a Group II metal, then p=2. In certain embodiments, iodide in provided as the LiI, NaI, KI, CsI, $CaI_2$, $MgI_2$, or $SrI_2$ salt. In certain embodiments, iodide salts useful in the reaction of Scheme 9 include potassium iodide, sodium iodide, lithium iodide, and cesium iodide, as well as a tetralkyl-ammonium iodides. In certain embodiments, the iodide salt is NaI or KI. When used, the iodide salt is present in the reaction of Scheme 9 at an initial amount within the range of from about 0.01 equivalents to about 1.0 equivalent, within the range of from about 0.05 equivalent to about 0.8 equivalents, within the range of from about 0.1 equivalent to about 0.6 equivalent, or within the range of from about 0.2 equivalent to about 0.4 equivalent, on a molar basis, relative to the initial amount of the compound according to Formula VIII, present in the reaction according to Scheme 9.

The reaction of Scheme 9 is carried out, in various embodiments, at a temperature within the range of from about 30° C. to about 90° C.; at a temperature within the range of from about 40° C. to about 80° C.; or at a temperature within the range of from about 50° C. to about 70° C. In a specific embodiment, the reaction of Scheme 9 is carried out at temperature of about 60° C.

The reaction of Scheme 9 is carried out for a time sufficient to convert a compound according to Formula VIII to a compound of Formula I. The reaction according to Scheme 9 is carried out, in one embodiment, until a starting material (e.g. the compound according to Formula VIII) is consumed or, in another embodiment, until the ratio of product, (a compound according to Formula I), to starting material (a compound according to Formula VIII), remains essentially constant. Typically, a time sufficient for the reaction of Scheme 9 is within the range of from about 1 hour to about 16 hours, within the range of from about 2 hours to about 8 hours, within the range of from about 3 hours to about 6 hours, or within the range of from about 4 hours to about 5 hours.

In certain embodiments, the reaction of Scheme 9 is carried out in an inert atmosphere. In one non-limiting aspect of this embodiment, the reaction of Scheme 9 is carried out under a nitrogen atmosphere. In another non-limiting aspect of this embodiment, the reaction of Scheme 9 is carried out under an argon atmosphere.

Progress of the reaction of Scheme 9 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), nuclear magnetic resonance spectroscopy ("NMR"), such as $^1H$ and $^{13}C$ NMR.

Compounds of Formula I synthesized according to Scheme 9 may be isolated and/or purified using methods, reagents, and equipment known in the art. In certain embodiments, Compounds of Formula I synthesized according to Scheme 9 are isolated by crystallization, chromatography (e.g. on silica gel), or extraction with an organic solvent after adding a reaction mixture according to Scheme 9 to water. In a specific embodiment, Compounds of Formula I synthesized according to Scheme 9 are isolated by crystallization.

4.2.10. Method for Making Compound (7) According to Schemes 7-9

In another embodiment, the present invention is directed toward the synthesis of a 4-Tetrazolyl-4-phenylpiperidine Compound, in which the methods and reagents of Scheme 7-9 above, are combined to provide a method for the synthesis of a compound according to Formula I. For example, as depicted in Scheme 10, below, Compound (7), which is an example of a compound according to Formula I, is synthesized according to the methods and conditions disclosed in Sections 4.2.7 to 4.2.9, above.

Scheme 10

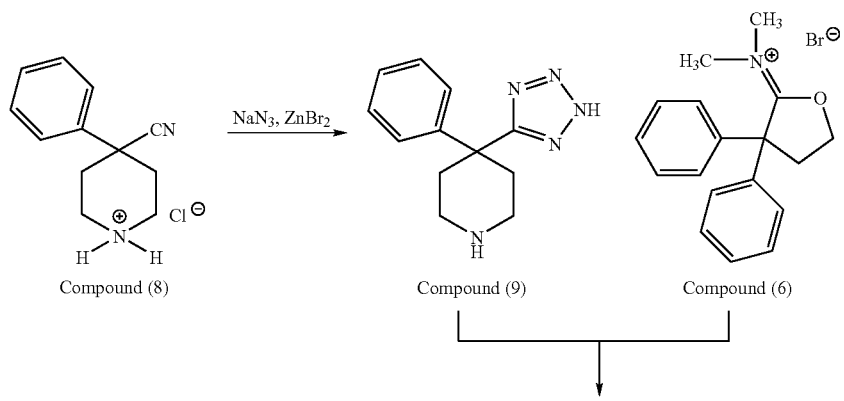

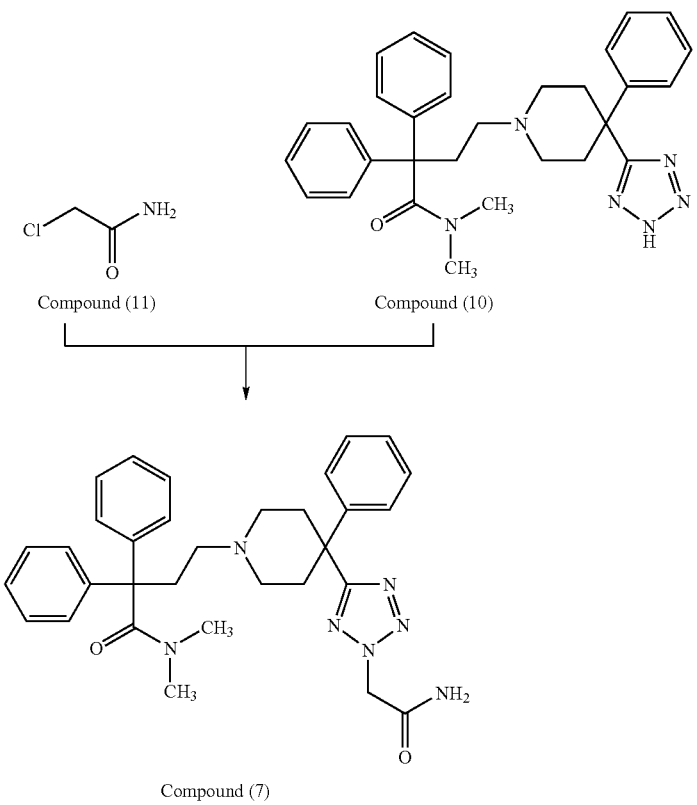

In certain embodiments, conversion of compound (8) to compound (9) is carried out in a solvent comprising a polar aprotic solvent. In certain embodiments, the polar aprotic solvent is selected from the group consisting of dioxane, N-methyl-pyrrolidone, dimethyl formamide, dimethyl acetamide, acetonitrile, dimethyl sulfoxide, and combinations thereof. In other embodiments, the solvent comprises a mixture the suitable polar aprotic solvent and water. In such embodiments the ratio of water to polar aprotic solvent can be within the range of from about 10:1 to about 1:1 (water:polar aprotic solvent). In certain embodiments, the polar aprotic solvent in the mixture is dioxane. In another specific embodiment, the polar aprotic solvent in the mixture is acetonitrile.

4.2.11. Method for Making Compound (14)

(tert-butyl 4-phenyl-4-(1H-tetrazol-5-yl)piperidine-1-carboxylate)

In another embodiment, the present invention relates to methods for making Compound (14) (tert-butyl 4-phenyl-4-(1H-tetrazol-5-yl)piperidine-1-carboxylate), comprising allowing Compound (9) (4-phenyl-4-(2H-tetrazol-5-yl)-piperidine) to react with Compound (12) (di-tertbutyldicarbonate) in an aqueous solvent in the presence of a suitable base as depicted in Scheme 11, below.

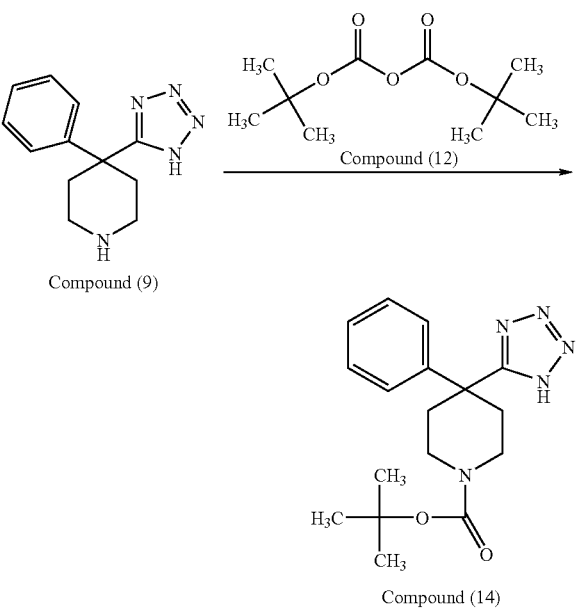

In certain embodiments, di-tertbutyldicarbonate used in the reaction of Scheme 11 is present at an initial level within the range of from about 1 to about 3 equivalents, or the range of from about 1 to about 2.5 equivalents on a molar basis, relative to Compound (9). In other embodiments, the reaction of Scheme 11 is carried out with about 1.5 equivalents, on a molar basis, of di-tertbutyldicarbonate, relative to Compound (9). In other embodiments, the reaction of Scheme 11 is carried out with about 1.25 equivalents of di-tertbutyldicarbonate, on a molar basis, relative to Compound (9). In a specific embodiment, the reaction of Scheme 11 is carried out with about 1.1 equivalent, on a molar basis, of di-tertbutyldicarbonate, relative to Compound (9).

In certain embodiments, base used in the reaction of Scheme 11 is present at an initial level within the range of from about 1 to about 3 equivalents, or within the range of from about 1 to about 2.5 equivalents, on a molar basis, relative to Compound (9). In a specific embodiment, the reaction of Scheme 11 is carried out with about 2.2 equivalents of base, on a molar basis, relative to Compound (9). The base is any appropriate base, but may be selected from the group consisting of NaOH and KOH. In a specific embodiment, the base is NaOH.

The reaction of Scheme 11 is carried out at reduced pressure, atmospheric pressure or elevated pressure, i.e. greater than atmospheric pressure. In one embodiment, the reaction is carried out at atmospheric pressure. The reaction of Scheme 11 can be carried out in an inert atmosphere. In a specific, non-limiting embodiment, the reaction of Scheme 11 is carried out in a nitrogen atmosphere. In another specific, non-limiting embodiment, the reaction of Scheme 11 is carried out in an argon atmosphere.

The reaction of Scheme 11 is carried out, in certain embodiments, at a temperature within the range of from about 5° C. to about 100° C.; at a temperature within the range of from about 10° C. to about 75° C.; or at a temperature within the range of from about 15° C. to about 50° C. In a specific, non-limiting embodiment, the reaction of Scheme 11 is carried out at room temperature (i.e. from about 20° C. to about 25° C.).

Progress of the reaction of Scheme 11 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR. The reaction according to Scheme 11 is carried out, in one embodiment, until a starting material, Compound (9), is consumed or, in another embodiment, until the ratio of product, Compound (14), to starting material, Compound (9), remains essentially constant.

In certain embodiments, the reaction of Scheme 11 is carried out using a solution of Compound (9) in which the initial concentration of Compound (9) is within the range of from about 0.1 M to about 2 M, is within the range of from about 0.25 M to about 1.5 M, or is within the range of from about 0.5M to about 1.25 M. In a specific embodiment, the reaction of Scheme 11 is carried out using a solution of Compound (9) in which the initial concentration of Compound (9) is about 0.8 M.

Compound (14) formed in the reaction of Scheme 11 may be isolated and/or purified using methods, reagents and equipment known in the art. In certain embodiments, Compound (14) formed in the reaction of Scheme 11 is isolated by filtration, crystallization, chromatography, or extraction. In a specific embodiment, Compound (14) formed in the reaction of Scheme 11 is isolated by filtration.

4.2.12. Method for the Synthesis of Compound 13

(tert-butyl 4-cyano-4-phenylpiperidine-1-carboxylate)

In another embodiment, the present invention is directed toward methods for the synthesis of Compound (13) (tert-butyl 4-cyano-4-phenylpiperidine-1-carboxylate), comprising allowing Compound (16) (4-cyano-4-phenyl-piperidine: the free base of Compound (8) (4-cyano-4-phenyl-piperidinium chloride)) to react with Compound (12) (di-tertbutyldicarbonate), as depicted in Scheme 12, below.

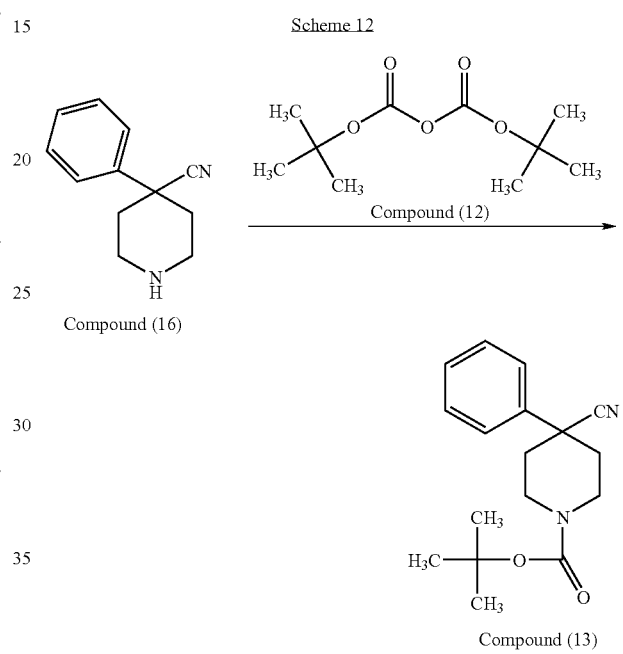

In certain embodiments, di-tertbutyldicarbonate used in the reaction of Scheme 12 is present at an initial level within the range of from about 1 to about 3 equivalents, or the range of from about 1 to about 2.5 equivalents on a molar basis, relative to Compound (16). In other embodiments, the reaction of Scheme 12 is carried out with about 1.5 equivalents, on a molar basis, of di-tertbutyldicarbonate, relative to Compound (16). In other embodiments, the reaction of Scheme 12 is carried out with about 1.25 equivalents of di-tertbutyldicarbonate, on a molar basis, relative to Compound (16). In a specific embodiment, the reaction of Scheme 12 could be carried out with about 1.1 equivalent, on a molar basis, of di-tertbutyldicarbonate, relative to Compound (16).

In certain embodiments, base used in the reaction of Scheme 12 is present at an initial level of within the range of from about 1 to about 3 equivalents, to within the range of from about 1 to about 2.5 equivalents, on a molar basis, relative to Compound (16). The base is any appropriate base, but may be selected from the group consisting of, for example, NaOH and KOH. In one, non-limiting aspect of this embodiment, the base can be NaOH.

The reaction of Scheme 12 is carried out at reduced pressure, atmospheric pressure or elevated pressure, i.e. greater than atmospheric pressure. In one embodiment, the reaction is carried out at atmospheric pressure. The reaction of Scheme 12 can be carried out in an inert atmosphere. In one, non-limiting aspect of this embodiment, the reaction of Scheme 12 is carried out in an argon atmosphere. In another non-limiting embodiment, the reaction of Scheme 12 is carried out in a nitrogen atmosphere.

The reaction of Scheme 12 is carried out, in certain embodiments, at a temperature within the range of from about 5° C. to about 100° C.; at a temperature within the range of from about 10° C. to about 75° C.; at a temperature within the range of from about 15° C. to about 50° C.; or at room temperature (i.e. from about 20° C. to about 25° C.).

Progress of the reaction of Scheme 12 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1H$ and $^{13}C$ NMR. The reaction according to Scheme 12 is carried out, in one embodiment, until a starting material, Compound (16), is consumed or, in another embodiment, until the ratio of product, Compound (13), to starting material, Compound (16), remains essentially constant.

In certain embodiments, the reaction of Scheme 12 is carried out using a solution of Compound (16) in which the initial concentration of Compound (16) is within the range of from about 0.1 M to about 2 M, is within the range of from about 0.25 M to about 1.5 M, or is within the range of from about 0.5M to about 1.25 M. In one, non-limiting aspect of this embodiment, the reaction of Scheme 12 could be carried out with an initial concentration of Compound (16) of about 0.8 M.

Compound (13) formed in the reaction of Scheme 12 may be isolated and/or purified using methods, reagents and equipment known in the art. In certain embodiments, Compound (13) formed in the reaction of Scheme 12 is isolated by filtration, crystallization, chromatography, or extraction.

4.2.13. Alternative Method for the Synthesis of Compound (14)

(tert-butyl 4-phenyl-4-(1H-tetrazol-5-yl)piperidine-1-carboxylate)

In one embodiment, the present invention relates to methods for making Compound (14) (tert-butyl 4-phenyl-4-(1H-tetrazol-5-yl)piperidine-1-carboxylate), comprising allowing Compound (13) (tert-butyl 4-cyano-4-phenylpiperidine-1-carboxylate) to react with sodium azide in the presence of a zinc salt, such as but not limited to a zinc halide (e.g. $ZnBr_2$, $ZnCl_2$, and $ZnI_2$) or another suitable zinc salt such as $Zn(ClO_4)_2$ or $Zn(CF_3SO_3)_2$, as depicted in Scheme 13 below:

Scheme 13

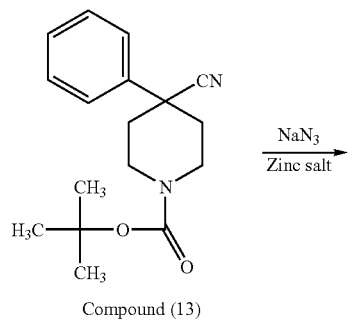

Compound (13)

-continued

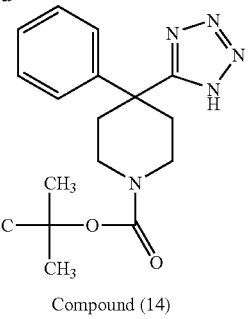

Compound (14)

In certain optional embodiments, the phenyl moiety, which is attached to the 4-position of the piperidine ring of Compound (13), is substituted with one or more $R^2$ groups, where $R^2$ is as defined above.

The reaction of Scheme 13 is preferably carried out in a solvent comprising a polar aprotic solvent. Examples of suitable polar aprotic solvents that can be used in the reaction of Scheme 13 include, but are not limited to N-methyl-pyrrolidone, dimethyl formamide, dimethyl acetamide, acetonitrile, and dimethyl sulfoxide. In certain embodiments, the solvent is N-methyl-pyrrolidone or dimethyl acetamide. In one, non-limiting aspect of this embodiment, the solvent is N-methyl-pyrrolidone. In another specific embodiment, the polar aprotic solvent is acetonitrile.

In certain embodiments, the solvent used in the reaction of Scheme 13 is a mixture of a suitable polar aprotic solvent and water. In such embodiments, the ratio of polar aprotic solvent to water can be within the range of from about 50:1 to about 2:1 (v/v) (polar aprotic solvent:water); within the range of from about 20:1 to about 4:1 (polar aprotic solvent:water); or within the range of from about 15:1 to about 10:1 (polar aprotic solvent:water).

In certain embodiments, the reaction of Scheme 13 is carried out with an initial amount of zinc salt within the range of from about 1 to about 5 equivalents, or within the range of from about 2 to about 4 equivalents, on a molar basis, relative to Compound (13). In still other embodiments, the reaction of Scheme 13 is carried out with about 3 equivalents, on a molar basis, of zinc salt, relative to Compound (13). The zinc salt may be selected from the group consisting of zinc(halide)$_2$ including $ZnBr_2$, $ZnCl_2$, and $ZnI_2$, as well as any other suitable zinc salt such as e.g. $Zn(ClO_4)_2$ or $Zn(CF_3SO_3)_2$. In one, non-limiting aspect of this embodiment, the zinc salt can be $ZnBr_2$. Zinc salts are commercially available from, e.g., Aldrich Chemical Co., Milwaukee, Wis.

In certain embodiments, the reaction of Scheme 13 is carried out with an initial amount of sodium azide within the range of from about 1 to about 5 equivalents, or within the range of from about 2 to about 4 equivalents, on a molar basis, relative to Compound (13). In one, non-limiting aspect of this embodiment, the reaction of Scheme 13 can be carried out with about 4 equivalents, on a molar basis, of sodium azide, relative to Compound (13).

In certain embodiments, Compound (13) is provided as a salt, e.g. the hydrochloride salt, which can be converted to the free amine, using procedures known in the art, prior to reaction with sodium azide. For example, the hydrochloride salt of Compound (13) is dissolved in a suitable organic solvent such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g. over anhydrous sodium sulfate, and then evaporated to provide Compound (13) as the free amine.

The reaction of Scheme 13 can be carried out at reduced pressure, atmospheric pressure or elevated pressure, i.e. greater than atmospheric pressure. In one embodiment, the reaction is carried out at atmospheric pressure. In certain embodiments, the reaction of Scheme 13 is carried out in an inert atmosphere. In one non-limiting aspect of this embodiment, the reaction of Scheme 13 is carried out under a nitrogen atmosphere. In another non-limiting aspect of this embodiment, the reaction of Scheme 13 is carried out under an argon atmosphere.

The reaction of Scheme 13 is carried out, in certain embodiments, at a temperature within the range of from about 100° C. to about 200° C.; at a temperature within the range of from about 120° C. to about 150° C.; or at a temperature within the range of from about 130° C. to about 140° C.

Progress of the reaction of Scheme 13 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR. The reaction according to Scheme 13 is carried out, in one embodiment, until a starting material is consumed or, in another embodiment, until the ratio of product, Compound (14) to starting material, Compound (13) remains essentially constant.

In certain embodiments, the reaction of Scheme 13 is carried out using a solution of Compound (13) in which the initial concentration of Compound (13) is in the range of from about 0.05 M to about 1.0 M, or is in the range of from about 0.1 M to about 0.5 M. In one, non-limiting aspect of this embodiment, the initial concentration of Compound (13) in the reaction of Scheme 4 can be about 0.25 M.

Compound (14) formed in the reaction of Scheme 13 may be isolated and/or purified using methods, reagents and equipment known in the art.

4.2.14. Synthesis of Compounds of Formula X

In another embodiment, the present invention relates to methods for making compounds according to Formula X (e.g compound (15)), comprising allowing Compound (14) (tert-butyl 4-phenyl-4-(1H-tetrazol-5-yl)piperidine-1-carboxylate) to react with an alkylating agent according to Formula II in the presence of a non-nucleophilic base, as depicted in Scheme 14 below:

Scheme 14

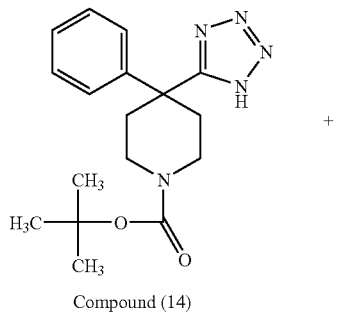

Compound (14)

+

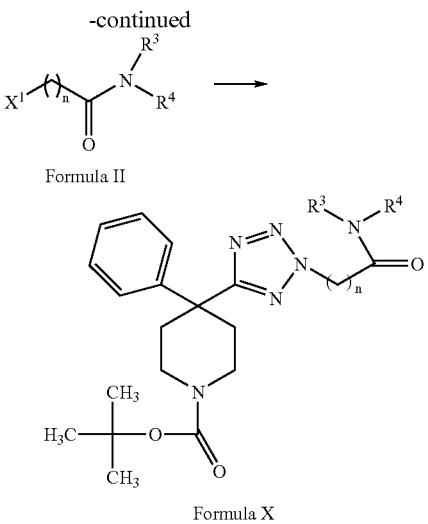

Formula II

Formula X where n is an integer in the range of 1 to 4, $R^3$ and $R^4$ are each independently H or —($C_1$-$C_4$ alkyl), and $X^1$ is —Br, —Cl, or —I. In certain embodiments, the phenyl moiety attached to the 4-position of the piperidine ring of Compound (14), and, therefore, of a compound according to Formula X formed therefrom, is, optionally, substituted with one or more $R^2$ groups, where $R^2$ is as defined above.

The reaction of Scheme 14 is preferably carried out in a solvent comprising a polar aprotic solvent. Examples of suitable polar aprotic solvents that can be used in the reaction of Scheme 14 include, but are not limited to acetone, N-methyl pyrrolidone, dimethyl formamide, dimethyl acetamide, 1,4-dioxane, acetonitrile, and dimethyl sulfoxide. In a specific embodiment, the solvent is acetone. In another specific embodiment, the polar aprotic solvent is acetonitrile. In still another specific embodiment, the polar aprotic solvent is 1,4-dioxane.

In certain embodiments, Compound (14) is present in the reaction of Scheme 14 at an initial concentration within the range of from about 0.1 M to about 0.8 M, or at an initial concentration within the range of from about 0.2 M to about 0.6 M. In a specific embodiment, Compound (14) is present in the reaction of Scheme 5 at an initial concentration of about 0.4 M.

The reaction of Scheme 14 can be carried out in the presence of any suitable non-nucleophilic base such as, but not limited to, triethylamine, diisopropylethylamine, sodium carbonate, potassium carbonate, cesium carbonate, or 2,3,4,6,7,8,9,10-octahydro-pyrimido[1,2-α]azepine (DBU). In certain embodiments, the non-nucleophilic base is triethylamine, sodium carbonate, or potassium carbonate. In certain embodiments, the reaction may further comprise a catalytic amount of 4-DMAP in order to accelerate the rate of the reaction. In certain embodiments, the non-nucleophilic base is present in the reaction of Scheme 14 at a level within the range of from about 0.5 equivalent to about 3.0 equivalents, within the range of from about 0.75 equivalent to about 2.0 equivalents, or within the range of from about 1.0 equivalent to about 1.5 equivalents, on a molar basis relative to the initial concentration of Compound (14). In a specific embodiment, the non-nucleophilic base is potassium carbonate. In a specific embodiment, the reaction of Scheme 14 is carried out with about 1 equivalent, on a molar basis, of the non-nucleophilic base, relative to the initial concentration of Compound (14).

In certain embodiments, the reaction of Scheme 14 is carried out with an alkylating agent present at a level within the range of from about 0.80 equivalent to about 1.5 equivalents, within the range of from about 0.85 equivalents to about 1.2 equivalents, or within the range of from about 0.95 equivalent to about 1.1 equivalents, on a molar basis, relative to the initial amount of Compound (14) present in the reaction according to Scheme 14. In a specific embodiment, the reaction of Scheme 14 is carried out with about 1 equivalent, on a molar basis, of alkylating agent, relative to the initial amount of Compound (14) present in the reaction according to Scheme 14. Any appropriate alkylating agent, including those according to Formula II, can be used in the reaction of Scheme 14, which will provide the desired product according to Formula X. In certain embodiments the alkylating agent according to Formula II is a haloalkylamide such as, but not limited to bromoacetamide, chloroacetamide, or iodoacetamide. In another, non-limiting, embodiment, the alkylating agent is acrylamide. In certain embodiments, the alkylating agent according to Formula II is bromoacetamide or chloroacetamide. In a specific embodiment, the alkylating agent according to Formula II is bromoacetamide (compound (3)), while in another specific embodiment the alkylating agent according to Formula II is chloroacetamide (compound (11)).

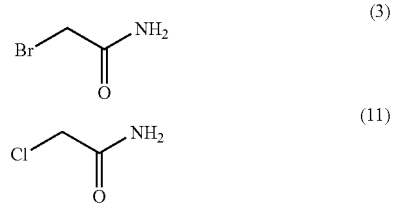

(3)

(11)

In certain embodiments alkylation is carried out in the presence of a catalytic amount of iodide. The iodide used in this aspect of the reaction of Scheme 14 can be added in the form of a metal salt ($MI_p$), where M is a Group I or Group II metal. p=1 where M is a Group I metal. p=2, where M is a Group II metal. In certain embodiments, iodide is provided as the LiI, NaI, KI, CsI, $CaI_2$, $MgI_2$, or $SrI_2$ salt. In certain embodiments, iodide salts useful in the reaction of Scheme 14 include potassium iodide, sodium iodide, lithium iodide, and cesium iodide, as well as tetralkyl-ammonium iodides. In certain embodiments, the iodide salt is NaI or KI. When used, the iodide salt is present in the reaction of Scheme 14 at an initial level within the range of from about 0.01 equivalent to about 2.0 equivalents, within the range of from about 0.05 equivalent to about 1.0 equivalents, within the range of from about 0.1 equivalent to about 0.6 equivalent, or within the range of from about 0.1 equivalent to about 0.25 equivalent, on a molar basis, relative to the initial amount of Compound (14).

The reaction of Scheme 14 is carried out, in certain embodiments, at a temperature within the range of from about 20° C. to about 100° C.; at a temperature within the range of from about 25° C. to about 80° C.; or at a temperature within the range of from about 30° C. to about 70° C. In a specific embodiment, the reaction of Scheme 14 is carried out at a temperature within the range of from about 40° C. to about 50° C.

The reaction of Scheme 14 is carried out for a time sufficient to convert Compound (14) to a compound of Formula X. The reaction according to Scheme 14 is carried out, in one embodiment, until a starting material (e.g. Compound (14)) is consumed or, in another embodiment, until the ratio of product (a compound according to Formula X), to starting material (Compound (14)) remains essentially constant. Typically, a time sufficient for the reaction of Scheme 14 is within the range of from about 4 hours to about 48 hours, from about 8 hours to about 36 hours, or from about 12 hours to about 24 hours. In a specific embodiment, the reaction according to Scheme 14 is carried out for about 16 hours.

The reaction of Scheme 14 can be carried out at reduced pressure, atmospheric pressure or elevated pressure, i.e. greater than atmospheric pressure. In one embodiment, the reaction is carried out at atmospheric pressure. In certain embodiments, the reaction of Scheme 14 is carried out in an inert atmosphere. In one non-limiting aspect of this embodiment, the reaction of Scheme 14 is carried out under a nitrogen atmosphere. In another non-limiting aspect of this embodiment, the reaction of Scheme 14 is carried out under an argon atmosphere.

Progress of the reaction of Scheme 14 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), nuclear magnetic resonance spectroscopy ("NMR"), such as $^1H$ and $^{13}C$ NMR.

Compounds of Formula X synthesized according to Scheme 14 may be isolated and/or purified using methods, reagents, and equipment well known in the art.

4.2.15. Synthesis of Compounds of Formula IV

In another embodiment, the present invention relates to methods for making compounds according to Formula IV (e.g. compound (5)), comprising the step of deprotecting the piperidine nitrogen of a compound according to Formula X, as depicted in Scheme 15 below:

Scheme 15

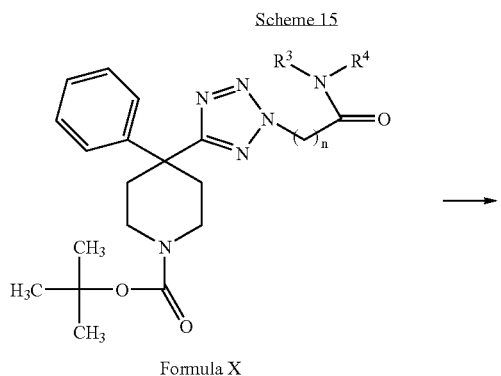

Formula X

-continued

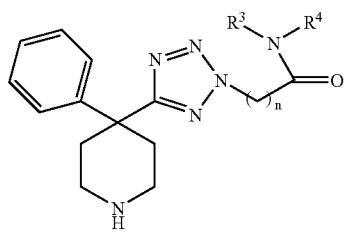

Formula IV where n is an integer in the range of 1 to 4, and $R^3$ and $R^4$ are each independently H or —($C_1$-$C_4$ alkyl). In certain embodiments, the phenyl moiety, which is attached to the 4-position of the piperidine ring of a compound according to Formula X, and, therefore, of a compound according Formula IV formed therefrom, is substituted with one or more $R^2$ groups, where $R^2$ is as defined above.

The reaction of Scheme 15 is preferably carried out in a solvent such as but not limited to methylene chloride ($CH_2Cl_2$) or 1,2 dichloroethane ($ClCH_2CH_2Cl$). In a specific embodiment, the solvent is methylene chloride.

In the reaction of Scheme 15, the compound of Formula X is present at an initial concentration within the range of from about 0.025 M to about 0.8 M, within the range of from about 0.05 M to about 0.4 M, or within the range of from about 0.1 M to about 0.2 M.

The reaction of Scheme 15 is also carried out, in certain embodiments, in the presence of a suitable acid catalyst such as, but not limited to, trifluoracetic acid. Other methods known in the art for removal of the Boc moiety may also be used, including, for example, reaction in 3M $HCl_{(aq)}$/ethyl acetate at 25° C.

In certain embodiments, the acid catalyst used in the reaction of Scheme 15 is present at an initial level within the range of from about 1 equivalent to about 4 equivalents, on a molar basis, relative to the initial concentration of the compound of Formula X. In a specific embodiment, the acid catalyst used in the reaction of Scheme 15 is present at an initial level within a range of from about 2 equivalents to about 3 equivalents, on a molar basis, relative to the initial concentration of the compound of Formula X.

In certain embodiments, a compound according to Formula X is dissolved in the solvent under an inert atmosphere, such as but not limited to an argon atmosphere. In another aspect of this embodiment, the vessel containing the reaction mixture, which comprises a solution of a compound according to Formula X and the acid catalyst, is purged with argon. The reaction according to Scheme 15 is then allowed to run in the presence of argon gas, at a pressure within the range of from about atmospheric pressure (about 14.7 psi (lbs./in²)) to about 500 psi, at a pressure within the range of from about atmospheric pressure (about 14.7 psi) to about 100 psi, or at a pressure within the range of from about atmospheric pressure (about 14.7 psi) to about 25 psi.

In certain embodiments, the reaction according to Scheme 15 is run at a temperature within the range of from about 5° C. to about 100° C.; at a temperature within the range of from about 10° C. to about 75° C.; or at a temperature within the range of from about 15° C. to about 30° C.

The reaction of Scheme 15 is carried out for a time sufficient to convert a compound of Formula X to a compound of Formula IV. The reaction according to Scheme 15 is carried out, in one embodiment, until the starting material (a compound of Formula X) is consumed or, in another embodiment, until the ratio of product (a compound of Formula IV) to starting material (a compound of Formula X) remains essentially constant. Typically, a time sufficient for the reaction of Scheme 15 is within the range of from about 1 hour to about 48 hours, within the range of from about 2 hours to about 36 hours, or within the range of from about 4 hours to about 24 hours. In a specific embodiment, the reaction of Scheme 6 is carried out for about 16 hours.

Progress of the reaction of Scheme 15 can be monitored using conventional analytical techniques, including but not limited to liquid chromatography in conjunction with mass spectroscopy ("LC/MS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1$H and $^{13}$C NMR.

Compounds of Formula IV synthesized according to Scheme 15 may be isolated and/or purified using methods, reagents, and equipment known in the art.

4.2.16. Method for Making Compound (7) According to Schemes 11-15

In another embodiment, the present invention is directed toward the synthesis of a 4-Tetrazolyl-4-phenylpiperidine Compound, in which the methods and reagents of Schemes 11-15 above, can be combined to provide a method for the synthesis of a compound according to Formula I. For example, as depicted in Scheme 16 below, Compound (7), which is a compound according to Formula I, is synthesized according to the methods and conditions described in Sections 4.2.11 to 4.2.15, above.

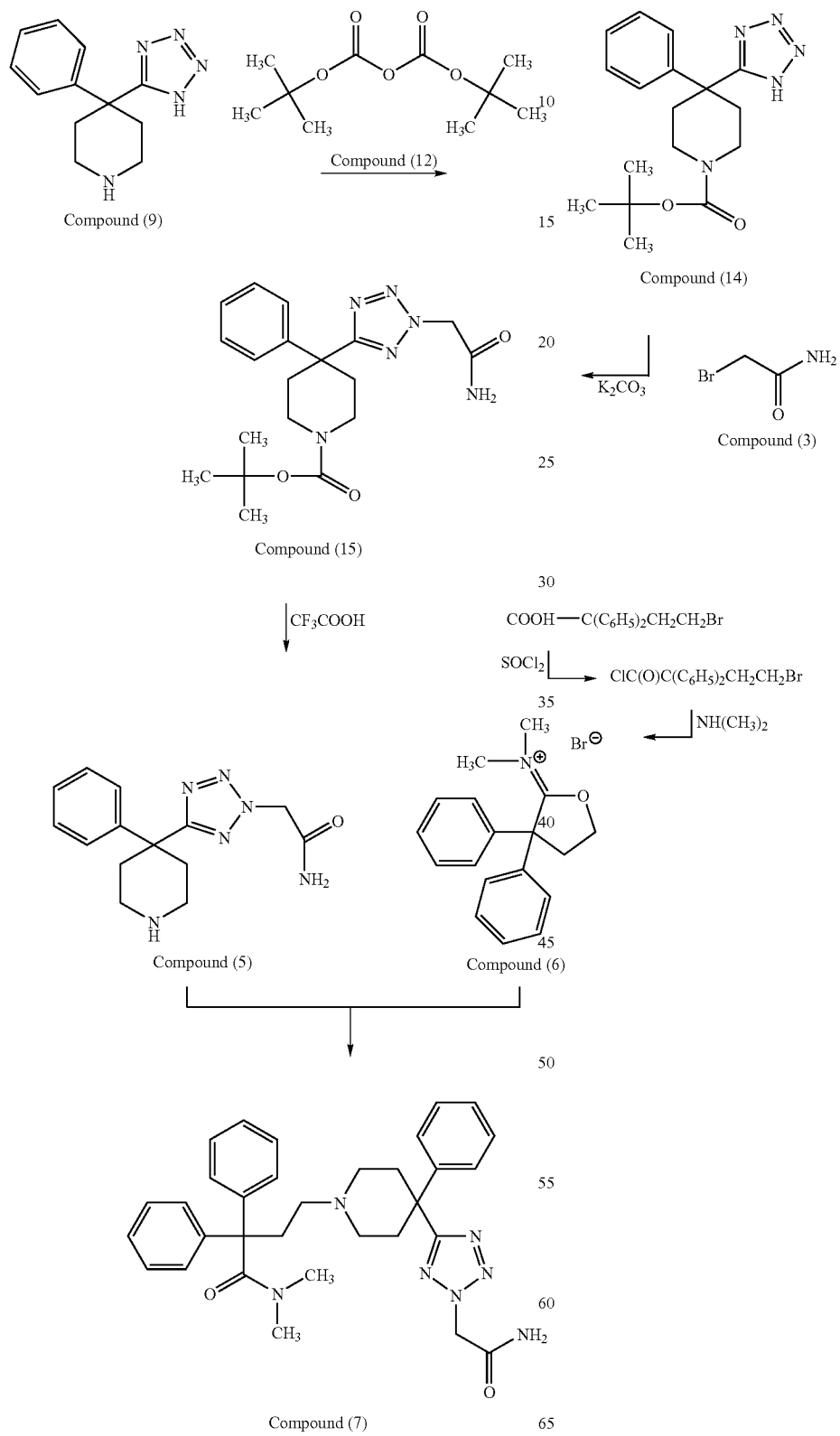
Scheme 16

4.2.17. Method for Making Compound (18)

5-benzyl-2H-tetrazole

In another embodiment, the present invention relates to a method for the synthesis of Compound (18) (5-benzyl-2H-tetrazole), comprising allowing Compound (17) (2-phenylacetonitrile or benzyl nitrile) (which is commercially available) to react with sodium azide in the presence of triethylamine hydrochloride, as depicted in Scheme 17 below:

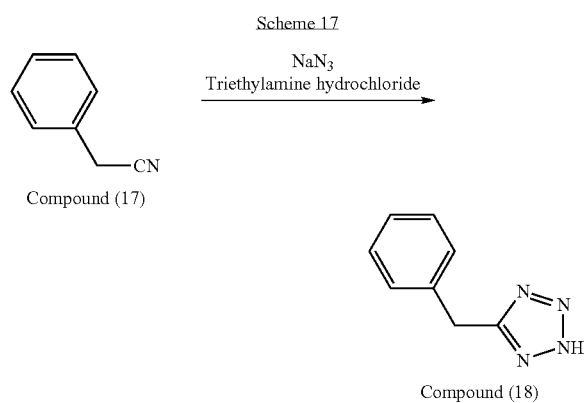

In one embodiment, Compound (17), which is commercially available, is treated with sodium azide and triethylamine hydrochloride in toluene at 95° C.-100° C., under an inert gas (e.g argon) for 16 hours. In other embodiments, the nitrile (Compound (17)) can be converted to the corresponding tetrazole (Compound (18)), according to the methods described in Schemes 1, 7 and 13, above, and Example 1, Section 5.1, and Example 17, Section 5.17, below. In further aspects of this embodiment, the phenyl moiety of Compound (17) is optionally substituted with one or more $R^2$ groups, thereby providing the corresponding compounds of Formula I comprising such $R^2$ moieties.

4.2.18. Method for Making Compound (20)

5-benzyl-2-(2-phenylpropan-2-yl)-2H-tetrazole

In another embodiment, the present invention relates to a method for the synthesis of Compound (20) (5-benzyl-2-(2-phenylpropan-2-yl)-2H-tetrazole), comprising allowing Compound (18) to react with Compound (19) (1-(prop-1-en-2-yl)benzene), as depicted in Scheme 18 below:

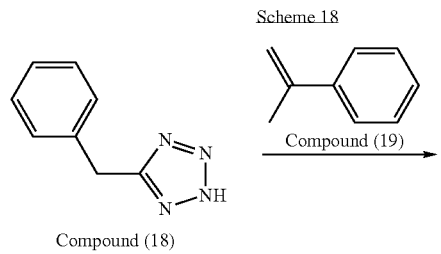

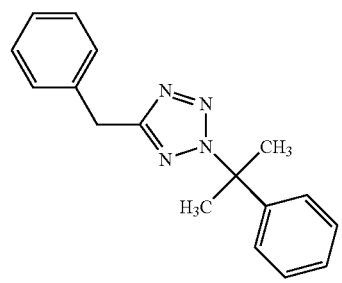

Compound (20)

In this manner, Compound (18) can be protected essentially exclusively at the 2-position by reaction with Compound (19) and trichloroacetic acid in chloroform under, for example, the conditions provided in Section 5.17, Example 17, below.

In other, alternative embodiments, the tetrazole moiety of Compound (18), can be protected by reaction with (a) trityl alcohol in toluene at reflux temperature, (b) trityl-protected 2-bromoacetamide and $K_2CO_3$ in acetonitrile at reflux temperature, (c) toluenesulfonylchloride and $K_2CO_3$ in acetonitrile at reflux temperature, (d) 2,4-dinitrofluorobenzene and $K_2CO_3$ in acetonitrile at room temperature, or (e) benzene sulfonyl chloride and $K_2CO_3$ in acetonitrile at reflux temperature.

4.2.19. Method for Synthesis of Compounds of Formula XII

In another embodiment, the present invention is directed toward methods for the synthesis of hindered tetrazole compounds according to Formula XII (e.g. Compound (22) and Compound (24)), comprising allowing Compound (20) (5-benzyl-2-(2-phenylpropan-2-yl)-2H-tetrazole) to react with a compound according to Formula XI, as described in Sections 5.11 and 5.19, below, and depicted in Scheme 19:

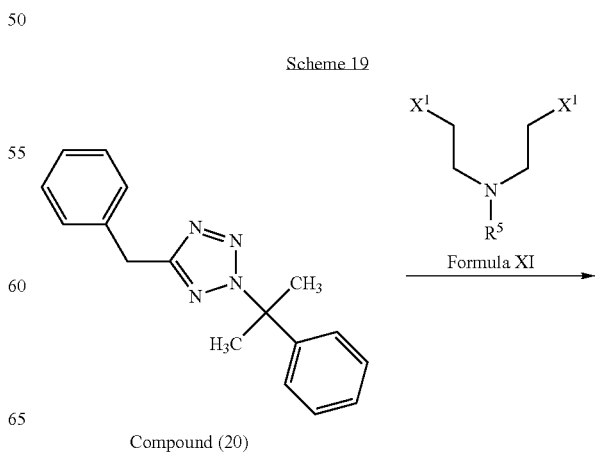

-continued

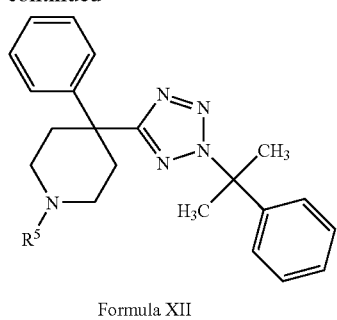

Formula XII wherein each $X^1$ is independently selected from the group consisting of Cl, Br, or I and $R^5$ is a Nitrogen protecting group that can be selected from, but not limited to the group consisting of

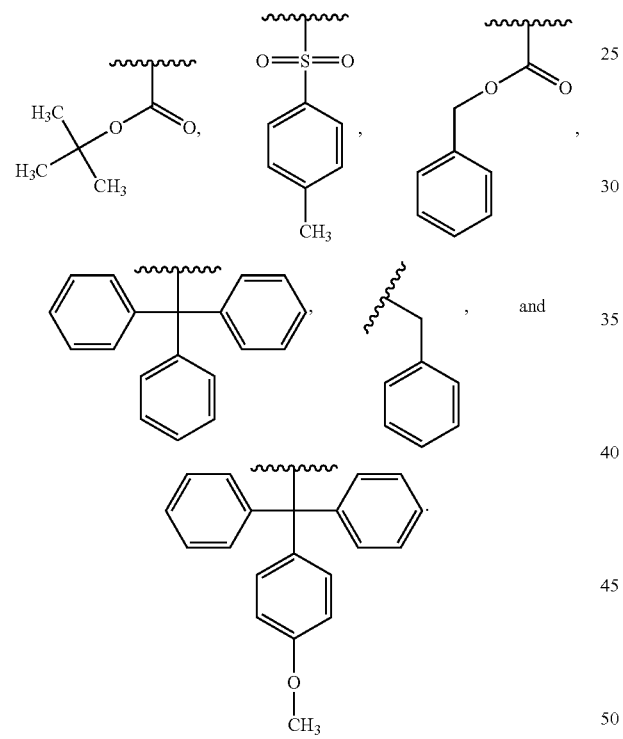

In another embodiment, $R^5$ is

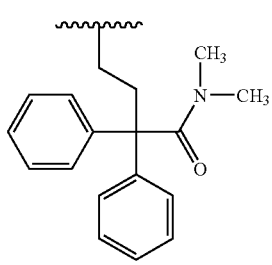

and the compound of Formula XI is Compound (35)

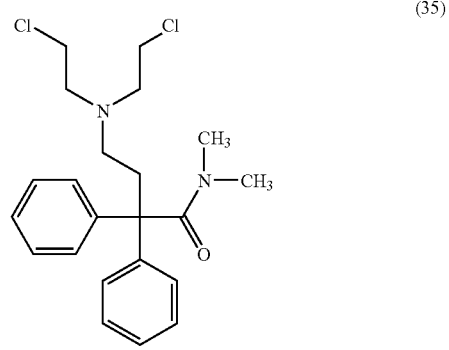

In a specific embodiment, Compound (20) is reacted with Compound (21) using two equivalents of n-butyllithium in diethyl ether, as depicted in Scheme 20, below, to provide boc-protected piperidine Compound (22):

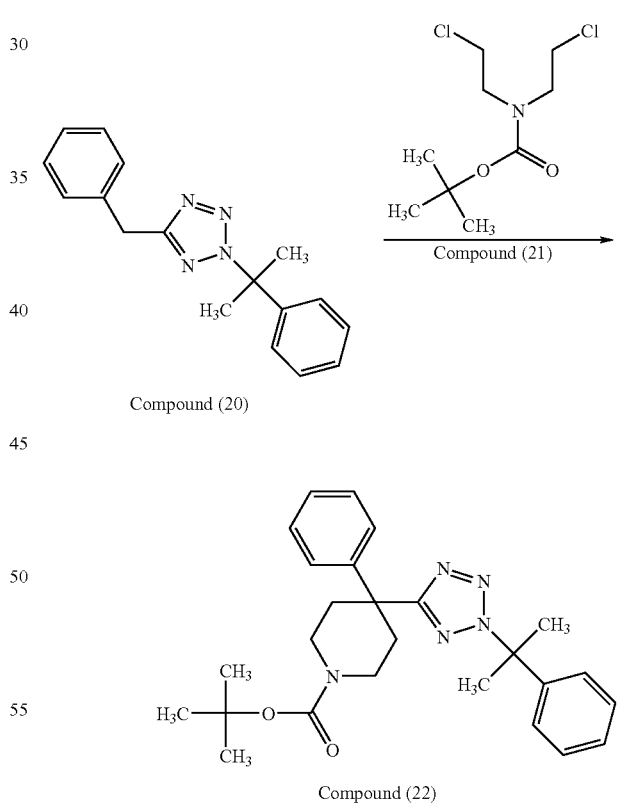

In another specific embodiment, Compound (20) is allowed to react with Compound (23) (which is commercially available from Acros, Morris Plains, N.J.) using two equivalents of n-butyllithium in diethyl ether, as depicted in Scheme 21, below, to provide tosyl-protected piperidine Compound (24):

Scheme 21

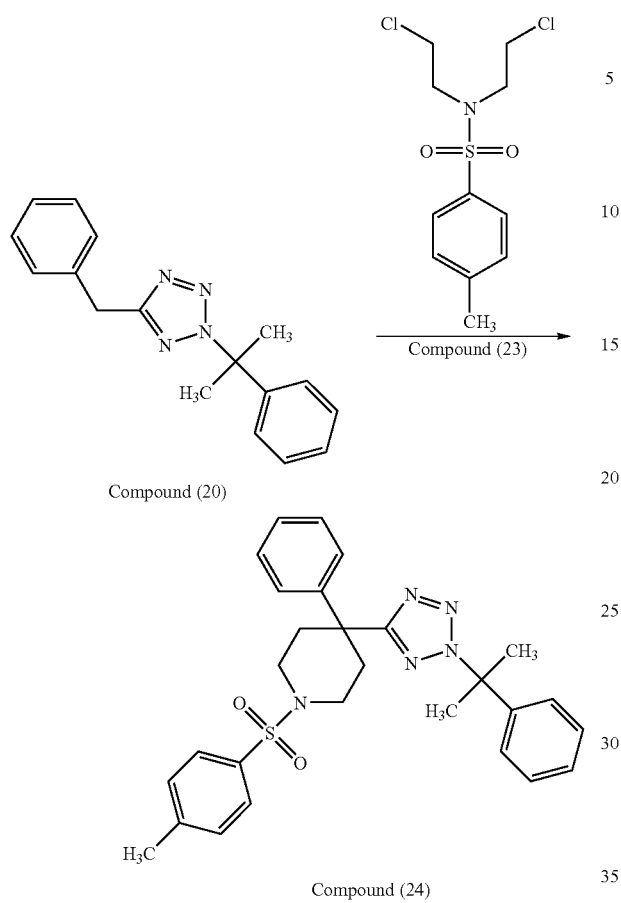

Preparation of compounds according to Formula XI, and methods for their use are described in Chambers et al. (J. Med. Chem. (1992) 35: 2033-39), as well as in Section 4.2.25, below.

4.2.20. Method for Synthesis of Compounds of Formula XIII

In another embodiment, the present invention is directed toward methods for the synthesis of compounds according to Formula XIII (e.g. Compound (14) and Compound (25)), comprising removal of the protecting group ($R^5$) of Compounds of Formula XII, as depicted in Scheme 22 below:

Scheme 22

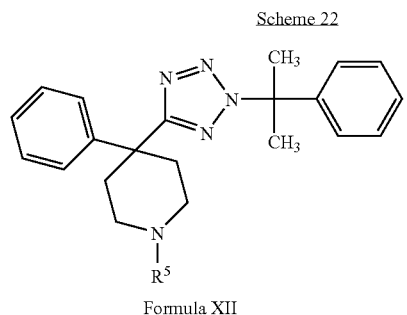

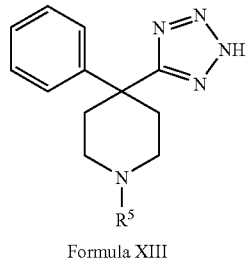

Formula XIII

In a specific embodiment, the cumyl protecting group of Compound (22) can be removed in ethanol, in the presence of potassium formate and Pd/C, to provide Compound (14) carrying the deprotected tetrazole moiety as depicted in Scheme 23:

Scheme 23

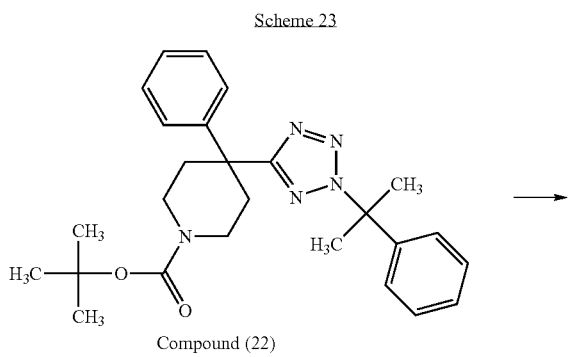

In another specific embodiment, the cumyl protecting group of Compound (24) can be removed in ethanol, in the presence of potassium formate and Pd/C, to provide Compound (25) carrying the deprotected tetrazole moiety as described in Section 5.20, Example 20 below, and as depicted in Scheme 24:

Scheme 24

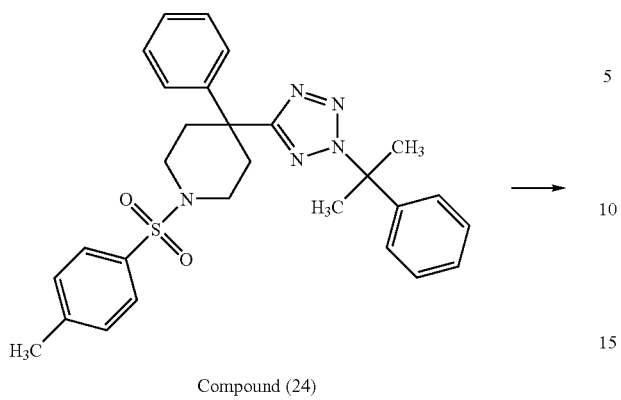

Compound (24)

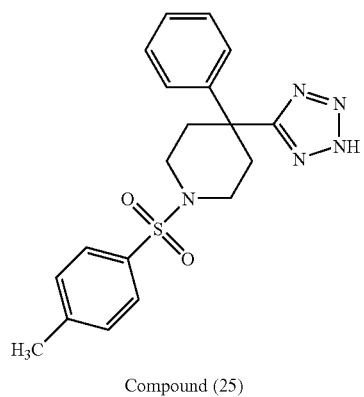

Compound (25)

In a further aspect of this embodiment, the R⁵ moiety is a benzyl group and both the cumyl and the R⁵ (benzyl) protecting groups can be removed from a compound of Formula XII, to provide Compound (9) as a product. Compound (9), in turn can be converted to a compound of Formula I, (e.g Compound (7)) according to Scheme 10 (via the methods of Schemes 8 and 9, as described above) or according to Scheme 16 (via the methods of Schemes 11, 14, 15, and 30).

4.2.21. Method for Synthesis of Compounds of Formula XIV

In another embodiment, the present invention is directed toward methods for the synthesis of compounds according to Formula XIV (e.g Compound (15) and Compound (26)), comprising reacting a compound of Formula XIII with a compound of Formula II, as depicted in Scheme 25 below:

Scheme 25

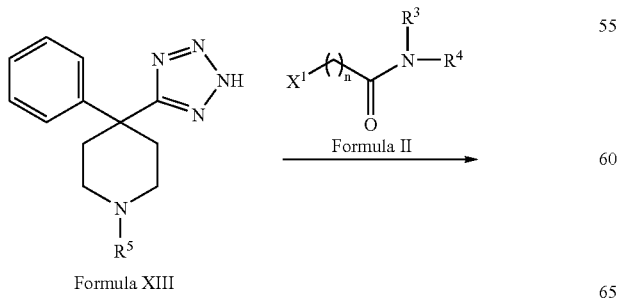

-continued

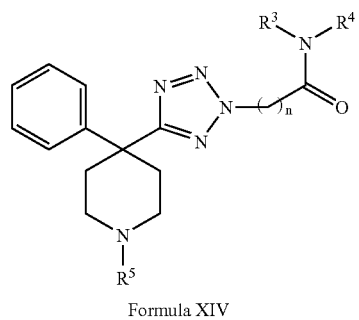

Formula XIV

In a specific embodiment, the present invention is directed toward the synthesis of a compound of Formula X, which comprises the step of reacting Compound (14) with a compound of Formula II, as indicated in Scheme 26, below:

Scheme 26

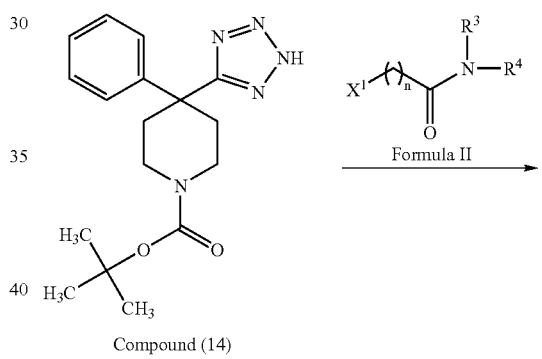

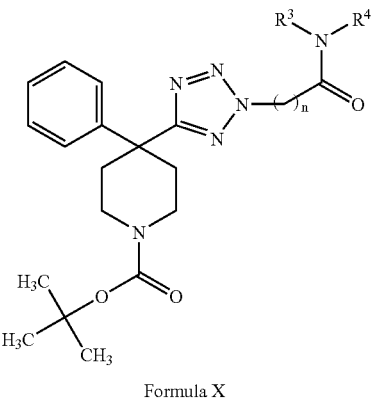

Formula X

In another specific embodiment, the present invention is directed toward the synthesis of a compound of Formula XV, which comprises the step of reacting Compound (25) with a compound of Formula II, as indicated in Scheme 27, below:

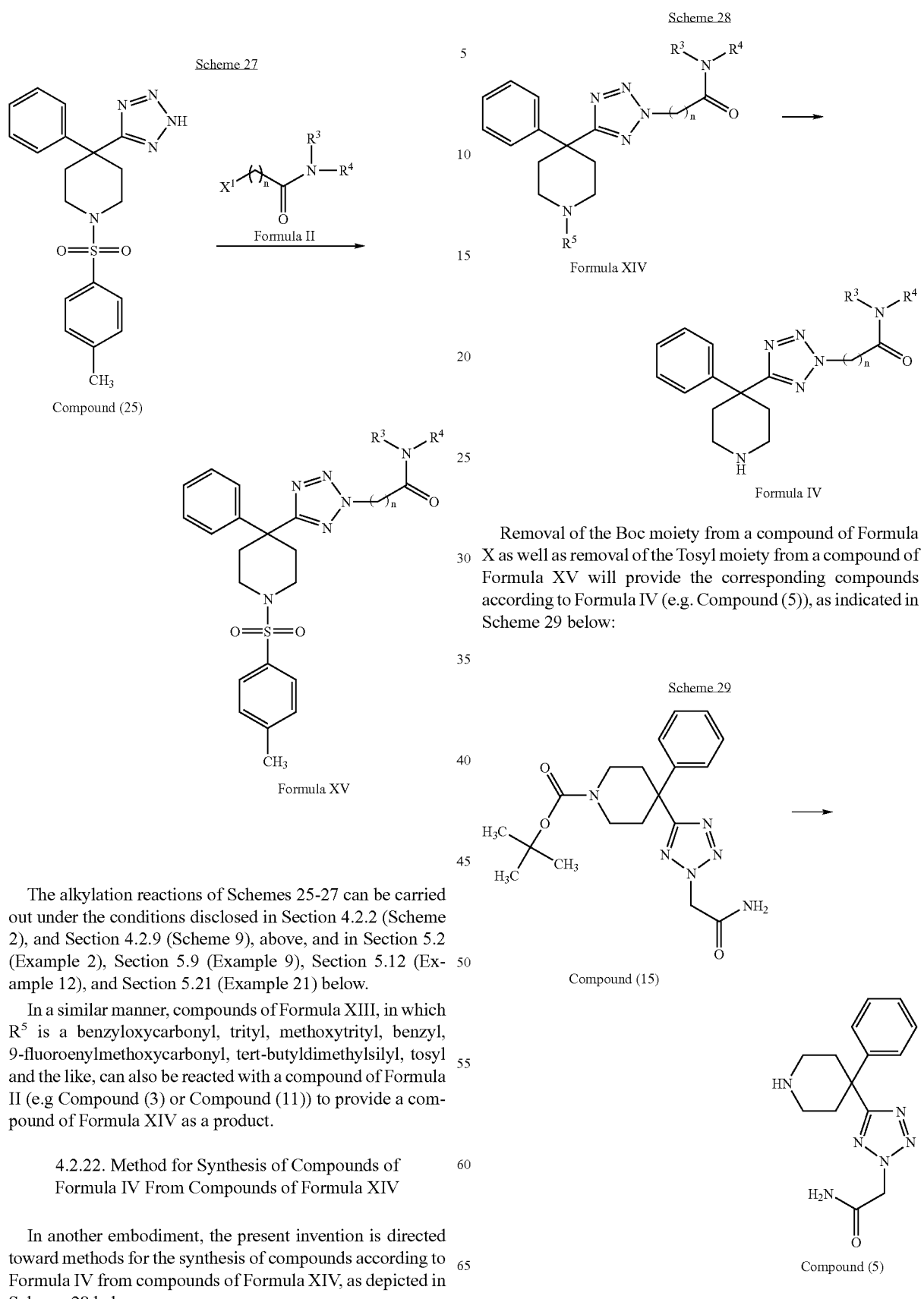

The alkylation reactions of Schemes 25-27 can be carried out under the conditions disclosed in Section 4.2.2 (Scheme 2), and Section 4.2.9 (Scheme 9), above, and in Section 5.2 (Example 2), Section 5.9 (Example 9), Section 5.12 (Example 12), and Section 5.21 (Example 21) below.

In a similar manner, compounds of Formula XIII, in which $R^5$ is a benzyloxycarbonyl, trityl, methoxytrityl, benzyl, 9-fluoroenylmethoxycarbonyl, tert-butyldimethylsilyl, tosyl and the like, can also be reacted with a compound of Formula II (e.g Compound (3) or Compound (11)) to provide a compound of Formula XIV as a product.

4.2.22. Method for Synthesis of Compounds of Formula IV From Compounds of Formula XIV In another embodiment, the present invention is directed toward methods for the synthesis of compounds according to Formula IV from compounds of Formula XIV, as depicted in Scheme 28 below:

Removal of the Boc moiety from a compound of Formula X as well as removal of the Tosyl moiety from a compound of Formula XV will provide the corresponding compounds according to Formula IV (e.g. Compound (5)), as indicated in Scheme 29 below:

-continued

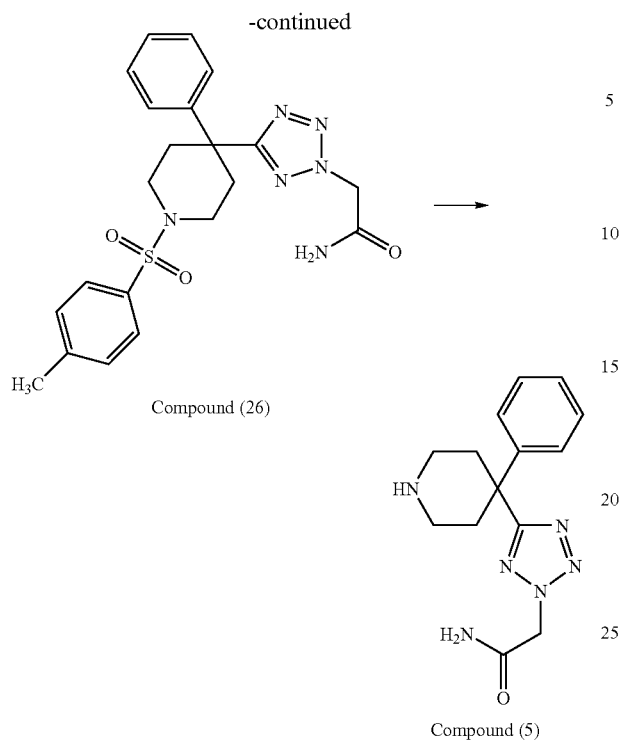

Compound (26)

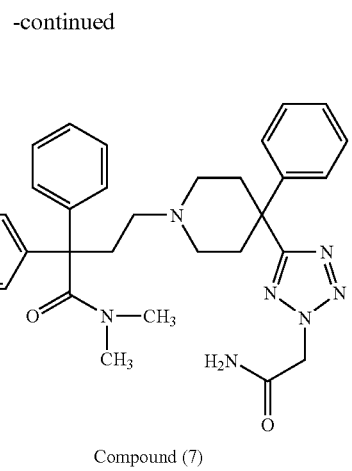

Compound (7)

In a specific embodiment, the Boc protecting group of Compound (15) can be removed, for example, with trifluoroacetic acid in dichloromethane, to provide Compound (5), as described in Section 4.2.15 (Scheme 15), above. Similarly, the Tosyl protecting group of Compound (26) can be removed with a mineral acid such as $H_2SO_4$, HCl or HBr to provide Compound (5). In a specific embodiment, the Tosyl protecting group of Compound (26) is removed with $H_2SO_4$.

4.2.23. Method for Synthesis of Compounds of Formula I From Compounds of Formula IV The present invention is also directed toward the synthesis of a compound of Formula I where $R^1$ is —$(CH_2)_n C(O)N(R^3)(R^4)$ (e.g. Compound (7)) from a compound of Formula IV (e.g. Compound (5)) by reacting the compound of Formula IV, with a compound of Formula VII (e.g. Compound (6)), as depicted in Scheme 5 above, and Scheme 30, below:

Scheme 30

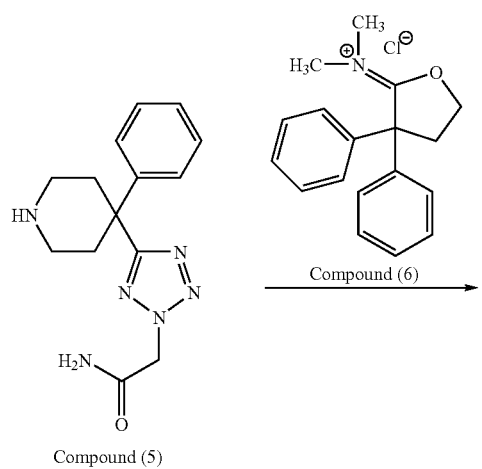

The reaction of Scheme 30 can be carried out under the conditions provided in Sections 4.5.5 above (Scheme 5) as well as those described in Section 5.5 (Example 5), below.

4.2.24. Method for Making Compound (7) According to Schemes 17-30

In another specific embodiment, the present invention is directed toward the synthesis of a 4-Tetrazolyl-4-phenylpiperidine Compound, in which methods and reagents of Schemes 17-30 above, can be combined to provide an illustrative method for the synthesis of a compound according to Formula I. For example, as depicted in Scheme 31 below, Compound (7), which is a compound according to Formula I, is synthesized according to methods and conditions described in Sections 4.2.17 to 4.2.23, above.

According to Scheme 31, Compound (7), is synthesized starting with commercially-available Compound (17) (2-cyanobenzene (Aldrich, Milwaukee, Wis.)). In general, Compound (17) (benzyl cyanide) is converted into Compound (18) (5-benzyl-1-H-tetrazole) using sodium azide, triethylamine HCl, and toluene as solvent. Reagents are combined and heated to 100° C. for 16 hours. Subsequent acid/base workup affords the pure tetrazole, Compound (18), as a white crystalline solid. Protection of the tetrazole moiety of Compound (18), can be accomplished using any one of a variety of protecting groups. In a specific embodiment, protection of the tetrazole moiety of Compound (18) is accomplished by reaction with alpha-methyl styrene to provide the cumyl-protected tetrazole, Compound (20). Piperidine ring formation is achieved using n-BuLi in diethyl ether with the requisite N-protected bis-dichloroethyl amine substrate (e.g. Compound (23)) to produce Compound (24). Deprotection of the tetrazole moiety of Compound (24) is accomplished using standard hydrogenolysis conditions (potassium formate, Pd/C, EtOH, heat) affording Compound (25). Alkylation of Compound (25) with 2-chloroacetamide or 2-bromoacetamide affords Compound (26). Deprotection of Compound (26), provides Compound (5), which is then allowed to react with compound (6), to provide Compound (7).

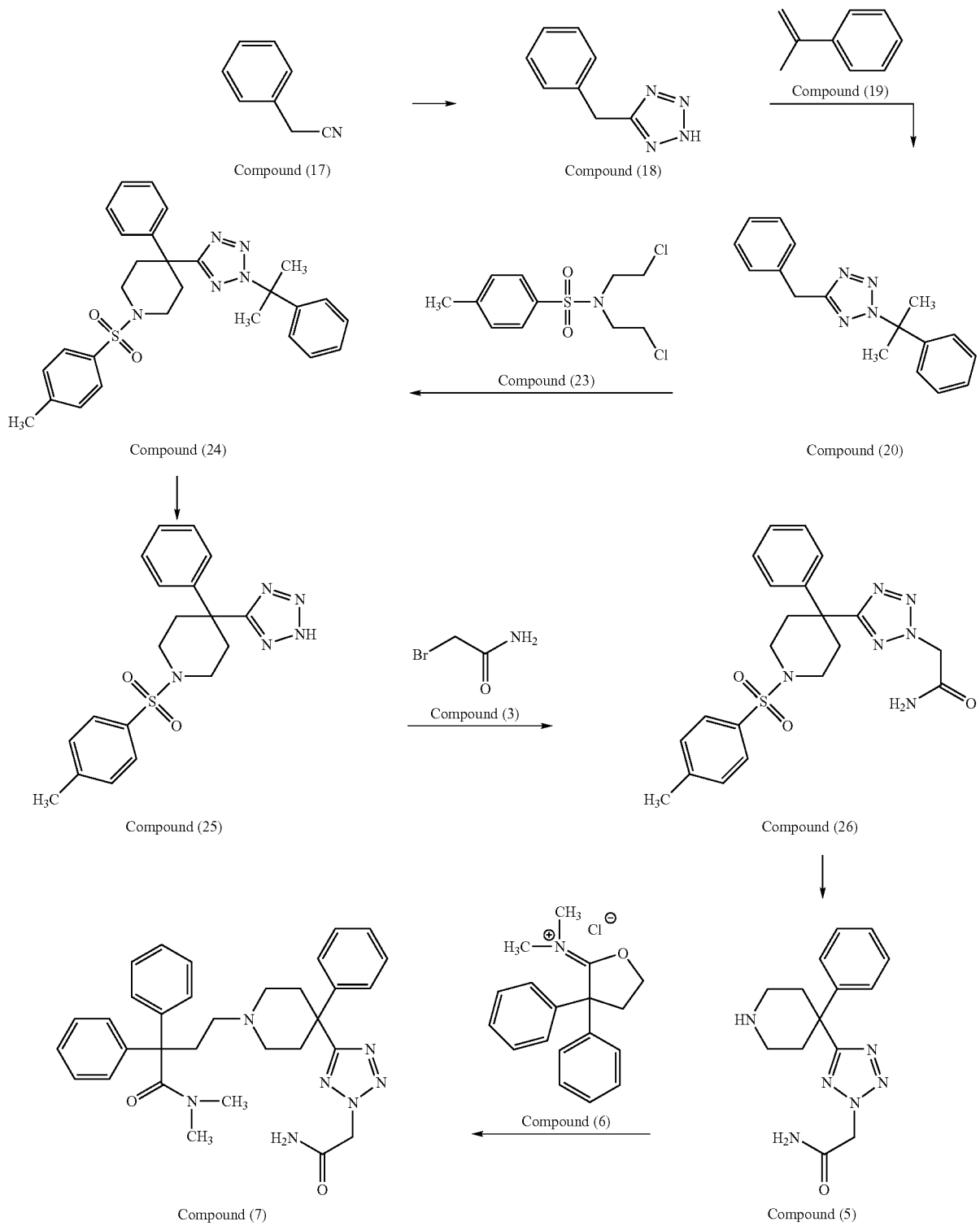

Scheme 31

4.2.25. Synthesis of Bis-dichloroethylamine Derivatives

In certain embodiments, the present invention includes the use of bis-dichloroethylamine derivatives in the synthesis of compounds of Formula I, including, but not limited to Compound (7). For example, Compound (21) is prepared from Compound (29), which is commercially available, generally according to the method of Chambers et al. (J. Med. Chem. (1992) 35: 2033-39), as indicated in Scheme 32:

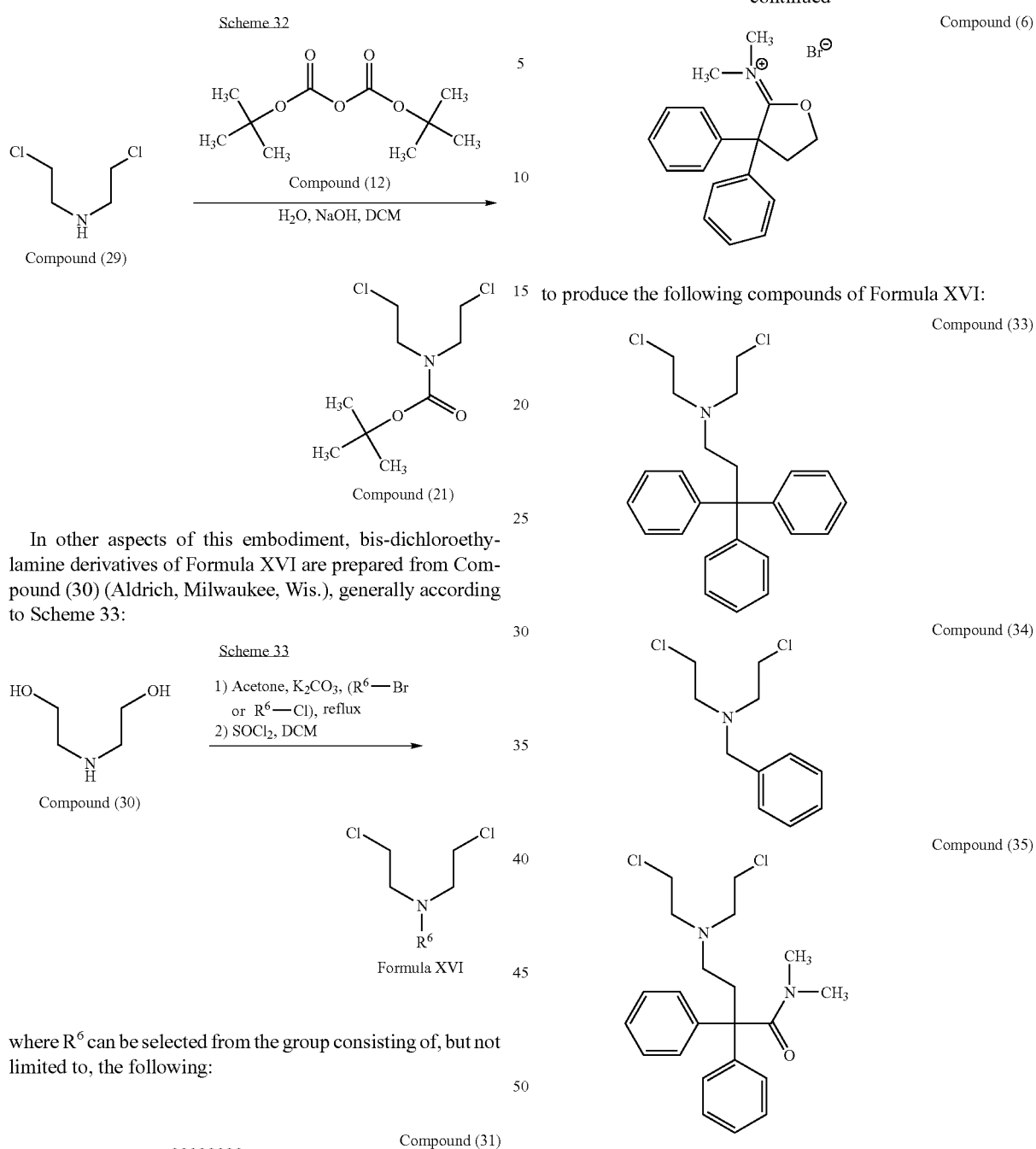

In other aspects of this embodiment, bis-dichloroethylamine derivatives of Formula XVI are prepared from Compound (30) (Aldrich, Milwaukee, Wis.), generally according to Scheme 33:

where R[6] can be selected from the group consisting of, but not limited to, the following:

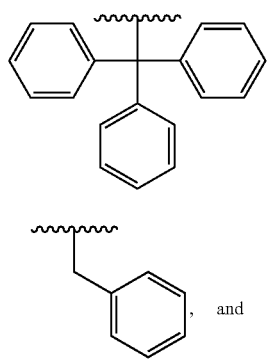

to produce the following compounds of Formula XVI:

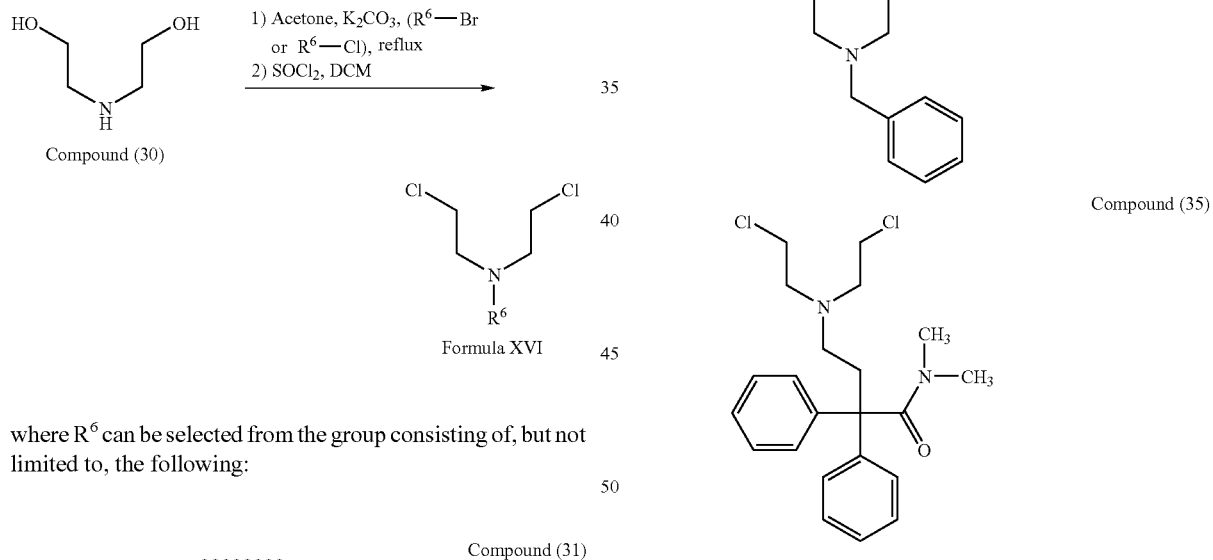

According to Scheme 33, in general, potassium carbonate and the corresponding R[6]-chloride or bromide are added to a stirred solution of Compound (30). This solution is warmed to reflux temperature for 8 hr, allowed to cool to room temperature, and then filtered. The filtrate is concentrated to dryness, and after aqueous workup, the crude material is taken up in methanol and HCl (in diethyl ether) is added. The mixture is concentrated to dryness, the crude material is taken up in dichloromethane and thionyl chloride added dropwise. The resulting mixture is stirred at room temperature for an hour and then the volatile materials are removed under vacuum to provide the product compound of Formula XVI.

4.2.26. Additional Method for Making Compound (7) According to Schemes 17-33

In another embodiment, the present invention is directed toward an additional approach to the synthesis of a 4-Tetrazolyl-4-phenylpiperidine Compound, in which methods and reagents of Schemes 17-30 above, can be combined to provide a method for the synthesis of a compound according to Formula I. For example, as depicted in Scheme 34 below, Compound (7), which is a compound according to Formula I, is synthesized according to methods and conditions described in Sections 4.2.17 to 4.2.25, above.

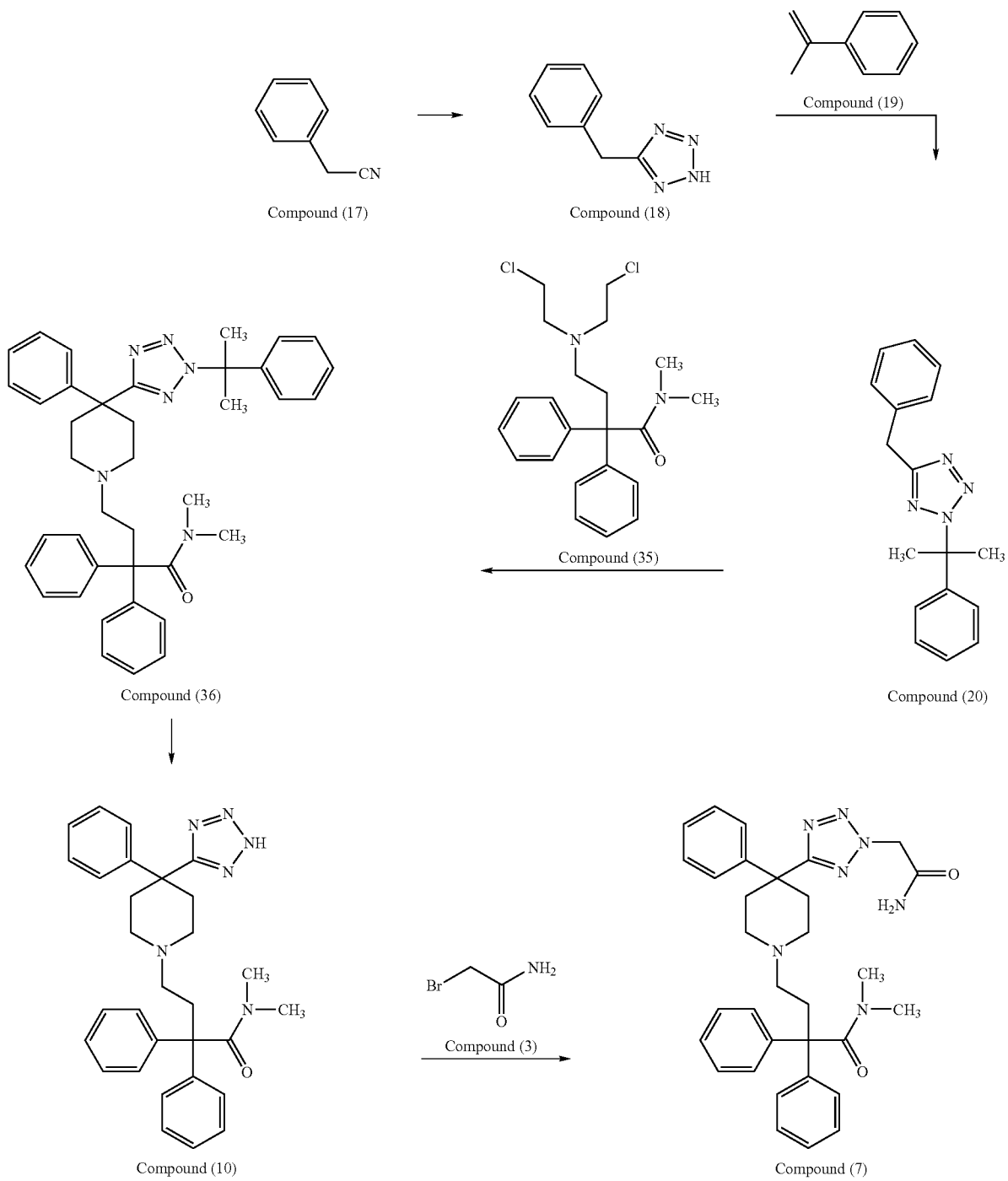

Scheme 34

4.2.27 Additional Method for Making Compound (7)

In another embodiment, Compound (7) is synthesized from Compound (5) according to the following scheme:

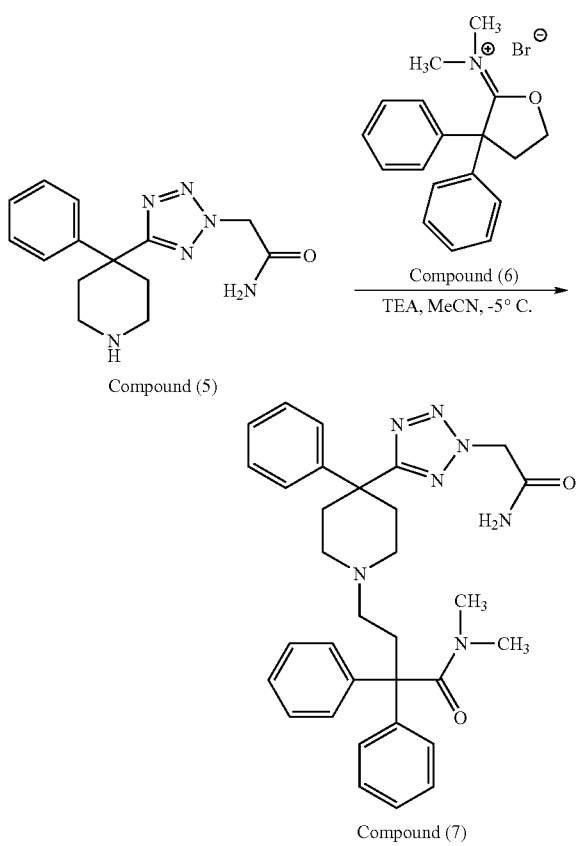

According to this embodiment, a mixture of dimethyl-(tetrahydro-diphenyl-furylidene)ammonium-bromide (DMAB) (Compound (6), and acetonitrile (MeCN) is cooled to −5° C. Portions of Compound (7) are charged to this mixture, followed by triethylamine (TEA) while maintaining an internal temperature of −5° C. The reaction mixture is stirred at −5+ C. until the reaction is complete, i.e. until less than about 3% of Compound (5) remains as indicated by HPLC analysis. The reaction mixture is then warmed to about 5° C. and filtered. The wet cake is first slurry washed and then displacement washed with water, before drying at 60° C. under high vacuum.

5. EXAMPLES

Unless otherwise noted, the reagents and solvents used in the Examples disclosed are obtained from either Aldrich Chemical Co., Milwaukee, Wis. (e.g. 1,4-dioxane, sodium azide, zinc bromide, DBU, DMSO, potassium carbonate) or from Fisher Scientific Company (Pittsburgh, Pa.) (e.g. MTBE, isopropyl acetate, ethyl acetate, methanol, and sodium sulfate).

LC/MS analyses, referred to below, were generally carried out as follows. Liquid chromatographic analyses (HPLC) were performed using a C18 column (Zorbax XDB-C18, 4.6×50 mm, 5 micron particle size; (Agilent, Palo Alto, Calif.)). The column was run at a temperature of 25° C. and monitored at 260 nm (reference 360 nm). The flow rate of the mobile phase was 1 mL/min. The mobile phase was run as a gradient consisting of a mixture of solvents A (0.1% TFA/$H_2O$) and B (0.1% TFA/$CH_3CN$), having the following composition: 85% A/15% B (0 min), 5%A/95%B (2.3 min), 5% A/95%B (4.3 min), 85% A/15% B (4.4 min), and 85%A/15% B (5.2 min).

Mass selective detection (MSD) was carried out with atmospheric pressure electrospray ionization (API-ES) as the ionization mode, with positive polarity. Typical settings for each of the MSD instruments employed (Agilent 1100 LC/MS (Agilent, Palo Alto, Calif.) and Waters ZQ MS (Waters, Milford, Mass.)) in the analyses described below were as follows: Agilent 110 LC/MS: (a) Fragmentor ramp (disabled), (b) Fragmentor (80), (c) Gain (1 EMV), (d) Threshold (20), (e) Stepsize (0.15), (f) Gas Temp (° C.) (350), (g) Drying gas (12.0 L/min), (h) Nebulizer pressure (40 psig), (i) Vcap (3500 V), () peak width (0.07 min), and (k) MW range (150-2000); and Waters ZQ MS: (a) Cone (V) (30.00), (b) Extractor (V) (2.00), (c) RF Lens (V) (0.3), (d) Source Temp (° C.) (150), (e) Cone Temp. (° C.) (20), (f) Desolvation gas (° C.) (350), (g) Cone Gas Flow (111 L/hr), (h) Desolvation gas flow (615 L/hr), (i) Capillary (kV), (j) LM 1 Resolution (15), (k) HM 1 Resolution (15), (l) Ion Energy 1 (0.5), and (m) Multiplier (650).

5.1. Example 1

Synthesis of Compound (2)

(1-benzyl-4-phenyl-4-(2H-tetrazol-5-yl)-piperidine)

To a well-stirred solution of 125.77 g 1-benzyl-4-cyano-4-phenylpiperidine hydrochloride (the hydrochloride salt of Compound (1)), (Aldrich Chemical Co., Milwaukee, Wis.) in 1.0 liter of chloroform was added 500 mL of a saturated aqueous solution of $Na_2CO_3$. The layers were separated and chloroform layer recovered. The aqueous layer was extracted with approximately 200 mL chloroform. The two recovered chloroform layers were combined, extracted with approximately 500 mL of deionized water, dried over anhydrous sodium sulfate, and evaporated to constant weight, yielding 109.7 g of Compound (1), (1-benzyl-4-cyano-4-phenylpiperidine), as the free amine.

The free amine of Compound (1) (109.7 g) was dissolved in 500 mL of 1-methyl-2-pyrrolidone and divided into two portions and the following steps were carried out for both portions in parallel with duplicate flasks.

A portion of the solution of Compound (1) in 1-methyl-2-pyrrolidone (250 mL containing 54.85 g Compound (1)) was introduced into a 3.0 liter flask fitted with an overhead mechanical stirrer, thermometer, addition funnel and nitrogen inlet. Solvent (500 mL of 1-methyl-2-pyrrolidone) and $ZnBr_2$ ((134.1 g, 0.595 mol, dissolved in 100 mL water), were added to the flask. The addition of $ZnBr_2$ created an exotherm which raised the temperature of the reaction mixture to approximately 55° C. to 60° C. Solid sodium azide (51.6 g, 0.794 mol) was added all at once, and the reaction mixture heated to 135° C. under an $N_2$ blanket. The reaction was monitored by LC/MS until the starting material (Compound (1)) was no longer detectable (7 days).

The reaction mixture was added, slowly, to an aqueous HCl solution (1% HCl), with stirring, in an 8-liter beaker. The head space over the liquid in the beaker was swept with argon to remove any possible hydrazoic acid formed. The solution was stirred for approximately three hours and the solids that developed were isolated by vacuum filtration. The collected solids were first air dried and then dried under vacuum. A total of 62.49 g of Compound (2) was recovered. The second reaction, which had been run in parallel, yielded 63.62 g of Compound (2) ($^1$H NMR (MeOHd$^4$): δ 7.5 (m, 5H), 7.2 (m, 5H), 3.5 (m, 2H), 3.35 (s, 2H), 3.05 (m, 4H), 2.45 (m, 2H)).

5.2. Example 2

Synthesis of Compound 4

(2-[5-(1-benzyl-4-phenylpiperidin-4-yl)-tetrazol-2-yl]-acetamide)

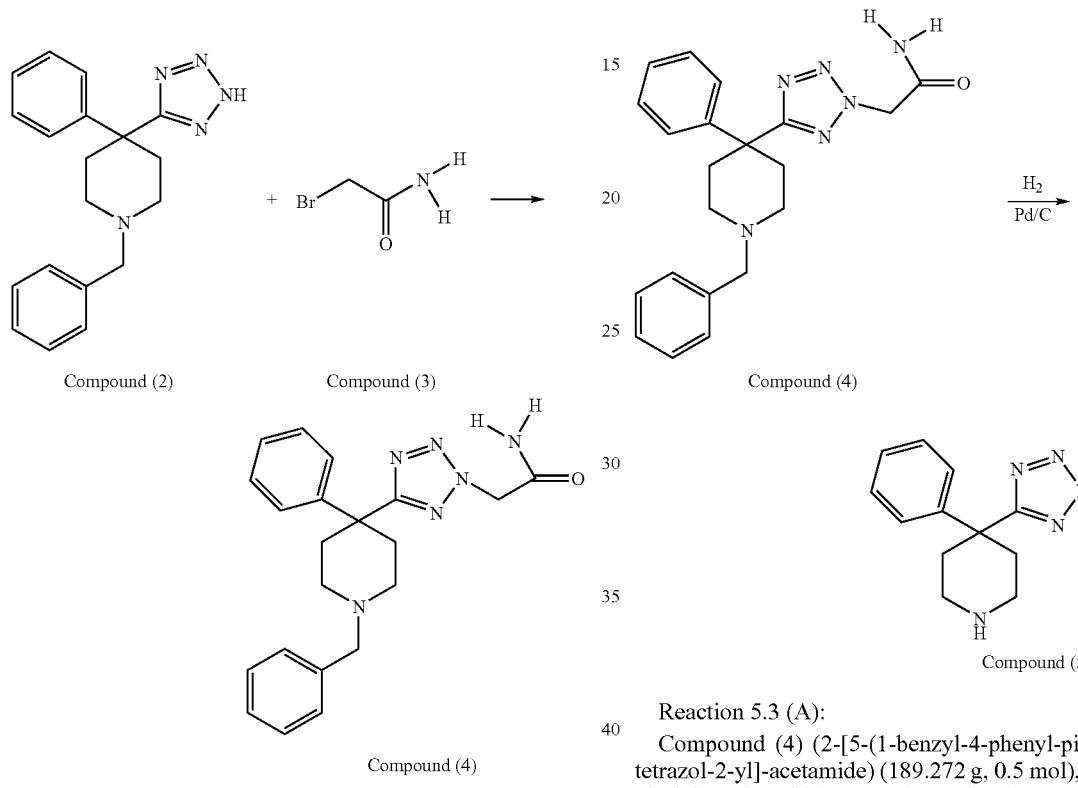

Compound (2)  Compound (3)

Compound (4)

To a 3 liter round-bottom flask fitted with a magnetic stirrer, temperature controller, condenser, and N$_2$ inlet, were added Compound (2) (1-benzyl-4-phenyl-4-(2H-tetrazol-5-yl)-piperidine) (234.57 g, 0.734 mol), dimethyl formamide (2.0 L), potassium carbonate (121.8 g, 0.881 mol), and 2-bromoacetamide (101.32 g, 0.734 mol) (Aldrich Chemical Co., Milwaukee, Wis.). This reaction mixture was heated to 50° C. and incubated overnight under N$_2$. Analysis of an aliquot of the reaction by LC/MS indicated that the reaction was complete.

The reaction mixture was cooled to room temperature and poured into 4.5 L rapidly-stirring deionized water. Ethyl acetate (2.5 L) was added and the precipitate that formed was collected by vacuum filtration and then dissolved in approximately 6 L of ethyl acetate. The layers generated were separated and the ethyl acetate layer recovered, dried over anhydrous sodium sulfate, and evaporated by rotary evaporation to provide a thick slurry. The slurry was triturated with approximately 2 L of ethyl ether and the suspended solids were collected by vacuum filtration and dried, providing 118.26 g of Compound (4) as a pale yellow solid. The ether filtrates were also collected and concentrated, under vacuum, to a mobile oil, which was shown by LC/MS analysis to contain Compound (4) ($^1$H NMR (MeOHd$^4$): δ 7.2-7.0 (m, 10H), 5.3 (s, 2H), 3.3 (s, 2H), 2.7 (m, 4H), 2.25 (m, 2H), 2.1 (m, 2H)).

5.3. Example 3

Synthesis of Compound 5

(2-[5-(4-phenylpiperidin-4-yl)-tetrazol-2-yl]-acetamide)

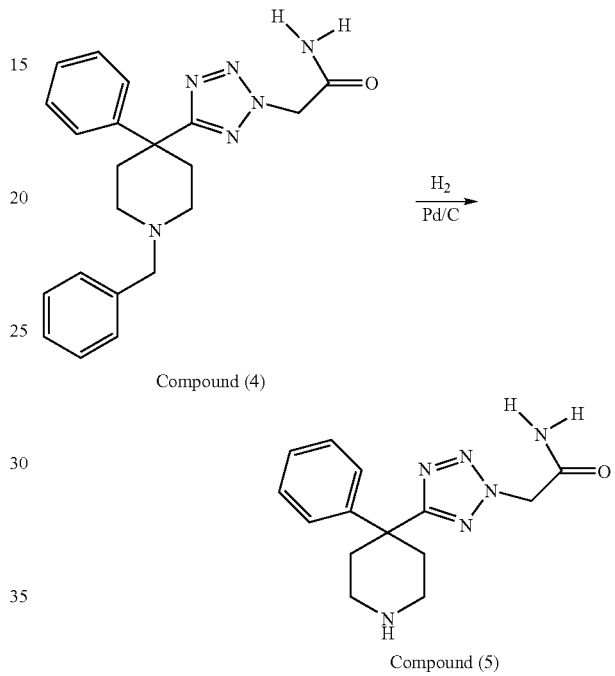

Compound (4)

Compound (5)

Reaction 5.3 (A):

Compound (4) (2-[5-(1-benzyl-4-phenyl-piperidin-4-yl)-tetrazol-2-yl]-acetamide) (189.272 g, 0.5 mol), ethanol (3L), glacial acetic acid (11.7 mL), catalyst (52.6 g of 10% Pd/C (palladium powder on activated carbon) comprising approximately 50% water (catalogue number E 101 NE/W 10% Pd; Degussa Corporation, Parsippany, N.J.)) were added, under an argon blanket, to a 3-neck, 5-liter round-bottomed flask fitted with a magnetic stir bar. Hydrogen was introduced at approximately atmospheric pressure, and the flask purged with hydrogen to remove argon. The reaction was stirred overnight under hydrogen. LC/MS analysis indicated that the reaction had gone to completion. The reaction flask was purged with Argon and filtered through a celite bed under an Argon blanket. The filter cake was washed with methanol and the combined filtrates concentrated under reduced pressure to provide a thick oil that was further concentrated, under high vacuum, to provide 148.51 g of product as a foam.

Reaction 5.3 (B):

Compound (4)-containing mobile oil, provided by evaporation of the ether filtrates of Example 5.2, (118.26 g, 0.31 mol), ethanol (1.65 L), glacial acetic acid (7.3 mL), and palladium catalyst (32.9 g of 10% Pd/C (palladium powder on activated carbon) comprising approximately 50% water (catalogue number E 101 NE/W 10% Pd; Degussa Corporation, Parsippany, N.J.)) were placed in a 3.0 L, single-neck round bottom flask fitted with a magnetic stir bar. Reaction 5.3 B was run, and the product isolated, as described above for Reaction 5.3 A. After the final concentration step, Reaction 5.3 B provided 71.95 g of product as a clear liquid.

NMR analysis of Compound (5) provided: $^1$H NMR (MeOHd$^4$): δ 7.2-7.0 (m, 10H), 5.5 (s, 2H), 3.2 (m, 2H), 2.85 (m, 4H), 2.3 (m, 2H).

5.4. Example 4

Synthesis of Compound (6)

(3,3-Diphenyl-dihydro-furan-2-ylidene)-dimethyl-ammonium bromide

To a mechanically-stirred suspension of 4-bromo-2,2diphenylbutyric acid (100 g, 0.313 mol) in chloroform, was added triethylamine (65.2 mL, 0.469 mol), DMF (1 mL), and 2M dimethylamine in THF (160 mL, 0.320 mol). The reaction was cooled to −10° C. (dry ice, acetone bath) and oxalyl chloride (60.6 g, 0.477 mol) in toluene (400 mL) was added slowly (dropwise) such that the temperature of the reaction remained between −5° C. and −10° C. After addition of the oxalyl chloride was complete, the reaction mixture was stirred an additional 1.5 hr at 0° C. (ice/water bath). The reaction was filtered cold, and the resulting filter cake recovered was dried overnight, yielding 124.3 grams of white solid, which includes both Compound (6) and triethylammonium chloride, and which was used without further purification in the next step, which is described in Example 5, below.

5.5. Example 5

Synthesis of Compound (7)

(4-[4-(2-carbamoylmethyl-2H-tetrazol-5-yl)-4-phenyl-Piperidin-1-yl]-N,N-dimethyl-2-2-diphenyl-butyramide)

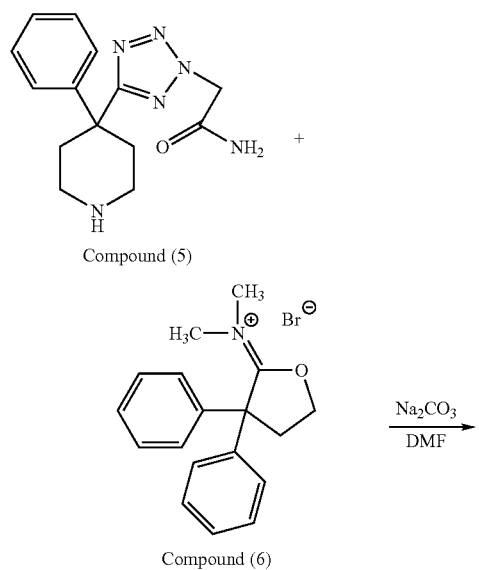

Compound (5)

Compound (6)

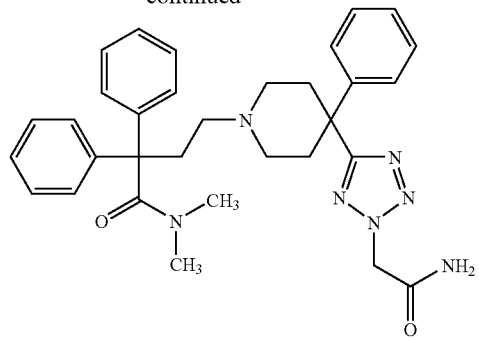

Compound (7)

Reaction 5.5 (A):

Solid Compound (5) (2-[5-(4-phenyl-piperidin-4-yl)-tetrazol-2-yl]-acetamide) (71.95 g, 0.25 mol) (147.16 g, 0.513 mol), prepared in Reaction 5.3 (A) above, Na$_2$CO$_3$ (127.8 g), Compound (6) ((3,3-Diphenyl-dihydro-furan-2-ylidene)-dimethyl-ammonium bromide) (187.48 g, 0.541 mol) (prepared as described in Section 5.4, above), and DMF (approximately 2.5 L) were added to a 5.0 L, single-neck round-bottom flask. This reaction mixture was heated to 100° C. and incubated, under N$_2$, overnight. The reaction was quenched by pouring the reaction mixture into deionized water (approximately 6 L) and the resulting solution was extracted twice with ethyl acetate (2 L for each extraction). The ethyl acetate layers were combined, dried over anhydrous sodium sulfate, and concentrated under vacuum to provide a free-flowing oil.

Reaction 5.5 (B):

Compound (5), i.e. the clear liquid product prepared in Reaction 5.3 (B) above, Na$_2$CO$_3$ (62.5 g), Compound (6) ((3,3-Diphenyl-dihydro-furan-2-ylidene)-dimethyl-ammonium bromide) (91.69 g, 0.26 mol), and DMF (approximately 1 L) were added to a 2.0 L single-neck round-bottom flask. This reaction mixture was heated to 100° C. and incubated under N$_2$ overnight. The reaction was quenched by pouring the reaction mixture into deionized water (approximately 4 L) to provide a mixture that was extracted twice with ethyl acetate (1.5 L for each extraction). The ethyl acetate layers were combined, dried over anhydrous sodium sulfate, and concentrated under vacuum to provide a free-flowing oil.

The free-flowing oils provided by reactions 5.5 (A) and 5.5 (B) were combined and purified by silica-gel chromatography, yielding, after concentration, 256.4 g of Compound (7) as a pale yellow solid. The silica-gel chromatography was carried out using a Biotage column (Biotage, Charlottesville, Va.), which was washed with ethyl acetate and then with a solvent consisting of 80% ethyl acetate, 10% ethanol, and 10% triethylamine. Product-containing fractions were identified by thin-layer chromatography. The product (256.4 g) was triturated in hot (boiling) acetonitrile (approximately 2.4 L), and the resulting suspension was cooled overnight to room temperature, and then chilled in an ice bath. Solids were collected by vacuum filtration, washed with cold (5° C.) acetonitrile, air dried, and then dried overnight under vacuum to provide 193 g of Compound (7), as the free amine, in the form of a white solid.

NMR analysis of Compound (7) provided: ($^1$H NMR (CDCl$_3$)): δ 7.65 (m, 8H), 7.55 (m, 6H), 7.42 (m, 1H), 5.85 (bs, 1H), 5.60 (bs, 1H), 5.30 (s, 2H), 2.98 (bs, 3H), 2.87 (bm, 4H), 2.20-2.45 (bm, 7H), 1.90-2.20 (bm, 4H).

A portion of Compound (7), as the free amine, was then converted to the corresponding sulfamic acid salt. Compound (7) (100 g) was dissolved in 0.5 L acetonitrile in a 2.0 L round-bottom flask. One equivalent (17.6 g) of sulfamic acid (Aldrich Chemical Co., Milwaukee, Wis.) was dissolved in 50 mL of hot (about 75° C.) water and added, with stirring, to the solution of Compound (7) in acetonitrile. The resulting solution comprising Compound (7) and sulfamic acid was stirred for approximately one hour at a temperature of 50° C., filtered through filter paper to remove a fine precipitate, and then evaporated and dried under vacuum overnight. The dried material was suspended in hot (boiling) acetonitrile, cooled to room temperature and then chilled in an ice water bath. Solids were collected by vacuum filtration, air dried, and then dried under high vacuum, providing 117.2 g of the sulfamic acid salt of Compound (7) as a white solid.

NMR analysis of the sulfamic acid salt of Compound (7) provided: ($^1$H NMR (DMSO d$^6$)): δ 7.80 (s, 1H), 7.45 (m, 5H), 7.32 (m, 8H), 7.20 (m, 3H), 5.38 (s, 2H), 2.88 (bs, 3H), 2.72 (bm, 2H), 2.30-2.60 (bm, 10H), 2.20 (bs, 3H), 2.06 (s, 3H).

5.6. Example 6

Synthesis of Compound (9) (4-Phenyl-4-(2H-tetrazol-5-yl)-piperidine

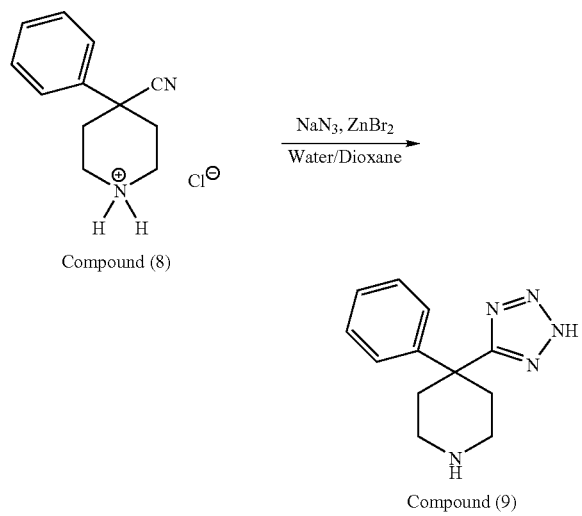

A 100 mL round-bottom flask, fitted with a magnetic stir bar, reflux condenser/nitrogen inlet and temperature probe, was charged with Compound (8) (4-cyano-4-phenyl-piperidinium chloride) (Acros Organics, Morris Plains, N.J.) (2.035 g, 0.009 mol), water (16 mL), 1,4-dioxane (9 mL), and sodium azide (1.16 g, 0.018 mol). Zinc bromide (2.0 g, 0.009 mol) was added and the pH of the solution adjusted to about 7 with 50% NaOH. The resulting mixture was heated, with reflux at a temperature within the range of from about 90° C. to about 100° C. for 24 hours. The white solid that formed in the reaction mixture ("the tetrazole product" i.e. Compound (9)) was collected and used directly in the following step, which is disclosed in Section 5.7, below. Compound (9) was characterized by HPLC carried out using a Phenomenex 150 mm×4.6 mm, 5 micron particle size, C18 column. Chromatography was carried out at 40° C. with a flow rate of 1 mL/min. The eluate was monitored by UV absorption at 220 nm. Elution was carried using a linear gradient run over 10 minutes, in which the initial composition of the mobile phase was 90% A/10% B and the final composition of the mobile phase was 10% A/90% B, where A is pH 7.0 phosphate-buffered water and B is methanol. This mobile phase composition was maintained for five minutes and then returned to 90% A/10% B. Under these conditions the product, Compound (9) had a retention time of 4.71 minutes and a purity of 98% by HPLC area.

5.7. Example 7

Synthesis of Compound (6)

((3,3-Diphenyl-dihydro-furan-2-ylidene)-dimethyl-ammonium bromide)

This example provides and alternative method (compared to Example 4, above) for the synthesis of Compound (6). In the method disclosed in this Example, all glassware is dried before use. According to this alternative approach, a solution of 4-bromo-2,2-diphenylbutyric acid chloride (5 g, 14.8 mol) in toluene (20 mL) is delivered to a three-neck round bottom flask equipped with a dry ice "cold finger," dimethylamine gas inlet, and a magnetic stir bar. The solution was cooled to 0° C.-5° C., and triethylamine (3 mL, 21.6 mmol) was added while maintaining the temperature of the solution within the range of 0° C.-5° C. Dimethylamine gas was charged over the head space in the flask while the internal temperature was maintained within the range of 0° C.-5° C. Progress of the reaction was monitored by analyzing aliquots (by HPLC) of the reaction (taken at 5 minute intervals) for the presence of 4-bromo-2,2-diphenylbutyric acid chloride. Addition of dimethylamine gas to the flask was stopped as soon as the 4-bromo-2,2-diphenylbutyric acid chloride had been completely consumed. The resulting suspension was stirred at 5° C. for an additional 30 minutes and then the suspended solids were recovered by filtration within a nitrogen-purged glove bag. The resulting wet cake was washed with toluene and dried under vacuum to provide 4.75 g of a white powder comprising a mixture of the desired product (Compound (6)), and triethylamine hydrochloride which could be used directly in the reaction of Example 8, below.

5.8. Example 8

Synthesis of Compound (10)

(N,N-Dimethyl-2,2-diphenyl-4-[4-phenyl-4-(2H-tetrazol-5-yl)-piperidin-1-yl]-butyramide

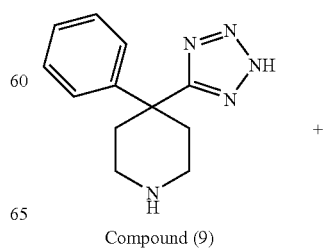

Compound (9)

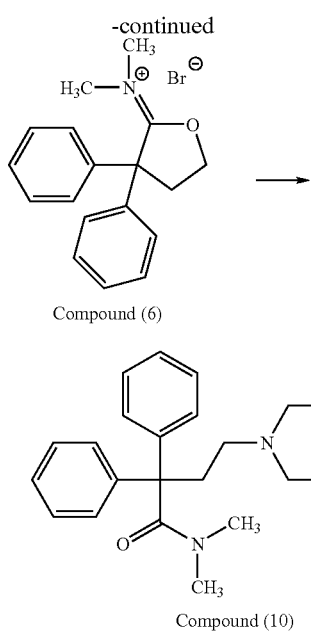

Compound (6)

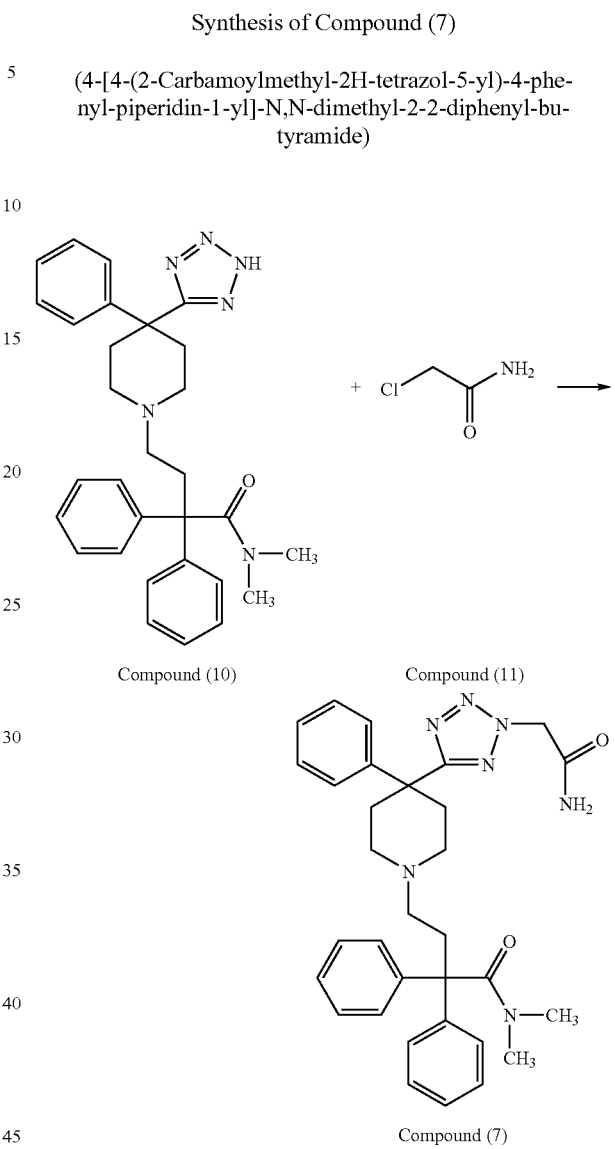

Compound (10)

Compound (9) (4-Phenyl-4-(2H-tetrazol-5-yl)-piperidine), i.e. the tetrazole product formed in the reaction disclosed in Section 5.6, above, (1.062 g) was charged, with 15 mL DMSO, to a 25 mL three-neck roundbottom flask fitted with a magnetic stir bar, temperature probe, and nitrogen inlet. The resulting slurry was stirred at room temperature for about 5 minutes. DBU (2,3,4,6,7,8,9,10-Octahydro-pyrimido [1,2-α]azepine), (2.9 mL, 2.952 g, 0.0194 mol) was added dropwise over about three minutes. The slurry was stirred until a solution was obtained (about 10 minutes). Compound (6) (3,3-Diphenyl-dihydro-furan-2-ylidene)-dimethyl-ammonium bromide) (60% pure, 2.52 g, 0.004 mol) was added in two portions over about three minutes. The reaction was stirred at 22° C. for 140 minutes and then quenched with 10 mL of water. The quenched reaction mixture was transferred to a separatory funnel with an additional 30 mL of water and extracted with 20 mL MTBE (methyl t-butyl ether) and then extracted with 20 mL isopropyl acetate. The pH of the aqueous phase was adjusted to about pH 5 with concentrated HCl and the product (Compound (10) (N,N-Dimethyl-2,2-diphenyl-4-[-4-phenyl-4-(2H-tetrazol-5-yl)-piperidin-1-yl]-butyramide) extracted into ethyl acetate (3×50 mL). The recovered organic phases were pooled, and concentrated to an oil ("crude Compound (10)") that was used directly for the formation of Compound (7), as described in Section 5.9, below. Compound (10) was characterized by HPLC carried out using a Phenomenex 150 mm×4.6 mm, 5 micron particle size, C18 column. Chromatography was carried out at 40° C., with a flow rate of 1 mL/min. The eluate was monitored by UV absorption at 220 nm. Elution was carried out using a ten-minute, linear gradient in which the initial composition of the mobile phase was 50% A/50% B and the final composition of the mobile phase was 20% A/80% B, where A is pH 7.0 phosphate-buffered water and B is methanol. This mobile phase composition was maintained for 6 minutes, and then changed to 50% A/50% B. Under these conditions the product, Compound (9) had a retention time of 6.99 minutes and a purity of 89% by HPLC area.

5.9. Example 9

Synthesis of Compound (7)

(4-[4-(2-Carbamoylmethyl-2H-tetrazol-5-yl)-4-phenyl-piperidin-1-yl]-N,N-dimethyl-2-2-diphenyl-butyramide)

Crude Compound (10) (1.323 g) (formed as disclosed in Section 5.8, above) was dissolved in 15 mL DMSO and charged to a 50 mL round-bottom flask fitted with a magnetic stir bar, reflux condenser/nitrogen inlet, and temperature probe. Compound (11) (2-chloroacetamide) (0.300 g, 0.0032 mol) (Aldrich Chemical Co., Milwaukee, Wis.) and potassium carbonate (1.1 g, 0.008 mol) were added and the resulting mixture heated at 60° C. for 4 hours. Isopropyl acetate (30 mL) was added and the mixture transferred to a separatory funnel with 30 mL water. The aqueous phase, which had a pH of about 11, was extracted twice with isopropyl acetate (30 mL for each extraction). The organic extracts were recovered, combined, washed with 15 mL of a saturated solution of sodium chloride in water, dried over sodium sulfate, and concentrated to an oil. The oil was dissolved in 5.5 mL of methanol and stirred for 30 minutes during which time the product (Compound (7) (4-[4-(2-Carbamoylmethyl-2H-tetrazol-5-yl)-4-phenyl-piperidin-1-yl]-N,N-dimethyl-2-2-diphenyl-butyramide) crystallized. The crystals of Compound (7) (0.309 g) were collected by filtration.

NMR analysis of Compound (7) provided (a) $^1$H NMR (CDCl$_3$, 600 MHz): δ 1.96-2.01 (m, 4H), 2.29 (m, 4H), 2.37-2.40 (m, 3H), 2.74-2.76 (m,4H), 2.84-3.02 (m, 3H), 5.27 (s, 2H), 5.66 (s, 1H), 5.86 (s, 1H), 7.15 (m, 1H), 7.24-2.27 (m, 6H) 7.34-7.38 (m, 8H), and (b) $^{13}$C NMR (CDCl$_3$, 150.9 MHz): 35.43, 41.58, 42.37, 50.76, 55.20, 56.02, 59.86, 126.17, 126.84, 126.92, 128.29, 128.59, 128.75, 140.96, 165.76, 173.73.

Compound (7) was characterized by HPLC carried out using a Phenomenex 150 mm×4.6 mm, 5 micron particle size, C18 column. Chromatography was carried out at 40° C., with a flow rate of 1 mL/min. The eluate was monitored by UV absorption at 220 nm. Elution was carried out using a ten-minute, linear gradient in which the initial composition of the mobile phase was 50% A/50% B and the final composition of the mobile phase was 20% A/80% B, where A is pH 7.0 phosphate-buffered water and B is methanol. This mobile phase composition was maintained for 6 minutes, and then changed to 50% A/50% B. Under these conditions the product, Compound (7) had a retention time of 10.312 minutes and a purity of 98% by HPLC area.

5.10. Example 10

Synthesis of Compound (14)

(tert-butyl 4-phenyl-4-(2H-tetrazol-5-yl)piperidine-1-carboxylate)

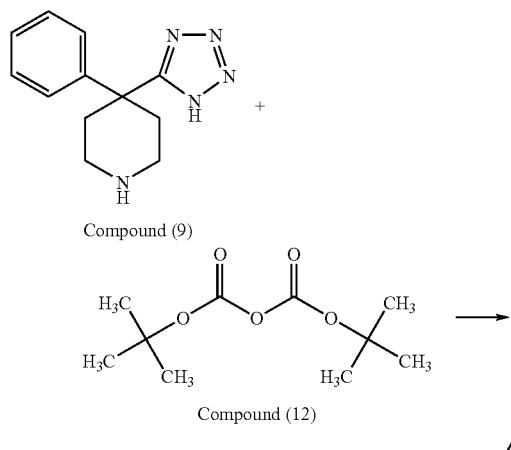

In a first instance, Compound (14) was synthesized as follows: Compound (9) (4-Phenyl-4-(2H-tetrazol-5-yl)-piperidine) hydrochloride, (i.e. the salt of the tetrazole product which can be formed in the reaction disclosed in Section 5.6, above), (50 g; 145 mmole) was suspended in aqueous sodium hydroxide solution (12.85 g; 321.2 mmole in 200 mL water) with stirring. Di-tertbutyldicarbonate (Compound (12)) was added and the mixture stirred rapidly. The temperature of the reaction first rose to 40° C. over 5 minutes, and then subsided. The mixture was cooled in a water bath and then stirred overnight at room temperature. The mixture was partitioned between ethyl acetate (1 L) and aqueous acetic acid (100 mL in 1 L water), and the organic phase was separated. The aqueous phase was further extracted with ethyl acetate (1 L) and the combined organics evaporated to dryness under vacuum to provide the desired product, Compound (14) as a foam, which crystallized on standing. The product was then triturated with hexane:ether (1:1) (200 mL).

In a second instance Compound (14) was synthesized in a larger scale reaction as follows: Compound (9) (4-Phenyl-4-tetrazol-1-yl-piperidine hydrochloride zinc chloride complex) (100 g, 292.06 mMol) was suspended in aqueous sodium hydroxide solution (15.42 g, 642.25 mMol) in water (400 mL) with stirring for 10 min. Compound (12) (di-tert-butyl dicarbonate) (70.07 g, 321.25 mMol) in acetone (200 mL) was added and the mixture stirred vigorously for 4 h. The mixture was diluted with ethyl acetate (250 mL) and stirring was continued for 15 min to solubilize some sticky solids from the sides of the beaker. The mixture was partitioned between ethyl acetate (1,000 ml) and 0.5M sulfamic acid solution (1,000 ml) and the organic phase separated. The organic phase was washed with 0.5M sulfamic acid (1,000 ml) and water (1,000 ml). The aqueous washings were back extracted with ethyl acetate (1,000 ml) and the combined organics dried (MgSO$_4$) and the solvent evaporated to dryness in vacuo to give a white solid. This was triturated with hexanes (500 mL) to give Compound (14) (80.5 g, 88%) as a white solid, m.p.=184.5-186° C.; TLC SiO$_2$, EtOAc Rf=0.56; δ$_H${400 MHz, CDCl$_3$}7.29-7.18 (5H, m), 3.90 (2H, m), 3.25-2.70 (4H, m), 2.40-2.15 (2H, m), 1.40 (9H, s); LC: 100% purity by DAD; MS: [M+Na]$^+$=352.2/353.1.

5.11. Example 11

Synthesis of Compound (22)

(tert-butyl 4-phenyl-4-(2-(2-phenylpropan-2-yl)-2H-tetrazol-5-yl)piperidine-1-carboxylate)

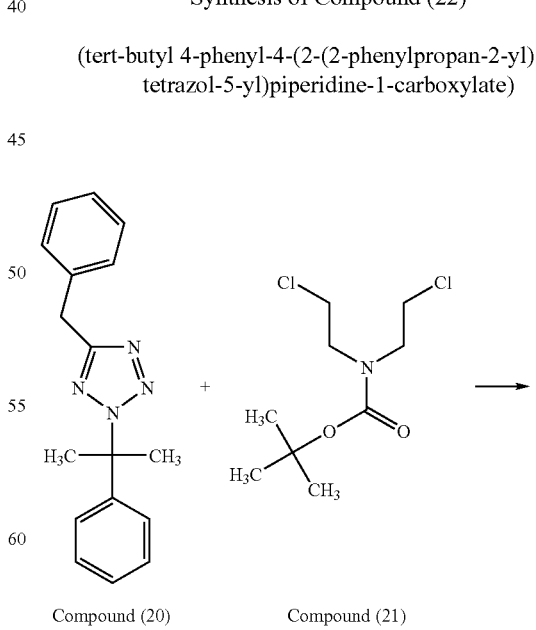

Compound (20)    Compound (21)

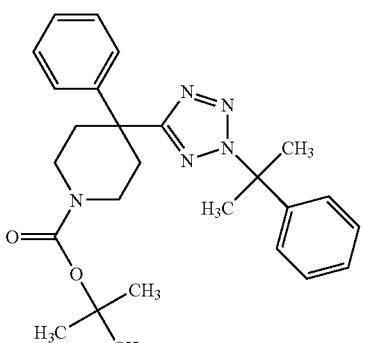

Compound (22)

Compound (20) (5-benzyl-2-(2-phenylpropan-2-yl)-2H-tetrazole), (1 g; 3.59 mmole) was taken up in diethyl ether (80 mL) and n-butyl lithium (4.5 mL; 7,18 mmole) added at a temperature of about −15° C. to −20° C. (ice/water/NHCl bath). Compound (21) (tert-butyl bis(2-chloroethyl)carbamate) (0.95 g; 3.95 mmole) in diethyl ether (10 mL) was added dropwise over 5 minutes, after which the mixture was stirred at −15° C. for 30 minutes. During this time a color change, from dark red to pale yellow, was noted. The mixture was allowed to warm to −10° C. and then to room temperature. The reaction was quenched with 50 mL aqueous $NH_4Cl$. The resulting layers were separated and the organic phase was dried over $MgSO_4$ and then concentrated to dryness. The dried product was suspended, chromatographed, and product-containing fractions were combined and concentrated, yielding 1 g of Compound (22).

5.12. Example 12

Preparation of Compound (15) (4-(2-Carbamoylmethyl-2H-tetrazol-5-yl)-4-phenyl-piperidine-1-carboxylic acid tert-butyl ester)

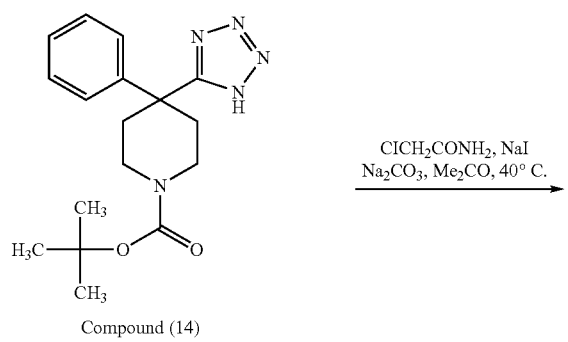

Compound (14)

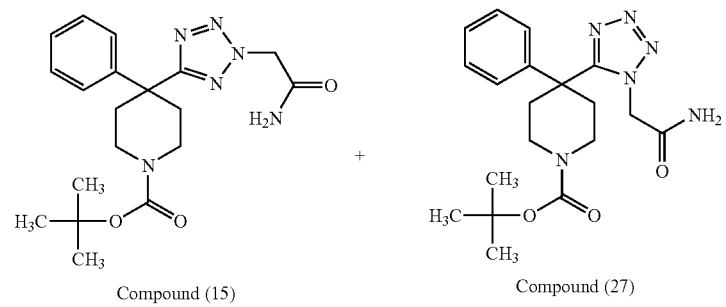

Compound (15)   Compound (27)

Recrystallization from
4:1 toluene:ethyl acetate

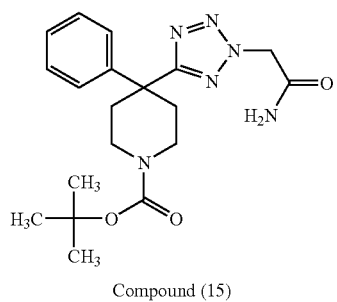

Compound (15)

Compound (14) (4-Phenyl-4-(1H-tetrazol-5-yl)-piperidine-1-carboxylic acid tert-butyl ester) (20 g, 60.7 mMol), sodium iodide (10.85 g, 72.9 mMol), sodium carbonate (7.73 g, 72.9 mMol) and Compound (11) (2-chloroacetamide) (5.85 g, 62.52 mMol) were heated together in acetone (100 ml) with stirring at 40 degrees Celcius for 48 hours. The cooled mixture was partitioned between ethyl acetate (500 mL) and saturated sodium bicarbonate solution (500 mL) and the organic phase separated. The aqueous phase was back extracted with ethyl acetate (500 mL) and the combined organics dried ($MgSO_4$), and the solvent evaporated to dryness in vacuo to leave a white solid (22.9 g, 95%). The solid was dissolved in hot ethyl acetate (100 ml). Toluene (400 ml) was added and the mixture brought to reflux. The mixture was filtered hot to remove insoluble impurities then allowed to cool slowly to room temperature with stirring over 2 hours. The mixture was filtered and washed with hexanes (100 mL) to give Compound (15) (16.3 g, 80%), m.p.=156-157.5° C.; $\delta_H${400 MHz, $CDCl_3$}7.35-7.18 (5H, m), 5.85 (1H, bs), 5.62 (1H, bs), 5.31 (2H, s), 3.96 (2H, bs), 2.96 (2H, bs), 2.81 (2H, bd, J=13.3 Hz), 2.25 (2H, bt, J=13.3 Hz), 1.45 (9H, s); TLC $SiO_2$ (EtOAc: hexanes, 1:1) Rf=0.18 detection U.V.; LC: 100% purity by DAD; MS: $[M+Na]^+$=409.2.

$^1$H NMR in $CDCl_3$ of this product did not detect any of the isomeric product, Compound (27):

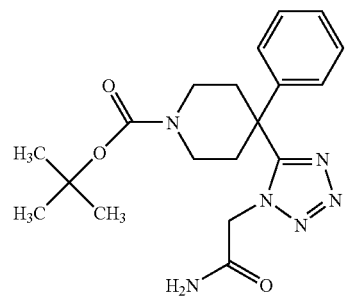

Compound (27)

A method for the isolation of Compound (27) is described below, in Section 5.13 (Example 13).

5.13. Example 13

Preparation of Compound (27) (4-(1-Carbamoylmethyl-2H-tetrazol-5-yl)-4-phenyl-piperidine-1-carboxylic acid tert-butyl ester)

Recrystallization of a 300 g batch of crude alkylated tetrazole (prepared generally as described in Section 5.12, Example 12) from ethylacetate: toluene (1:4) as above, gave a total of 255 g of Compound (15) (4-(2-Carbamoylmethyl-2H-tetrazol-5-yl)-4-phenyl-piperidine-1-carboxylic acid tert-butyl ester) in 73% yield. The mother liquors were concentrated to dryness in vacuo to give a pale yellow solid. Ethyl acetate (700 ml) was added and the mixture heated to reflux with stirring, and filtered hot to give Compound (27) (10.5 g) as a white solid >98% pure by 1H NMR and LC/MS. This was recrystallized from methanol to give Compound (27) (8.28 g) >99.9% pure by 1H NMR and LC/MS; $\delta_H${400 MHz, $(CD3)_2SO$} 7.67 (1H, bs), 7.47 (1H, bs), 7.41-7.28 (3H, m), 7.15 (2H, m), 4.53 (2H s), 3.80 (2H, m), 3.10 (2H, m), 2.43 (2H, m), 2.10 (2H, m), 1.40 (9H, s); LC: 100% purity by DAD; MS: $[M+Na]^+$=409.2

5.14. Example 14

Preparation of Compound (5)

(2-[5-(4-Phenyl-piperidin-4-yl)-tetrazol-2-yl]-acetamide)

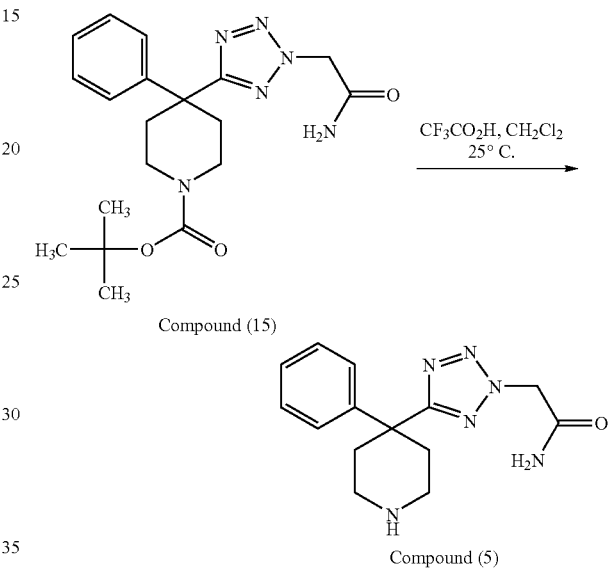

Compound (15)

Compound (5)

Compound (15) (4-(2-Carbamoylmethyl-2H-tetrazol-5-yl)-4-phenyl-piperidine-1-carboxylic acid tert-butyl ester) (130 g, 336.4 mMol) was suspended in dry dichloromethane (500 mL). Trifluoroacetic acid (150 mL) was added and the mixture stirred at room temperature for 2 h. The solvent was removed in vacuo and the residue poured into water (800 mL), and basified to pH 9 with potassium carbonate. The mixture filtered at this stage to remove some flecks of dark material. The colorless filtrate was basified further to >pH 12 with aqueous sodium hydroxide 1 M, and a seed crystal of the Compound (5) added. The mixture was stirred with ice-water cooling for 1 h and filtered to give a white crystalline solid which was dried under high vacuum for 18 h at 70 degrees Celcius over Drierite to give Compound (5) (70 g) as a white solid, m.p.=155-157° C. The aqueous filtrate was concentrated to about 300 ml in vacuo and the pH adjusted to >12 using sodium hydroxide 1M. A seed crystal of the desired product was added and the mixture stirred with ice-water cooling for 1 h and filtered to give further Compound (5) (12.2 g) which was dried under high vacuum at 70 degrees as before. Total yield of Compound (5) (82.2 g, 85.6%); $\delta_H${400 MHz, d6 DMSO}7.83 (1H, s), 7.46 (1H, s), 7.32-7.16 (5H, m), 5.38 (2H, s), 2.91 (2H, bd, J=12.3 Hz), 2.61 (2H, bd, J=12.3 Hz), 2.52 (2H, m), 2.10 (2H, bt, J=9.2 Hz); LC: 100% purity by DAD; MS: $[M+H]^+$=287.2

5.15. Example 15

Alternative Preparation of Compound (6)

(dimethyl(3,3-diphenyl-2-furylidene)ammonium bromide)

In addition to the methods disclosed above in Section 5.4 and Section 5.7, above, Compound (6) may also be prepared as follows: 4-Bromo-2,2-diphenyl butyric acid (50 g, 156.7 mMol) was suspended in dichloromethane (250 mL). Oxalyl chloride (14.4 mL, 164.5 mMol) was added and the mixture heated under reflux under argon for 2 h. Reaction time was assessed when evolution of gases ceased, and the solvent was then removed in vacuo to give the crude acid chloride, which was used immediately. Sodium carbonate (19.9 g, 188.04 mMol) was dissolved in water (200 mL) and the solution cooled to −5° C. (ice-acetone). Aqueous dimethylamine 40% w/w 7.9 M (24 mL, 188.04 mMol) was added, followed by toluene (200 mL). The acid chloride in toluene (250 ml) was added over 15 minutes keeping the temperature below 0° C. during the addition, and the resulting mixture stirred for an additional hour at this temperature. The organic layer was separated (discarded to remove impurities) and the aqueous layer extracted with dichloromethane (5×500 mL), dried (MgSO$_4$) and the solvent evaporated in vacuo to leave an off-white solid which was left on the rotary evaporator at 50° C. for 20 minutes. The solid was triturated with ethyl acetate (250 ml) to give Compound (6) (37.5 g, 69.4 %) as a white solid. $\delta_H$ {400 MHz, CDCl$_3$} 7.56-7.36 (10H, m), 4.86 (2H, t, J=7.0 Hz), 3.82 (3H, s), 3.47 (2H, t, J=7.0 Hz), 2.96 (3H, s).

5.16. Example 16

Preparation of Compound (7) (4-[4-(2-Carbamoylmethyl-2H-tetrazol-5-yl)-4-phenyl-piperidin-1-yl]-N,N-dimethyl-2,2-diphenyl-butyramide)

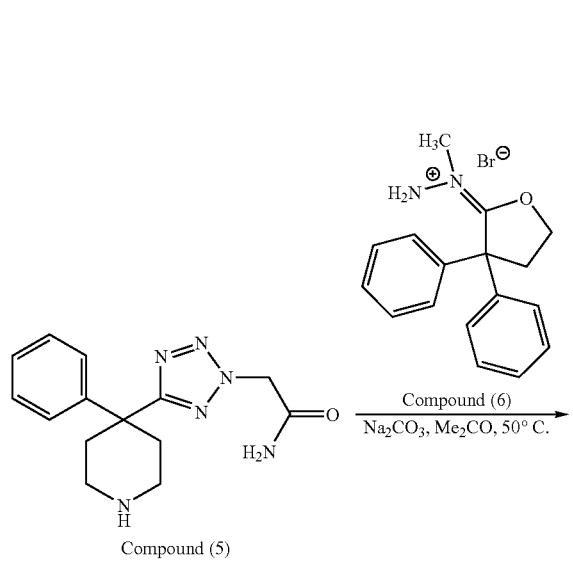

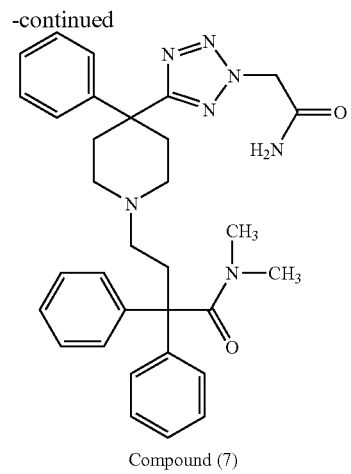

Compound (7)

Compound (5) (as the 2-[5-(4-Phenyl-piperidin-4-yl)-tetrazol-2-yl]-acetamide trifluoroacetic acid salt) (1 g, 2.5 mMol), Compound (6) (3,3-Diphenyl-dihydro-furan-2-ylidene)-dimethyl-ammonium bromide): triethylamine hydrochloride (1:1 mixture) (1.33 g, 2.75 mMol) and sodium carbonate (0.795 g, 7.5 mMol) were suspended in dry acetone (20 mL) and heated to 50 degrees Celcius for 18 h. The cooled mixture was partitioned between ethyl acetate (100 mL) and 8% aqueous sodium bicarbonate (100 mL) and the organic phase separated, dried (MgSO$_4$) and the solvent evaporated to dryness in vacuo to leave a yellow gum. Flash chromatography of the residue eluting with ethyl acetate:methanol:ammonia (100:10:10) gave a foam. This was dissolved in acetonitrile (25 ml) and allowed to crystallize slowly. The mixture was filtered to give Compound (7) as a white solid (930 mg, 67%). $\delta_H$ {400 MHz, d6 CDCl3} 7.40-7.13 (15H, m), 5.89 (1H, bs), 5.68 (1H, bs), 5.27 (2H, s), 2.96 (3H, bs), 2.75 (4H, m), 2.40 (2H, m), 2.30 (5H, m), 2.09-1.93 (4H, m), 1.72 (4H, m); LC: 100% by DAD; MS: [M+H]$^+$=552.3/553.3

5.17. Example 17

Synthesis of Compound (18) (5-benzyl-1-H-tetrazole)

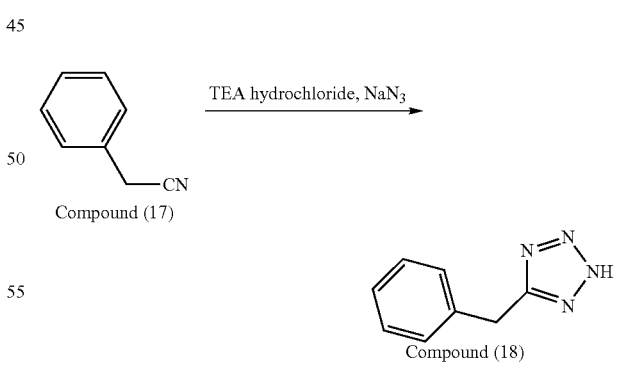

Compound (17) (benzyl cyanide) (49 mL; 425 mmol), NaN$_3$ (33.15 g; 510 mmol), and triethylamine hydrochloride (70 g; 510 mmol) were suspended in 800 mL of dry toluene. The mixture was warmed to 100° C. under Ar and stirred at this temperature for 16 hr. Upon cooling 800 mL of DI water was added. The aqueous layer was removed and acidified to pH<4 using concentrated HCl. The aqueous layer was then extracted with 3×500 mL ethyl acetate. The ethyl acetate layers were combined and dried over Mg$_2$SO$_4$, filtered and concentrated to dryness affording Compound (18) as a white solid. Yield 100%; δ$_H$ (400 MHz, CDCl$_3$): 7.28 (5H, m), 4.35 (2H, s). LC/MS=(100%, t$_r$=2.234 min), m/z=161.0 [M+H]$^+$ Calc: 160.0.

5.18. Example 18

Synthesis of Compound (20)

(5-Benzyl-2-(1-methyl-1-phenyl-ethyl)-2H-tetrazole)

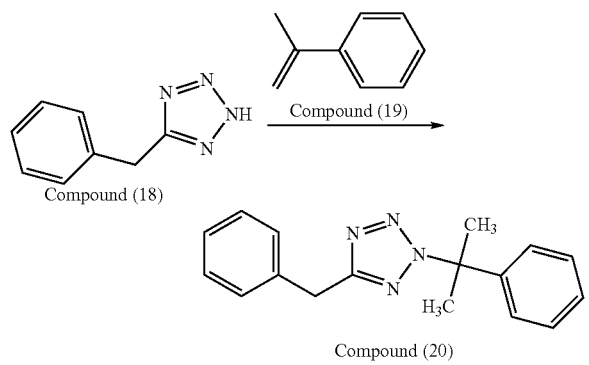

The benzyltetrazole, Compound (18) (50 g; 310 mmol) and trichloroacetic acid (116.95 g; 713 mmol) were suspended in 500 mL of CHCl$_3$. These were stirred and Compound (19) (α-methylstyrene) (40.3 mL; 310 mmol) in 50 mL of CHCl$_3$ was added dropwise over 10 min. After stirring for 1 hr 500 mL of 10% KOH$_{(aq)}$ was added. The organic layer was separated, dried over Mg$_2$SO$_4$, filtered and concentrated to dryness. The crude material was taken up in neat hexanes and filtered through a plug of silica washing with hexanes until all excess Compound (19) (α-methylstyrene) was removed. Subsequent washing with 50% ethyl acetate in hexanes afforded the desired protected tetrazole, Compound (20) after concentration to dryness. 81.87 g of the product, Compound (20), was obtained as a colorless oil. Yield 95%; δ$_H$ (400 MHz, CDCl$_3$): 7.30 (8H, m), 7.08 (2H, d, J=8 Hz). LC/MS= (100%, t$_r$=4.889 min), m/z=301.1 [M+H]$^+$Calc: 278.36.

5.19. Example 19

Synthesis of Compound (24)

(4-phenyl-4-(2-(2-phenylpropan-2-yl)-2H-tetrazol-5-yl)-1-tosylpiperidine)

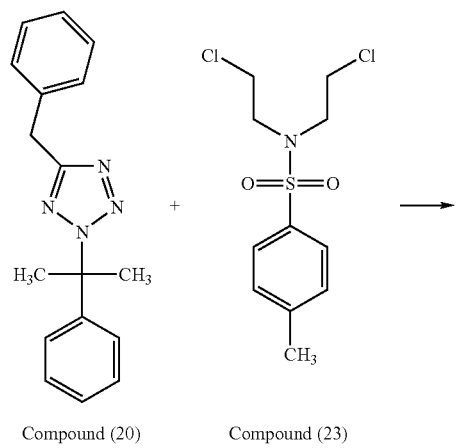

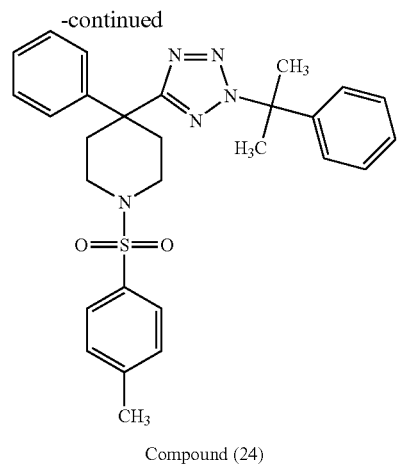

Compound (20) (5-benzyl-2-(2-phenylpropan-2-yl)-2H-tetrazole) (20 g, 71.85 mmol) was taken up in 400 mL of dry diethyl ether. This was cooled to −15° C. under Ar. 1.6M n-BuLi in hexanes (99 ml, 158.07 mmol) was added dropwise over 10 min. The mixture was stirred for 0.5 hr. Compound (23) (N-tosyl-bis-(2-chloroethyl)amine) (25.5 g, 86.22 mmol) in 100 mL diethyl ether was added dropwise over 10 min. The mixture was allowed to warm to room temperature and stir for 16 hr. The reaction was quenched with 400 mL of saturated NH$_4$Cl$_{(aq)}$. Ethyl acetate (100 mL) was added and the layers were separated. The organics were dried over Mg$_2$SO$_4$, filtered and concentrated to dryness. A small amount of Compound (24) was purified by chromatography eluting with EtOAc/Hexanes (1:4). White Solid. δ$_H$ (400 MHz, CDCl$_3$): 7.58 (2H, d, J=8 Hz), 7.19-7.29 (10H, m), 6.82 (2H, d, J=8Hz), 3.73 (2H, m), 2.89 (2H, m), 2.44 (3H, s), 2.37 (4H, m), 2.01(6H, s). LC/MS=(100%, t$_r$=3.742 min), m/z=524.3 [M+H]$^+$Calc: 501.66. The remaining crude Compound (24) was taken on to the next step (Section 5.20, Example 20).

5.20. Example 20

Synthesis of Compound (25)

(4-phenyl-4-(2H-tetrazol-5-yl)-1-(toluene-4-sulfonyl)-piperidine)

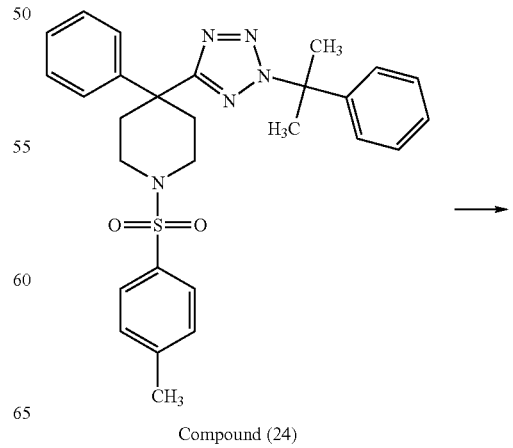

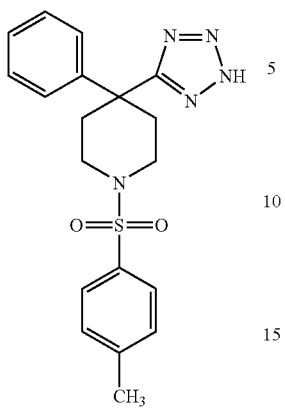

Compound (25)

Crude Compound (24) was taken up in 50 mL of absolute ethanol. To this potassium formate (36 g; 431.1 mmol), and 10% Pd/C (13 g) were added. These were stirred at reflux for 4 hr. The mixture was then filtered through celite and the filtrate concentrated to dryness affording crude Compound (25). This material was partitioned between water and ethyl acetate. The ethyl acetate layer was separated and backwashed with water. The aqueous fractions were combined and acidified to pH<3 (HCl conc). Extraction of the aqueous layer with ethyl acetate followed by separation, drying (Mg$_2$SO$_4$), and concentration to dryness gave substantially pure Compound (25), which could be used without further purification. Twenty-five grams of the product, Compound (25), was obtained as a white foam. $\delta_H$ (400 MHz, CDCl$_3$): 7.51 (2H, d, J=8Hz), 7.10-7.29 (7H, m), 3.59 (2H, m), 2.69 (2H, m), 2.20-2.38 (7H, m), 2.37 (4H, m). LC/MS=(85%, t$_r$=2.730 min), m/z=384.1 [M+H]$^+$Calc: 383.48.

5.21. Example 21

Synthesis of Compound (26)

(2-{5-[4-Phenyl-1-(tolunene-4-sulfonyl)-piperidin-4-yl]tetrazol-2-yl}-acetamide)

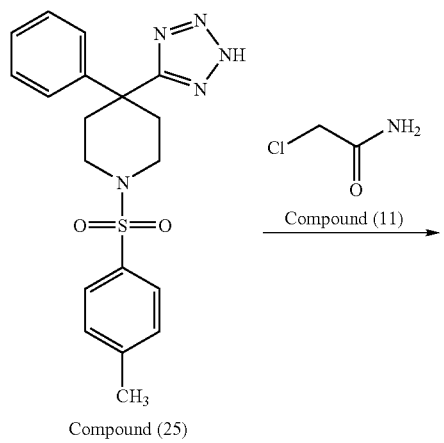

Compound (25)  Compound (11)

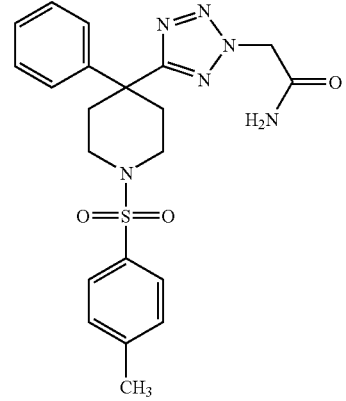

Compound (26)

Crude Compound (25) (3.5 g) was taken up in 100 mL of acetone. To this NaI (1.2 eq), K$_2$CO$_3$ (1.2 eq), and Compound (11) (2-chloroacetamide) (1 eq) were added. These were stirred and warmed to 40° C. for 4 hr. The mixture was partitioned between DI water and ethyl acetate. The layers were separated and the organics were dried over Mg$_2$SO$_4$, filtered, and concentrated to dryness. Ethyl acetate was added and the crude material was recrystallized affording 3.7 g of Compound (26) as a white crystalline solid. Yield 89%. $\delta_H$ (400 MHz, CDCl$_3$): 7.61 (2H, d, J=8Hz), 7.22 (7H, m), 5.91 (1H, bs), 5.72 (1H, bs), 5.20 (2H, s), 3.69 (2H, m), 2.85 (2H, m), 2.53 (2H, m), 2.40 (5H, m). LC/MS=(100%, t$_r$=2.936 min), m/z=441.1 [M+H]$^+$Calc: 440.16.

5.22. Example 22

Synthesis of Compound (5)

(2-[5-(4-Phenyl-piperidin-4-yl)-tetrzol-2-yl]-acetamide)

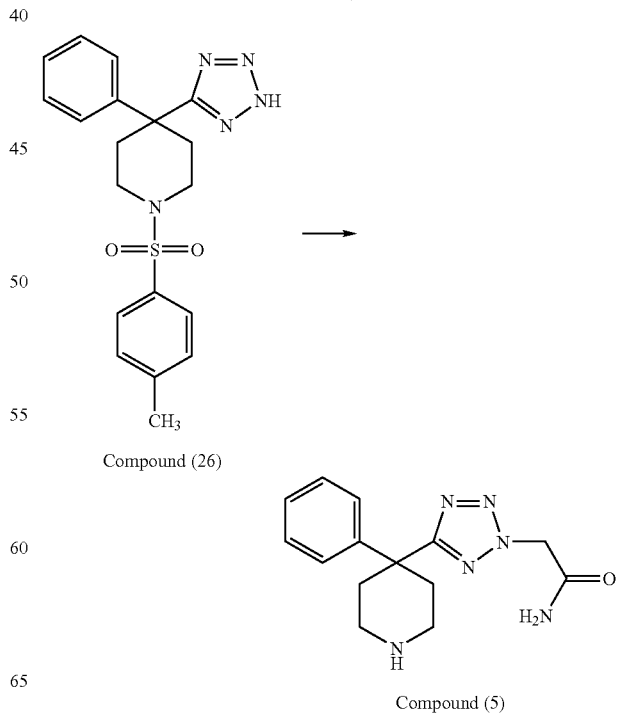

Compound (26)

Compound (5)

Compound (26) (3.7 g; 8.39 mmol) was suspended in 60 mL of concentrated sulfuric acid. This was warmed to 115° C. for 8 hours. The mixture was cooled to room temperature and added dropwise to 400 mL of 6M NaOH at 10° C. with vigorous stirring. LC/MS shows no starting material and peaks corresponding to tosic acid and the desired product, Compound (5). The product was extracted with ethyl acetate (10×500 mL). The organics were concentrated to dryness, yielding 2.2 g crude Compound (5).

The present invention is not to be limited in scope by the specific embodiments disclosed in the examples which are intended as illustrations of a few aspects of the invention. Therefore, any embodiments that are functionally equivalent to those disclosed herein are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference, in their entirety.

What is claimed is:

1. A method for making a compound according to formula (9)

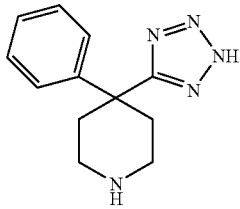

(9)

comprising allowing a compound of formula (8)

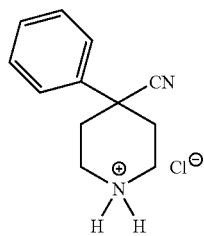

(8)

to react with sodium azide and a zinc salt in a solvent comprising a polar aprotic solvent, whereby the compound of formula (9) is formed.

2. A method for making Compound (7)

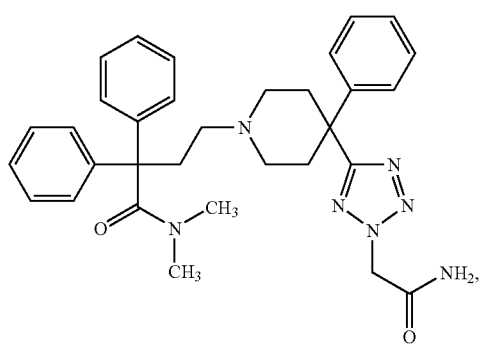

(7)

comprising allowing a compound of formula (5)

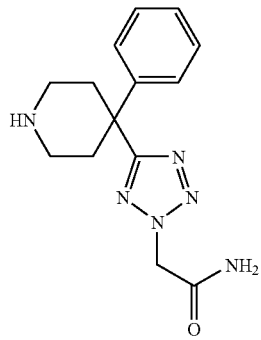

(5)

to react with a compound of formula (6)

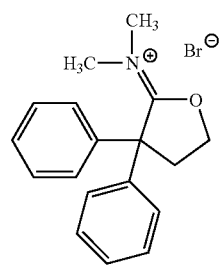

(6)

in the presence of a base in a solvent comprising a polar aprotic solvent to produce compound (7).

3. The method of claim 2, wherein the polar aprotic solvent is selected from the group consisting of N-methyl pyrrolidone, dimethyl formamide, dimethyl acetamide, acetonitrile, dimethyl sulfoxide, and combinations thereof.

4. The method of claim 2, wherein the base is selected from the group consisting of triethylamine, diisipropylethylamine, sodium carbonate, potassium carbonate, cesium carbonate, and combinations of two or more thereof.

5. The method of claim 2 further comprising debenyzlating a compound of formula (4)

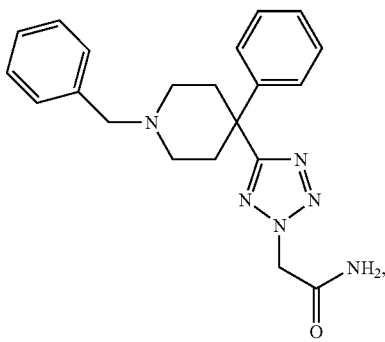

(4)

in the presence of hydrogen gas and a precious-metal catalyst to provide the compound of formula (5)

(5)

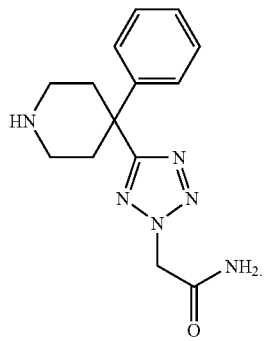

6. The method of claim 5 further comprising allowing a compound of formula (2)

(2)

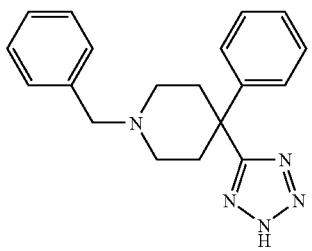

to react with a compound of Formula IX

Formula IX

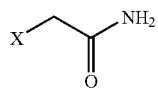

where X is selected from the group consisting of Br, Cl, and I, in the presence of a non-nucleophilic base to provide the compound of formula (4)

(4)

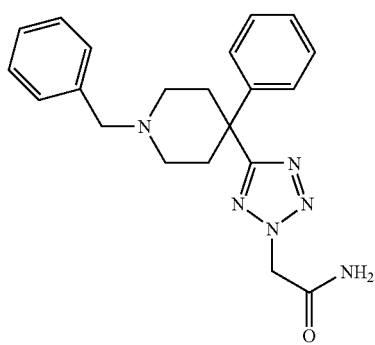

7. The method of claim 6 further comprising allowing a compound of formula (1)

(1)

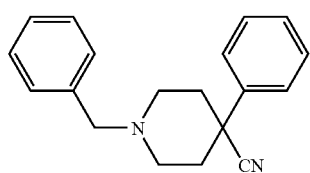

to react with sodium azide in the presence of a zinc salt, to provide the compound of formula (2)

(2)

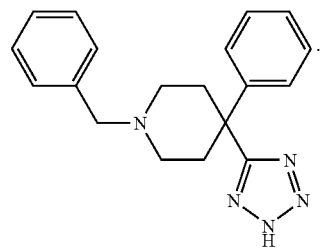

8. The method of claim 2 further comprising deprotecting a compound of formula (15)

(15)

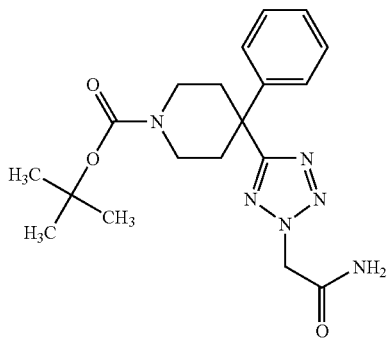

to produce the compound of formula (5)

(5)

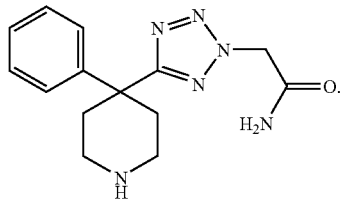

9. The method of claim 2 further comprising deprotecting a compound of formula (26)

(26)

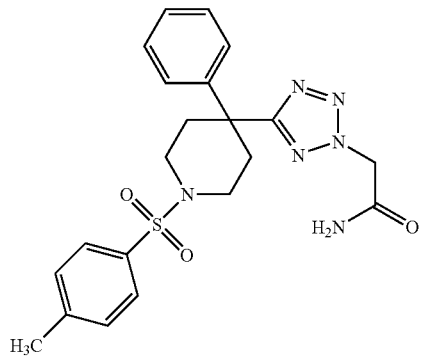

to produce the compound of formula (5)

(5)

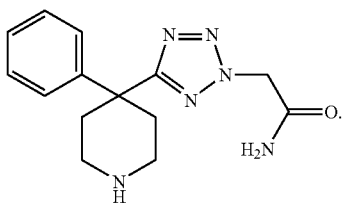

10. The method of claim 8 further comprising allowing a compound of formula (14)

(14)
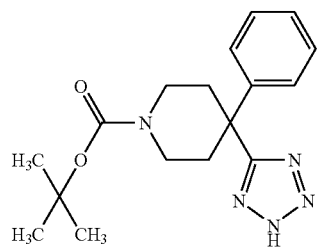

to react with a compound of Formula IX

IX
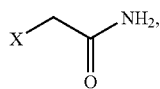

wherein X is selected from the group consisting of Br, Cl, or I, in the presence of a non-nucleophilic base to produce the compound of formula (15)

(15)
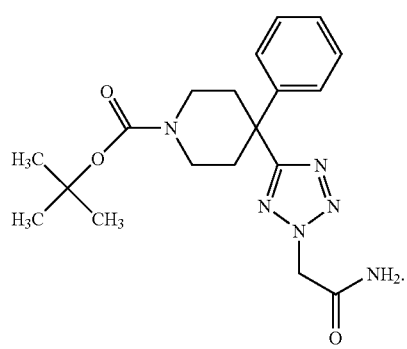

11. The method of claim 9 further comprising allowing a compound of formula (25)

(25)
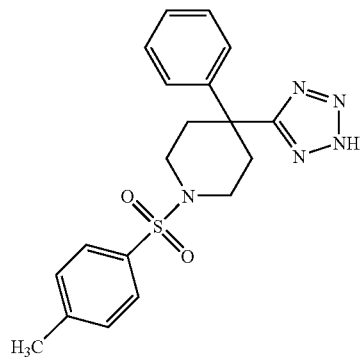

to react with a compound of Formula IX

IX
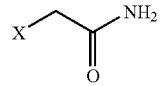

wherein X is selected from the group consisting of Br, Cl, or I, in the presence of a non-nucleophilic base to produce the compound of formula (26)

(26)
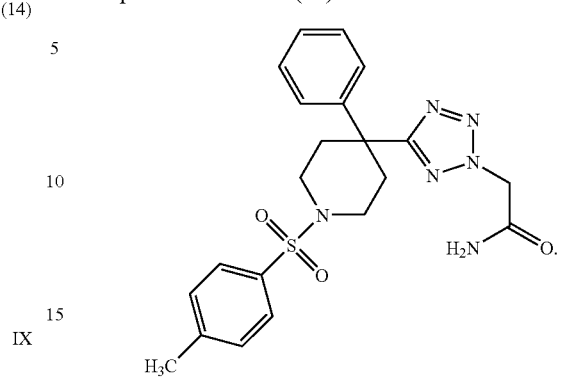

12. The method of claim 10 further comprising allowing a compound of formula (20)

(20)
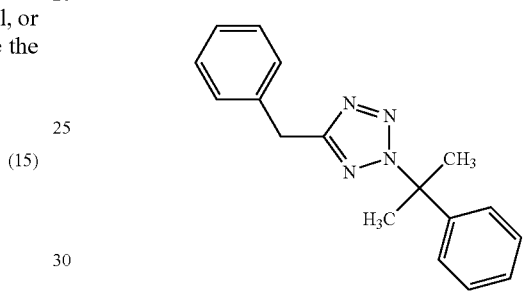

to react with a compound of formula (21)

(21)
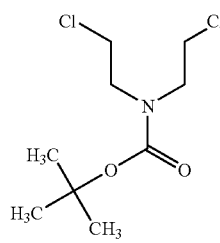

to produce a compound of formula (22)

(22)
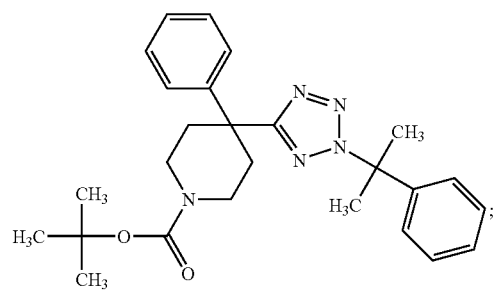

and deprotecting the compound of formula (22) to provide the compound of formula (14)

(14)
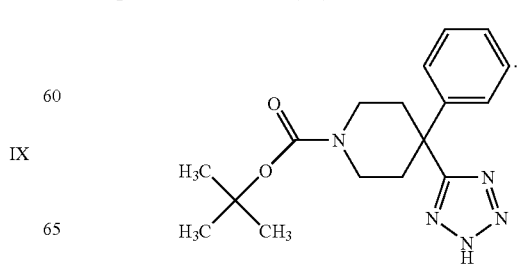

13. The method of claim 11 further comprising allowing a compound of formula (20)

(20)

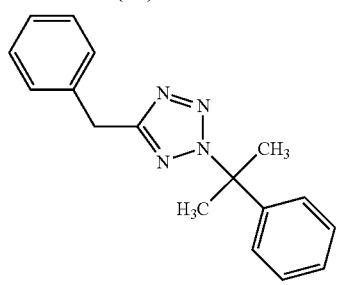

to react with a compound of formula (23)

(23)

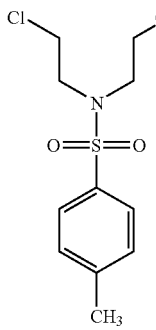

to produce a compound of formula (24)

(24)

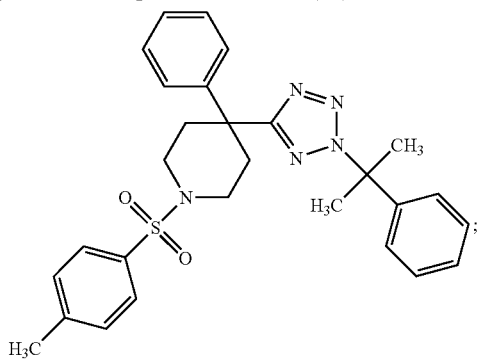

and deprotecting compound (24) to provide the compound of formula (25)

(25)

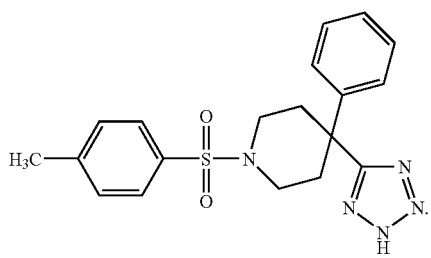

14. The method of claim 10 further comprising allowing a compound of formula (9)

(9)

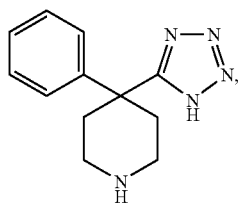

to react with a compound of formula (12)

(12)

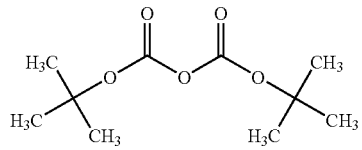

to produce the compound of formula (14)

(14)

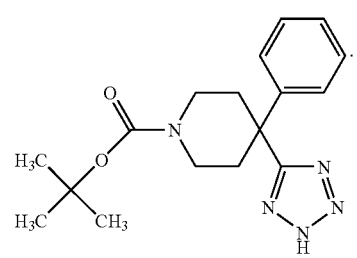

15. The method of claim 11 further comprising allowing a compound of formula (9)

(9)

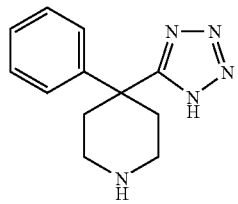

to react with a compound of formula (28)

(28)

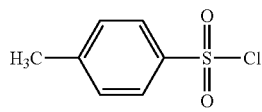

to produce the compound of formula (25)

(25)

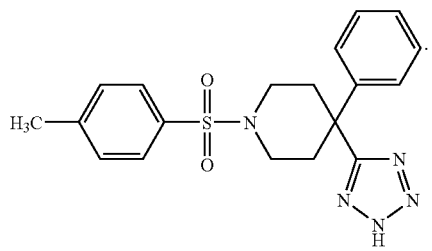

16. A method for making Compound (7)

(7)

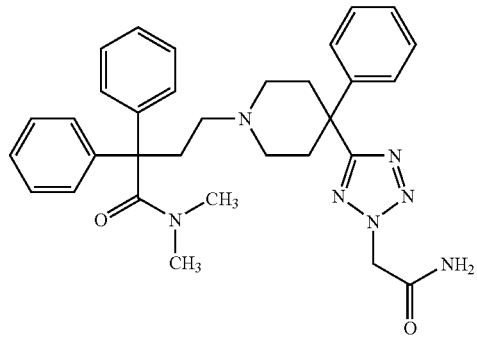

comprising allowing a compound of formula (9)

(9)

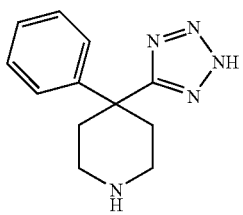

to react with a compound of formula (6)

(6)

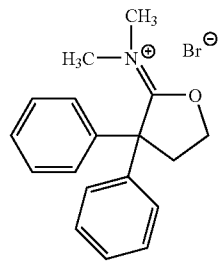

in a solvent comprising a polar aprotic solvent in the presence of a base, to provide a compound of formula (10);

(10)

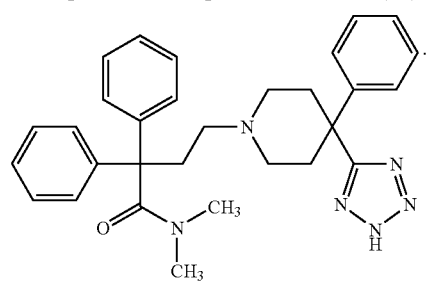

and allowing the compound of formula (10) to react with a compound of Formula IX Formula IX

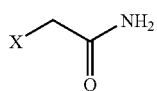

where X is selected from the group consisting of Br, Cl, and I, whereby Compound (7) is formed.

17. The method of claim 16 further comprising allowing a compound of formula (8)

(8)

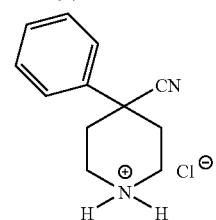

to react with sodium azide in the presence of a zinc salt in a solvent comprising a mixture of water and dioxane to provide the compound of formula (9)

(9)

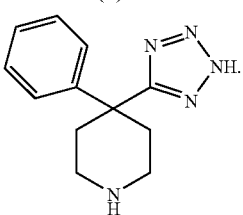

18. A method for making Compound (7)

(7)

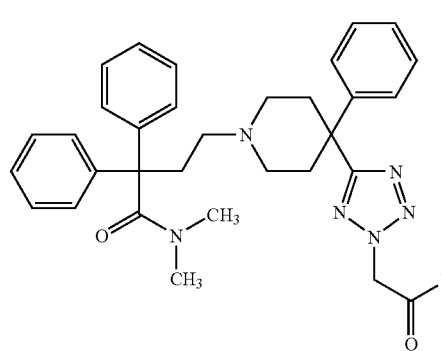

comprising allowing a compound of formula (20)

(20)

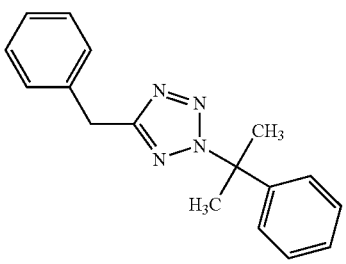

to react with a compound of formula (35)

(35)

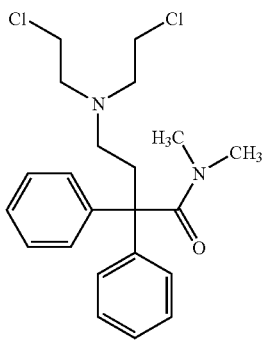

to produce a compound of formula (36)

(36)

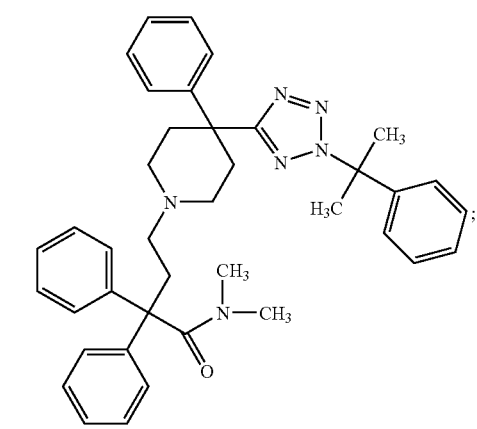

deprotecting the compound of formula (36) to provide a compound of formula (10);
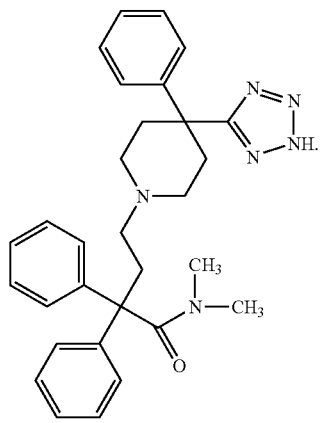
(10)
and allowing the compound of formula (10) to react with a compound of Formula IX
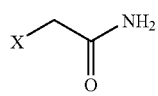
Formula IX
where X is selected from the group consisting of Br, Cl, and I, whereby Compound (7) is formed.
* * * * *